(12) United States Patent
Kim

(10) Patent No.: US 12,372,284 B2
(45) Date of Patent: Jul. 29, 2025

(54) LASER SURGICAL DEVICE AND SURGICAL METHOD THEREOF

(71) Applicants: RECENSMEDICAL, INC., Ulsan (KR); ULSAN NATIONAL INSTITUTE OF SCIENCE AND TECHNOLOGY, Ulsan (KR)

(72) Inventor: Gun-Ho Kim, Ulsan (KR)

(73) Assignees: RecensMedical, Inc., Hwaseong-si (KR); Ulsan National Institute of Science & Technology, Ulsan (KR)

( * ) Notice: Subject to any disclaimer, the term of this patent is extended or adjusted under 35 U.S.C. 154(b) by 378 days.

(21) Appl. No.: 18/073,274

(22) Filed: Dec. 1, 2022

(65) Prior Publication Data

US 2023/0086046 A1 Mar. 23, 2023

Related U.S. Application Data

(63) Continuation of application No. PCT/KR2020/012886, filed on Sep. 23, 2020.

(30) Foreign Application Priority Data

Jun. 5, 2020 (KR) .................. 10-2020-0068479
Jun. 5, 2020 (KR) .................. 10-2020-0068480
(Continued)

(51) Int. Cl.
*F25B 49/02* (2006.01)
*A61B 18/00* (2006.01)
*A61B 18/20* (2006.01)

(52) U.S. Cl.
CPC .... *F25B 49/02* (2013.01); *A61B 2018/00029* (2013.01); *A61B 2018/00452* (2013.01);
(Continued)

(58) Field of Classification Search
CPC ................. F25B 49/02; A61B 18/203; A61B 2018/00029; A61B 2018/00452;
(Continued)

(56) References Cited

U.S. PATENT DOCUMENTS 5,814,040 A 9/1998 Nelson et al.
5,979,454 A 11/1999 Anvari et al.
(Continued)

FOREIGN PATENT DOCUMENTS

JP 8-317933 A 12/1996
JP 2002-503987 A 2/2002
(Continued)

OTHER PUBLICATIONS

European Extended Search Report dated Apr. 15, 2024 for EP 20938762.0.
(Continued)

*Primary Examiner* — Aaron F Roane
(74) *Attorney, Agent, or Firm* — Knobbe, Martens, Olson, & Bear, LLP

(57) ABSTRACT

Proposed is a laser treatment device having a cooling system, the device including a laser module which irradiates a patient's skin with a laser, a sensing unit which detects a temperature of a surface of the patient's skin before, during, or after the skin is heated by the laser, a cooling module which includes an inlet which receives a refrigerant from a refrigerant storage unit, a nozzle which sprays the refrigerant on the skin, a conduit which connects the inlet with the nozzle, an flow rate control unit which controls a spray amount of the refrigerant by using a valve which is positioned on the conduit and connects or disconnects the inlet with or from the nozzle, and a refrigerant condition control
(Continued)

unit which applies a thermal energy to the refrigerant by using a thermoelectric element located between the flow rate control unit and the nozzle.

15 Claims, 24 Drawing Sheets

(30) Foreign Application Priority Data

Jun. 5, 2020 (KR) .................. 10-2020-0068481
Jun. 5, 2020 (KR) .................. 10-2020-0068482

(52) U.S. Cl.
CPC ............... *A61B 2018/00642* (2013.01); *A61B 2018/00714* (2013.01); *A61B 2018/00744* (2013.01); *A61B 2018/00791* (2013.01); *A61B 2018/00797* (2013.01); *A61B 18/203* (2013.01)

(58) Field of Classification Search
CPC ........... A61B 2018/00642; A61B 2018/00714; A61B 2018/00744; A61B 2018/00791; A61B 2018/00797
USPC .......................................................... 607/89
See application file for complete search history.

(56) References Cited

U.S. PATENT DOCUMENTS

| | | | |
|---|---|---|---|
| 10,994,151 | B2 | 5/2021 | Daly et al. |
| 2003/0065313 | A1 | 4/2003 | Koop et al. |
| 2012/0010603 | A1* | 1/2012 | Milner ................. A61B 5/0075 607/88 |
| 2016/0354144 | A1* | 12/2016 | Caplan ............... A61B 18/1492 |
| 2017/0333122 | A1* | 11/2017 | Rajagopalan ......... A61M 29/02 |
| 2018/0140866 | A1 | 5/2018 | Daly et al. |
| 2019/0239938 | A1 | 8/2019 | Kazic et al. |
| 2020/0054482 | A1 | 2/2020 | Manstein et al. |

FOREIGN PATENT DOCUMENTS

| | | | |
|---|---|---|---|
| KR | 20120115703 | * | 10/2012 |
| KR | 20120115703 | A | 10/2012 |
| KR | 20160146337 | A | 12/2016 |
| KR | 20180109828 | A | 10/2018 |
| KR | 20180131352 | A | 12/2018 |
| KR | 20190074150 | A | 6/2019 |
| KR | 10-2019-0089176 | A | 7/2019 |
| KR | 10-2010580 | B1 | 8/2019 |
| KR | 102020019 | B1 | 10/2019 |
| KR | 20190124971 | A | 11/2019 |
| KR | 20200012675 | A | 2/2020 |
| WO | WO-2021246580 | A1 | 12/2021 |

OTHER PUBLICATIONS

Japanese Notice of Reasons for Refusal with Translation, for JP Application No. 2022-575272, dated Jun. 18, 2024.
Japanese Decision to Grant with Translation, for JP Application No. 2022-575272, dated Dec. 3, 2024.
International Preliminary Report on Patentability dated issued Dec. 6, 2022, for PCT/KR2020/012886.
Korean Notice of Allowance dated Nov. 30, 2022, for KR 10-2020-0068480.
Korean Written Opinion dated Jan. 18, 2022, for KR 10-2020-0068482.
Korean Final Office Action and Written Opinion dated Jun. 27, 2022, for KR 10-2020-0068482.
Korean Written Opinion dated Sep. 22, 2022, for KR 10-2020-0068482.
Korean Written Decision dated Oct. 25, 2022, for KR 10-2020-0068482.
Korean Office Action issued in corresponding application No. 10-2020-0068479, dated Nov. 23, 2021.
Korean Office Action issued in corresponding application No. 10-2020-0068480, dated Nov. 23, 2021.
Korean Office Action issued in corresponding application No. 10-2020-0068481, dated Nov. 18, 2021.
Notice of Allowance issued in corresponding application No. KR 10-2020-0068481, dated Jan. 19, 2023.
PCT/KR2020/012886 International Search Report and Written Opinion, with English translations included, dated Mar. 3, 2021.
Korean Application No. 10-2020-0068479 Notice of Allowance dated May 19, 2023.
Chinese First Office Action, with English translation, dated May 16, 2025, for CN 202080104111.0.

* cited by examiner

S10000

| Setting a first temperature and a second temperature based on dry ice formation temperature | — S10100 |

↓

| Controlling refrigerant temperature based on first temperature | — S10200 |

↓

| Laser emission | — S10300 |

↓

| Controlling refrigerant temperature based on second temperature | — S10400 |

Fig. 21

LASER SURGICAL DEVICE AND SURGICAL METHOD THEREOF

CROSS-REFERENCE TO RELATED APPLICATIONS

The present application is a continuation of International Patent Application No. PCT/KR2020/012886, filed Sep. 23, 2020, which claims the benefit of Korean Patent Application No. 10-2020-0068479, filed Jun. 5, 2020, Korean Patent Application No. 10-2020-0068480, filed Jun. 5, 2020, Korean Patent Application No. 10-2020-0068481, filed Jun. 5, 2020, Korean Patent Application No. 10-2020-0068482, filed Jun. 5, 2020, the contents of which are incorporated by reference in their entirety.

TECHNICAL FIELD

The present disclosure relates generally to a laser treatment device and a treatment method thereof. More particularly, the present disclosure relates to a laser treatment device having a cooling system and a treatment method thereof.

BACKGROUND ART

In general, a laser treatment device is widely used for a treatment or treatment for skin care, vascular lesions, hair removal, or wart removal. Particularly, in a modern society, interest in skin care is soaring, thus increasing interest in and research on the laser treatment device.

However, due to the characteristics of laser treatment, a laser that outputs high energy in a very short time is used for the skin of the body, so thermal energy accumulates in a specific area of the skin, which is likely to cause skin damage by heat. Additionally, since the treatment is performed on the principle of causing heat ablation on a specific part of the skin by outputting high energy in a short time, there is a high possibility of pain caused by the heat ablation.

To this end, the laser treatment has been carried out in a way that cooling is performed together with laser irradiation. In the case of conventional cooling, there have been contact-type cooling, non-contact-type cooling, and air gas-used cooling, and in particular, in the case of a conventional spray-type cooling, when spraying a refrigerant, strong pressure of the sprayed refrigerant is applied to and wears internal components of a spraying unit, thereby decreasing durability of the components and accordingly causing high costs due to an after service (AS) for the components. Additionally, in the case of spray cooling, since the spraying of a refrigerant proceeds by depending on the practitioner's experience, there are still side effects of skin damage and pain.

Accordingly, a laser treatment device having a cooling system to prevent damage due to heat and relieve pain and a treatment method thereof are requested.

DISCLOSURE

Technical Problem

An objective of the present disclosure is to propose a laser treatment device having a spraying cooling system and a treatment method thereof.

Another objective of the present disclosure is to propose a laser treatment device which is used to control the temperature of a refrigerant by measuring the 'temperature' of the skin, which is a direct factor of skin damage, and a treatment method thereof.

Still another objective of the present disclosure is to propose a laser treatment device which precisely controls the temperature or amount of a refrigerant based on a measured temperature of the skin and a treatment method thereof.

Still another objective of the present disclosure is to propose a laser treatment device having a spraying cooling system which performs cooling before, during, or after laser irradiation performed by the laser treatment device and a treatment method thereof.

Still another objective of the present disclosure is to propose a laser treatment device having a spraying cooling system which prevents sudden pressure rise when a refrigerant is sprayed and a treatment method thereof.

Still another objective of the present disclosure is to propose a laser treatment device having a spraying cooling system which solves and/or prevents the error of skin temperature measurement which may occur during laser irradiation and a treatment method thereof.

Technical Solution

A laser treatment device having a cooling system disclosed in the present specification includes: a laser module which irradiates a patient's skin with a laser; a sensing unit which detects a temperature of a surface of the patient's skin before, during, or after the skin is heated by the laser; a cooling module including: an inlet which receives a refrigerant from a refrigerant storage part; a nozzle which sprays the refrigerant on the skin; a conduit which connects the inlet with the nozzle; a flow rate control unit which controls a spray amount of the refrigerant by using a valve which is positioned on the conduit and connects or disconnects the inlet with or from the nozzle; and a refrigerant condition control unit which applies a thermal energy to the refrigerant by using a thermoelectric element located between the flow rate control unit and the nozzle, the cooling module being configured to cool the surface of the skin before, during, or after the skin is heated by the laser by spraying the refrigerant; and a control module which obtains skin temperature information through the sensing unit; controls a temperature of the refrigerant to be sprayed by controlling the thermal energy applied to the refrigerant from the refrigerant condition control unit based on the skin temperature information; and controls the temperature of the skin surface to reduce damage to the skin surface being heated by the laser.

The laser treatment device having a cooling system disclosed in the present specification may include: the laser module which outputs a laser to the patient's skin for laser treatment; the sensing unit which measures the temperature of the skin; the nozzle which sprays a refrigerant on the skin; the refrigerant condition control unit which controls at least one of the temperature and spray amount of the refrigerant; and the control module configured to control at least one of the temperature and amount of the refrigerant based on at least one of first skin information and second skin information when performing the laser treatment of a second shot after the laser treatment of a first shot after obtaining at least one of the first skin information and the second skin information through the sensing unit, the first skin information including at least a skin temperature when or before the laser output of the first shot starts, and the second skin information including at least a skin temperature when or after the laser output of the first shot stops.

The laser treatment method using a cooling system disclosed in the present specification includes: irradiating a patient's skin with a laser through the laser module; measuring, through the sensing unit, the temperature of the surface of the skin before, during, or after the skin is heated by the laser; cooling the skin surface before, during, or after the skin is heated by the laser by spraying a refrigerant through the cooling module including: the inlet which receives the refrigerant from the refrigerant storage unit; the nozzle which sprays the refrigerant on the skin; the conduit which connects the inlet with the nozzle; the flow rate control unit which controls the spray amount of the refrigerant by using the valve which is positioned on the conduit and connects or disconnects the inlet with or from the nozzle; and the refrigerant condition control unit which applies thermal energy to the refrigerant by using the thermoelectric element located between the flow rate control unit and the nozzle; and controlling, through the control module, the temperature of the skin surface to reduce damage to the skin surface being heated by the laser by controlling the temperature of the refrigerant to be sprayed by controlling thermal energy applied to the refrigerant from the refrigerant condition control unit based on skin temperature information after obtaining the skin temperature information from the sensing unit.

The laser treatment method using a cooling system disclosed in the present specification includes: outputting a laser to a patient's skin through the laser module; measuring the temperature of the skin through the sensing unit; spraying a refrigerant on the skin through the nozzle; controlling at least one of temperature and amount of the refrigerant through the refrigerant condition control unit; obtaining at least one of the first skin information and second skin information from the sensing unit through a control module, wherein the first skin information may include at least a temperature of the skin when or before the laser output of the first shot starts, and the second skin information may include at least a temperature of the skin when or after the laser output of the first shot stops; and controlling at least one of the temperature and amount of the refrigerant, through the control module, based at least one of the first skin information and the second skin information when performing the laser treatment of the second shot after performing the laser treatment of the first shot.

The laser treatment device having a cooling system disclosed in the present specification, which is used in laser therapy and has a cooling function, may include: the laser module which irradiates a patient's skin with a laser; the sensing unit which obtains the skin temperature information by detecting the patient's skin surface temperature before the skin is heated by the laser; the cooling module including the nozzle which sprays the refrigerant on the skin surface, and the refrigerant condition control unit which controls the temperature of the refrigerant by applying thermal energy to the refrigerant; and the control module in which laser irradiation is performed on the skin through the laser module, the cooling module is controlled such that the spraying of a refrigerant on the skin is started before the laser irradiation, at least one of the spray amount and temperature of a refrigerant is controlled based on the skin temperature information during the spraying of the refrigerant, whether the skin surface temperature reaches the predetermined first set temperature is detected, and the laser irradiation is started when the skin surface temperature reaches the predetermined first set temperature.

The laser treatment device having a cooling system disclosed in the present specification, which is used in laser therapy and has a cooling function, may include: the laser module which irradiates a patient's skin with a laser; the sensing unit which obtains the skin temperature information by detecting the patient's skin surface temperature before the skin is heated by the laser; the cooling module including the nozzle which sprays a refrigerant on the skin surface and the refrigerant condition control unit which controls the temperature of the refrigerant by applying thermal energy to the refrigerant; and a notification module which provides notification which guides a user to provide the laser therapy to the skin; a trigger which obtains a user's input about the laser irradiation; and the control module in which the laser irradiation on the skin is performed through the laser module, and the cooling module is controlled to start the spraying of the refrigerant on the skin before the laser irradiation, at least one of the spray amount and temperature of the refrigerant is controlled based on the skin temperature information during the spraying of the refrigerant, and when the skin surface temperature reaches the predetermined first set temperature, the notification is output through the notification module, and the laser is output through the laser module according to the reception of the user's input after the notification is output.

The laser treatment method using a cooling system, in which cooling of a patient's skin and laser irradiation on the skin are performed, disclosed in the present specification, may include: obtaining skin temperature information by detecting the patient's skin surface temperature by using the sensing unit; controlling the temperature of a refrigerant, through the refrigerant condition control unit, by applying thermal energy to the refrigerant based on the skin temperature information; spraying the refrigerant, through the nozzle, on the patient's skin surface before the laser irradiation; detecting whether the skin surface temperature reaches the predetermined first set temperature; outputting notification notifying that the skin surface temperature reaches the predetermined first set temperature by using the notification module; starting the laser irradiation on the skin through the laser module when the skin surface temperature reaches the predetermined first set temperature.

The laser treatment device having a cooling system disclosed in the present specification, the laser treatment device being used in laser therapy and having a cooling function, may include: the laser module which irradiates a patient's skin with a laser; the sensing unit which obtains the skin temperature information by detecting the patient's skin surface temperature; the cooling module including the flow rate control unit which controls the spray amount of a refrigerant sprayed on the skin based on the skin temperature information and the refrigerant condition control unit which controls the temperature of the refrigerant; and the control module which controls the cooling module such that the refrigerant is sprayed on the skin in a spraying section which at least includes a pre-cooling section which starts at time before the emitting time of the laser, wherein the cooling module controls at least one of the temperature and spray amount of the refrigerant such that the skin surface temperature is the predetermined first set temperature in at least a portion of the pre-cooling section, and the predetermined first set temperature may be preset as the temperature or more at which ice reflecting at least a portion of the laser is formed on the skin surface.

The laser treatment device having a cooling system disclosed in the present specification, which is used in laser therapy and has a cooling function, may include: the laser module which irradiates a patient's skin with a laser; the sensing unit which obtains the skin temperature information by detecting the patient's skin surface temperature; the cooling module including the flow rate control unit which controls the spray amount of cryogen, which is sprayed in the form of spray by including at least one of solid, liquid, and gas states, sprayed on the skin based on the skin temperature information, and the refrigerant condition control unit which controls the temperature of cryogen; and the control module which controls the cooling module such that the cryogen is sprayed on the skin in the spraying section which at least includes the pre-cooling section which starts at time before the emitting time of the laser and an inter-cooling section corresponding to a section in which the laser is emitted, wherein the cooling module may control at least one of the temperature and spray amount of cryogen such that the skin surface temperature is the predetermined first set temperature in the pre-cooling section and such that the skin surface temperature is a predetermined second set temperature in the inter-cooling section, and the predetermined second set temperature may be preset as a temperature or more at which the cryogen of a solid state reflecting at least a portion of the laser is formed in a path in which the laser is emitted.

The laser treatment device having a cooling system disclosed in the present specification, which is used in laser therapy and has a cooling function, may include: the laser module which irradiates the patient's skin with a laser; the sensing unit which obtains skin temperature information by detecting the patient's skin surface temperature; the cooling module which controls the gas state ratio of the sprayed cryogen by applying thermal energy to cryogen, which is sprayed in the form of spray by including at least one of solid, liquid, and gas states, sprayed on the skin based on the skin temperature information; and the control module which controls the cooling module such that the cryogen is sprayed on the skin in the spraying section which at least includes the pre-cooling section which starts at time before the emitting time of the laser, and the inter-cooling section corresponding to a section in which the laser is emitted, wherein the control module may apply thermal energy to the cryogen by using the cooling module such that the gas state ratio of the cryogen is a preset value or more in the inter-cooling section.

The laser treatment method using a cooling system disclosed in the present specification, in which the cooling of the patient's skin and the laser irradiation are performed, may include: obtaining skin temperature information by detecting the patient's skin surface temperature by using the sensing unit; applying thermal energy to cryogen, by using a thermoelectric element, which is sprayed in the form of spray by including at least one of solid, liquid, and gas states, sprayed on the skin based on the skin temperature information; irradiating a patient's skin with a laser on by using the laser module; controlling the temperature of cryogen such that the skin surface temperature is the predetermined first set temperature in the pre-cooling section which starts at time before time at which the skin is irradiated with the laser; and controlling the temperature of cryogen such that the skin surface temperature is the predetermined second set temperature, which is preset as a temperature or more at which the cryogen of a solid state reflecting at least a portion of the laser is formed in a path in which the laser is emitted, in the inter-cooling section corresponding to a section in which the laser is emitted.

The laser treatment device having a cooling system disclosed in the present specification may include: the laser module which irradiates a patient's skin with a laser; the sensing unit which measures the temperature of the skin before, during, or after the skin is heated by the laser; the nozzle which sprays a refrigerant on the skin; the refrigerant condition control unit which controls the thermal energy applied to the refrigerant by using the thermoelectric element; and the control module in which the refrigerant is controlled to be sprayed through the nozzle in the spraying section including the inter-cooling section corresponding to a section in which the laser is emitted, the pre-cooling section before the inter-cooling section, and a post-cooling section after the inter-cooling, the temperature of the refrigerant to be sprayed is controlled through the refrigerant condition control unit based on the temperature of the skin to cool the skin to a desired temperature, the desired temperature is controlled to a skin temperature corresponding to the temperature of a blood vessel at which the blood vessel under the skin does not constrict in the pre-cooling section, and the desired temperature is controlled to a skin temperature corresponding to the temperature of the blood vessel at which the blood vessel constricts in at least a portion of the post-cooling section.

The laser treatment method using a cooling system disclosed in the present specification may include: irradiating a patient's skin with a laser by the laser module; measuring the temperature of the skin, by the sensing unit, before, during, or after the skin is heated by the laser; spraying a refrigerant on the skin through the nozzle; controlling thermal energy applied to the refrigerant from the refrigerant condition control unit using a thermoelectric element; and through the control module, controlling the refrigerant to be sprayed through the nozzle in the spraying section including the inter-cooling section corresponding to a section in which the laser is emitted, the pre-cooling section before the inter-cooling section, and the post-cooling section after the inter-cooling, controlling the temperature of the refrigerant to be sprayed based on the temperature of the skin to be controlled through the refrigerant condition control unit so as to cool the skin to the desired temperature, controlling the desired temperature to be adjusted to a skin temperature corresponding to the temperature of the blood vessel at which the blood vessel under the skin does not constrict in the pre-cooling section, and controlling the desired temperature to be adjusted to a skin temperature corresponding to the temperature of the blood vessel at which the blood vessel constricts in at least a portion of the post-cooling section.

Advantageous Effects

According to the embodiment of the present specification, the sensing unit can measure the 'temperature' of the skin, which is a direct factor of skin damage, to be used when controlling the temperature of a refrigerant, thereby minimizing the possibility of the skin damage.

According to the embodiment of the present specification, the temperature or amount of the refrigerant can be precisely controlled based on the temperature of the skin measured by the refrigerant condition control unit, thereby precisely controlling a skin temperature.

According to the embodiment of the present specification, the amount of a refrigerant measured by the flow rate control unit based on the temperature of the skin can be precisely controlled, thereby precisely controlling a skin temperature.

According to the embodiment of the present specification, the spraying cooling system performs cooling before laser irradiation starts and/or during the laser irradiation, thereby minimizing skin damage by heat.

According to the embodiment of the present specification, the spraying cooling system performs cooling after laser irradiation stops, thereby minimizing skin pain.

According to the embodiment of the present specification, the spraying cooling system performs cooling with a refrigerant with optimal physical characteristics in each section such as before, during, and after the laser irradiation, thereby enabling treatment to be adaptably performed according to various treatment types and objectives.

According to the embodiment of the present specification, through a method of controlling the temperature or amount of a refrigerant by controlling a current applied to the refrigerant condition control unit, sudden pressure rise of the refrigerant can be prevented when the refrigerant is sprayed. Additionally, components of a spraying unit can be prevented from being worn by strong pressure by the spraying of the refrigerant. Additionally, the after service (AS) costs of the components due to wear thereof can be reduced.

According to the embodiment of the present specification, during laser irradiation, the error of temperature measurement by the sensing unit can be corrected or prevented, thereby minimizing the possibility of skin damage during the laser irradiation.

DESCRIPTION OF DRAWINGS

FIG. 21 is a view illustrating a method of preventing the formation of an interfering substance in the path of a laser during cooling according to the embodiment of the present specification.

MODE FOR INVENTION

Figure 1:
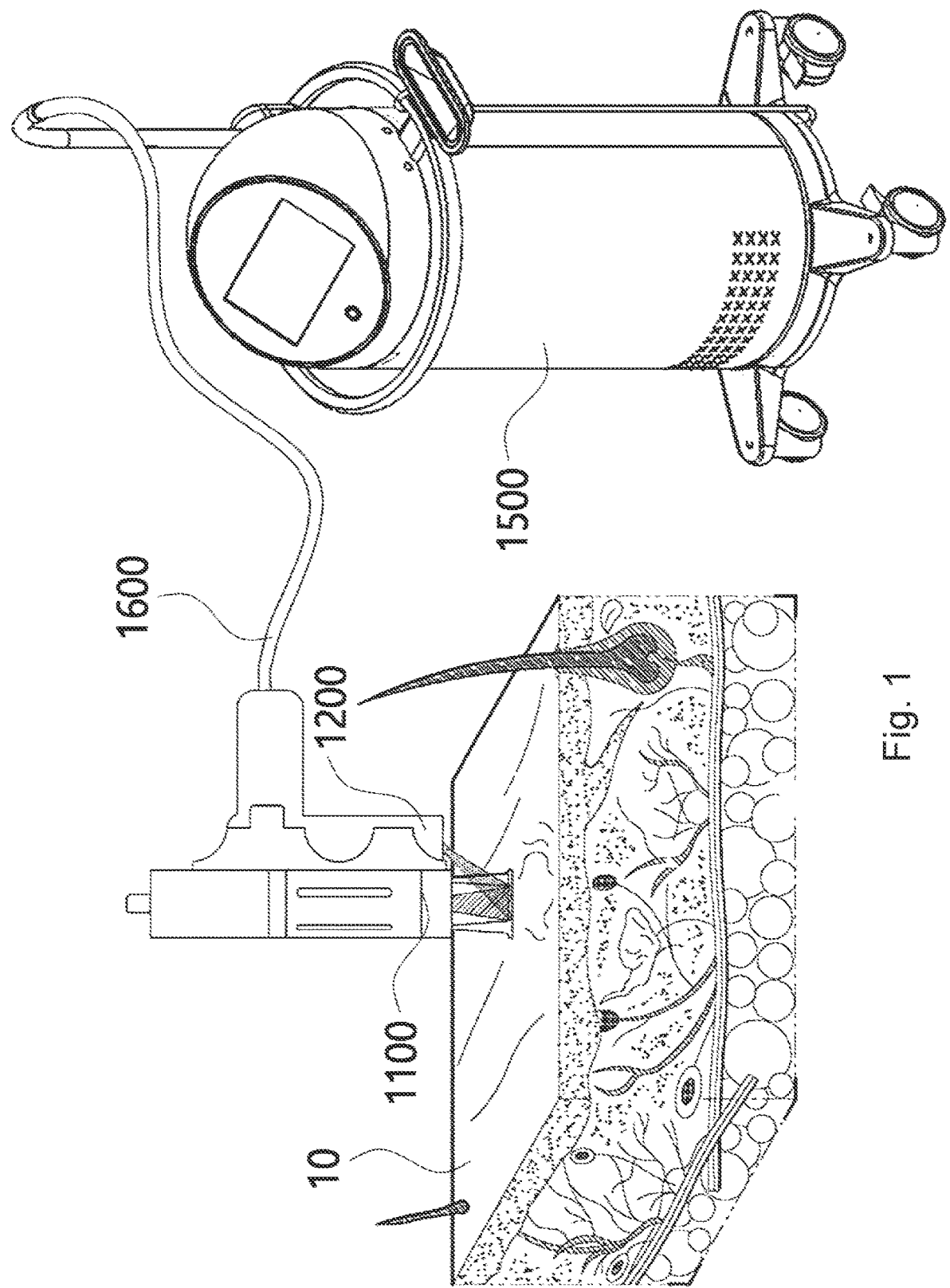
FIG. 1 is a perspective view of an exemplary embodiment of a laser treatment device disclosed in the present specification having a cooling system.

The above-described objectives, features and advantages of the present application will become more apparent through the following detailed description in conjunction with the accompanying drawings. However, the present application may have various changes and may have various embodiments, but specific embodiments will be exemplified hereinafter in the drawings and will be described in detail.

In the drawings, the thicknesses of layers and regions are exaggerated for clarity, and in addition, indicating that an element or layer is located 'on' or 'on' another component or layer may include all cases in which the element or layer is located directly on another element or layer and still another element or layer is located therebetween. Throughout the specification, like reference numerals refer to like elements in principle. In addition, components having the same function within the scope of the same idea shown in the drawings of each embodiment will be described using the same reference numerals, and overlapping descriptions thereof will be omitted.

When it is determined that a detailed description of a known function or configuration related to the present application may unnecessarily obscure the gist of the present application, the detailed description thereof will be omitted. In addition, ordinal numbers (for example, first and second, etc.) used in the description process of the present specification are only identifiers for distinguishing one component from other components.

In addition, terms 'module' and 'part' for components used in the following embodiments are given or mixed in consideration of only the ease of writing the specification, and do not have meanings or roles distinct from each other by themselves.

In the following embodiments, a singular expression includes a plural expression unless the context clearly dictates otherwise.

In the following embodiments, terms such as 'include' or 'have' mean that there are features or components described in the specification, and do not preclude the possibility that one or more other features or components may be added.

In the drawings, the size of each component may be exaggerated or reduced for convenience of description. For example, the size and thickness of each component shown in the drawings are arbitrarily indicated for convenience of description, and the present disclosure is not necessarily limited thereto.

In cases in which a certain embodiment may be realized differently, a specific process sequence may be different from the described sequence. For example, two processes described in succession may be performed substantially simultaneously, or may be performed in an order opposite to the described order.

In the following embodiments, when it is said that a film, a region, and a component are connected to each other, it includes not only a case in which the film, the region, and the component are directly connected to each other, but also a case in which other film, region, and component are placed between the film, the region, and the component such that the film, the region, and the component are indirectly connected to each other.

For example, in the present specification, when it is said that a film, a region, and a component are electrically connected to each other, it includes not only a case in which the film, region, and component is directly electrically connected to each other, but also other membrane, region, and component are placed between the film, region, and component such that the film, region, and component are indirectly electrically connected to each other.

A laser treatment device having a cooling system disclosed in the present specification may include: a laser module which irradiates a patient's skin with a laser; a sensing unit which detects a temperature of a surface of the patient's skin before, during, or after the skin is heated by the laser; a cooling module including: an inlet which receives a refrigerant from a refrigerant storage unit; a nozzle which sprays the refrigerant on the skin; a conduit which connects the inlet with the nozzle; an flow rate control unit which controls a spray amount of the refrigerant by using a valve which is positioned on the conduit and connects or disconnects the inlet with or from the nozzle; and a refrigerant condition control unit which applies a thermal energy to the refrigerant by using a thermoelectric element located between the flow rate control unit and the nozzle, the cooling module being configured to cool the surface of the skin before, during, or after the skin is heated by the laser by spraying the refrigerant; and a control module which obtains skin temperature information through the sensing unit; controls a temperature of the refrigerant to be sprayed by controlling the thermal energy applied to the refrigerant from the refrigerant condition control unit based on the skin temperature information; and controls the temperature of the skin surface to reduce damage to the skin surface being heated by the laser.

According to the embodiment of the laser treatment device having a cooling system disclosed in the present specification, the control module may control, through the flow rate control unit, a spraying section of the refrigerant to include at least a portion of an emission section of the laser; may control, through the refrigerant condition control unit, the temperature of the refrigerant to be sprayed, based on the skin temperature information in the spraying section; and may control the temperature of the skin surface to reduce the damage to the skin surface due to the laser.

According to the embodiment of the laser treatment device having a cooling system disclosed in the present specification, the refrigerant condition control unit may apply different thermal energy to the refrigerant in a section other than the laser emission section and in the laser emission section.

According to the embodiment of the laser treatment device having a cooling system disclosed in the present specification, the refrigerant condition control unit may apply less thermal energy to the refrigerant in the laser emission section than in the section other than the laser emission section.

According to the embodiment of the laser treatment device having a cooling system disclosed in the present specification, the refrigerant condition control unit may apply a first thermal energy at a first time point of a spraying section, and may apply a second thermal energy at a second time point of the spraying section, wherein the second time point may be included in a laser emission section, and the first time point may be included in a first section before the laser emission section or in a second section after the laser emission section, and the second thermal energy may be smaller than the first thermal energy.

According to the embodiment of the laser treatment device having a cooling system disclosed in the present specification, when a temperature of the skin surface at the first time point of the spraying section is lower than a temperature of the skin surface at the second time point of the laser emission section, the control module controls applying of the first thermal energy at the first time point of the spraying section and controls applying of the second thermal energy smaller than the first thermal energy at the second time point of the spraying section.

The laser treatment device having a cooling system disclosed in the present specification may include: the laser module which outputs a laser to the patient's skin for laser treatment; the sensing unit which measures the temperature of the skin; the nozzle which sprays a refrigerant on the skin; the refrigerant condition control unit which controls at least one of the temperature and spray amount of the refrigerant; and the control module configured to control at least one of the temperature and amount of the refrigerant based on at least one of first skin information and second skin information when performing the laser treatment of a second shot after the laser treatment of a first shot after obtaining at least one of the first skin information and the second skin information through the sensing unit, the first skin information including at least a skin temperature when or before the laser output of the first shot starts, and the second skin information including at least a skin temperature when or after the laser output of the first shot stops.

According to the embodiment of the laser treatment device having a cooling system disclosed in the present specification, the first skin information may include a skin temperature detected at substantially the same time as time at which the laser output starts; and the second skin information may include a skin temperature detected at substantially the same time as time at which the laser output stops, wherein when performing the laser treatment of the second shot after performing the laser treatment of the first shot, the control module may control at least one of the temperature and amount of the refrigerant in at least a portion of the laser emission section based on at least one of the first skin information and the second skin information.

According to the embodiment of the laser treatment device having a cooling system disclosed in the present specification, when performing the laser treatment of the second shot after performing the laser treatment of the first shot, the control module may control at least one of the temperature and amount of the refrigerant based on a temperature detected on a skin surface which is irradiated with a laser of the second shot in a remaining cooling section except for the laser emission section.

According to the embodiment of the laser treatment device having a cooling system disclosed in the present specification when performing the laser treatment of the second shot after performing the laser treatment of the first shot, the control module may control at least one of the temperature and amount of the refrigerant based on difference between the first skin information and the second skin information in at least a portion of the laser emission section.

According to the embodiment of the laser treatment device having a cooling system disclosed in the present specification, the laser output of the first shot and the laser output of the second shot may be performed on substantially the same position of the skin.

According to the embodiment of the laser treatment device having a cooling system disclosed in the present specification, the first shot may be a laser output to a first position of the skin, and the second shot may be a laser output to a second position of the skin.

According to the embodiment of the laser treatment device having a cooling system disclosed in the present specification, the control module may obtain a third skin information from the sensing unit, wherein the third skin information includes at least a skin temperature when or before the laser output of the second shot starts, the control module being configured to control at least one of the temperature and amount of the refrigerant based on at least one of the first skin information, the second skin information, and the third skin information when performing the laser treatment of the second shot after performing the laser treatment of the first shot.

According to the embodiment of the laser treatment device having a cooling system disclosed in the present specification, when performing the laser treatment of the second shot after performing the laser treatment of the first shot, the control module may control at least one of the temperature and amount of the refrigerant to be sprayed during the laser treatment of the second shot based on difference between the first skin information and the third skin information.

According to the embodiment of the laser treatment device having a cooling system disclosed in the present specification, the control module may adjust the temperature of a refrigerant to sprayed during the laser treatment by the second shot to be relatively high when a skin temperature included in the first skin information is higher than a skin temperature included in the third skin information than the skin temperature included in the first skin information is lower than the skin temperature included in the third skin information.

According to the embodiment of the laser treatment device having a cooling system disclosed in the present specification, the control module may control at least one of the temperature and amount of a refrigerant based on difference between the second skin information and the third skin information when the laser treatment by the second shot is performed after laser treatment by the first shot.

According to the embodiment of the laser treatment device having a cooling system disclosed in the present specification, the control module may control the temperature of a refrigerant sprayed during laser treatment in the case of a first difference to be higher than the temperature of a refrigerant sprayed during laser treatment in the case of a second difference larger than the first difference.

According to the embodiment of the laser treatment device having a cooling system disclosed in the present specification, the control module may control the amount of a refrigerant sprayed during a laser treatment in the case of the first difference to be larger than the amount of a refrigerant sprayed during a laser treatment in the case of the second difference larger than the first difference.

The laser treatment method using a cooling system disclosed in the present specification may include: irradiating a patient's skin with a laser through the laser module; measuring, through a sensing unit, a temperature of a surface of the skin before, during, or after the skin is heated by the laser; cooling the skin surface before, during, or after the skin is heated by the laser by spraying a refrigerant through the cooling module comprising: an inlet which receives the refrigerant from the refrigerant storage unit; the nozzle which sprays the refrigerant on the skin; a conduit which connects the inlet with the nozzle; the flow rate control unit which controls the spray amount of the refrigerant by using the valve which is positioned on the conduit and connects or disconnects the inlet with or from the nozzle; and the refrigerant condition control unit which applies thermal energy to the refrigerant by using the thermoelectric element located between the flow rate control unit and the nozzle; and controlling, through the control module, the temperature of the skin surface to reduce damage to the skin surface being heated by the laser by controlling the temperature of the refrigerant to be sprayed by controlling thermal energy applied to the refrigerant from the refrigerant condition control unit based on skin temperature information after obtaining the skin temperature information from the sensing unit.

The laser treatment method using a cooling system disclosed in the present specification may include: outputting a laser to a patient's skin through the laser module; measuring a temperature of the skin through the sensing unit; spraying a refrigerant on the skin through the nozzle; controlling at least one of temperature and amount of the refrigerant through the refrigerant condition control unit; obtaining at least one of the first skin information and the second skin information from the sensing unit through the control module, wherein the first skin information comprises at least a temperature of the skin when or before the laser output of the first shot starts, and the second skin information comprises at least the temperature of the skin when or after the laser output of the first shot stops; and controlling at least one of the temperature and amount of the refrigerant, through the control module, based at least one of the first skin information and the second skin information when performing a laser treatment of the second shot after performing the laser treatment of the first shot.

In the laser treatment method using a cooling system disclosed in the present specification, the first skin information may include the skin temperature detected at substantially the same time as time at which the laser output starts, and the second skin information may include comprises the skin temperature detected at substantially the same time as time at which the laser output stops, when the laser treatment of the second shot is performed after performing the laser treatment of the first shot, the control module may control at least one of the temperature and amount of the refrigerant in at least a portion of an emission section of the laser, based on at least one of the first skin information and the second skin information.

In the laser treatment method using a cooling system disclosed in the present specification, when performing the laser treatment of the second shot after performing the laser treatment of the first shot, the control module may control at least one of the temperature and amount of the refrigerant based on a temperature detected on a skin surface which is irradiated with a laser of the second shot in a remaining cooling section except for the laser emission section.

In the laser treatment method using a cooling system disclosed in the present specification, when performing the laser treatment of the second shot after performing the laser treatment of the first shot, the control module may control at least one of the temperature and amount of the refrigerant based on difference between the first skin information and the second skin information in at least a portion of the laser emission section.

According to the laser treatment method using a cooling system disclosed in the present specification, the first shot may be a laser output to the first position of the skin, and the second shot may be a laser output to the second position of the skin.

In the laser treatment method using a cooling system disclosed in the present specification, the control module may obtain a third skin information from the sensing unit, wherein the third skin information includes at least a skin temperature when or before the laser output of the second shot starts, the control module being configured to control at least one of the temperature and amount of the refrigerant based on at least one of the first skin information, the second skin information, and the third skin information when performing the laser treatment of the second shot after performing the laser treatment of the first shot.

In the laser treatment method using a cooling system disclosed in the present specification, when performing the laser treatment of the second shot after performing the laser treatment of the first shot, the control module may control at least one of the temperature and amount of the refrigerant to be sprayed during the laser treatment of the second shot based on difference between the first skin information and the third skin information.

According to the embodiment, the laser treatment device having a cooling system disclosed in the present specification may include: the laser module which irradiates the patient's skin with a laser; the sensing unit which obtains the skin temperature information by detecting the patient's skin surface temperature before the skin is heated by the laser; the cooling module including the nozzle which sprays the refrigerant on the skin surface, and the refrigerant condition control unit which controls the temperature of the refrigerant by applying thermal energy to the refrigerant; and the control module in which the skin is irradiated with a laser on through the laser module, the cooling module is controlled such that the spraying of a refrigerant on the skin is started before the laser irradiation, at least one of the spray amount and temperature of a refrigerant is controlled based on the skin temperature information during the spraying of the refrigerant, whether the skin surface temperature reaches the predetermined first set temperature is detected, and the laser irradiation is started when the skin surface temperature reaches the predetermined first set temperature.

According to the embodiment of the laser treatment device having a cooling system disclosed in the present specification, the cooling module may control the temperature of a refrigerant such that the skin surface temperature reaches a predetermined second set temperature different from the predetermined first set temperature after the laser irradiation.

According to the embodiment of the laser treatment device having a cooling system disclosed in the present specification, the cooling module may control the temperature of a refrigerant such that the skin surface temperature reaches the predetermined first set temperature in a preset section before the laser irradiation.

According to the embodiment of the laser treatment device having a cooling system disclosed in the present specification, when the laser irradiation starts, the cooling module may stop the spraying of a refrigerant on the skin surface.

According to the embodiment of the laser treatment device having a cooling system disclosed in the present specification, the cooling module may allow a refrigerant to be sprayed on the skin surface such that the skin surface temperature reaches the set temperature different from the predetermined first set temperature after the laser irradiation stops.

According to the embodiment, the laser treatment device having a cooling system disclosed in the present specification may include the trigger which receives a user's input, and when receiving the user's input, the control module may spray a refrigerant on the skin surface through the cooling module and may emit the laser through the laser module.

According to the embodiment, the laser treatment device having a cooling system disclosed in the present specification may include a first trigger which receives a user's first input commanding the cooling of the skin surface and a second trigger which receives a user's second input commanding the laser irradiation, and the control module may spray a refrigerant on the skin surface through the cooling module by receiving a user's first input, and may emit the laser through the laser module by receiving a user's second input.

According to the embodiment of the laser treatment device having a cooling system disclosed in the present specification, when a user's first input is not received and a user's second input is received, the control module may prevent a laser from being irradiated on the skin.

According to the embodiment, the laser treatment device having a cooling system disclosed in the present specification may include the trigger which receives a user's input commanding laser irradiation, and the control module may allow the laser irradiation to be performed on the skin by receiving the user's input and may prevent a laser from being irradiated on the skin when the skin surface temperature does not reach the predetermined first set temperature.

According to the embodiment of the laser treatment device having a cooling system disclosed in the present specification, the cooling module may maintain the spraying of a refrigerant on the skin surface in the spraying section, and the spraying section may include a section in which the laser module irradiates the skin surface with the laser.

According to the embodiment of the laser treatment device having a cooling system disclosed in the present specification, the control module may stop the laser irradiation when receiving a user's input when the skin surface temperature is the first desired temperature or more.

According to the embodiment of the laser treatment device having a cooling system disclosed in the present specification, the notification may include at least one of visual notification, auditory notification and tactile notification.

According to the embodiment, the laser treatment method using a cooling system disclosed in the present specification may include: obtaining the skin temperature information by detecting the patient's skin surface temperature by using the sensing unit; controlling the temperature of a refrigerant, through the refrigerant condition control unit, by applying thermal energy to the refrigerant based on the skin temperature information; spraying the refrigerant on the patient's skin surface, through the nozzle, before laser irradiation; detecting whether the skin surface temperature reaches the predetermined first set temperature; outputting notification, by the notification module, notifying that the skin surface temperature reaches the predetermined first set temperature; and starting the laser irradiation on the skin by the laser module when the skin surface temperature reaches the predetermined first set temperature.

According to the embodiment, the laser treatment device having a cooling system disclosed in the present specification may include: the laser module which irradiates a patient's skin with a laser; the sensing unit which obtains the skin temperature information by detecting the patient's skin surface temperature; the cooling module including the flow rate control unit which controls the spray amount of a refrigerant sprayed on the skin and the refrigerant condition control unit which controls the temperature of the refrigerant, based on the skin temperature information; and the control module which controls the cooling module such that the refrigerant is sprayed on the skin in the spraying section which at least includes a pre-cooling section which starts at time before the emitting time of the laser, wherein the cooling module controls at least one of the temperature and spray amount of the refrigerant such that the skin surface temperature is the predetermined first set temperature in at least a portion of the pre-cooling section, and the predetermined first set temperature may be set as a temperature or more at which a substance reflecting at least a portion of the laser is formed on the skin surface.

According to the embodiment of the laser treatment device having a cooling system disclosed in the present specification, the spraying section may include an inter-cooling section corresponding to a section in which a laser is emitted, and the cooling module may control at least one of the temperature and spray amount of the refrigerant such that a skin surface temperature is the predetermined second set temperature different from the predetermined first set temperature in the inter-cooling section.

According to the embodiment of the laser treatment device having a cooling system disclosed in the present specification, the spraying section may include a post-cooling section which starts at time after the laser irradiation, and the cooling module may control at least one of the temperature and spray amount of a refrigerant such that a skin surface temperature is a predetermined third set temperature different from the predetermined second set temperature in a post-cooling section.

According to the embodiment of the laser treatment device having a cooling system disclosed in the present specification, the predetermined third set temperature may be set as a temperature or less at which ice reflecting at least a portion of the laser is formed on the skin surface.

According to the embodiment of the laser treatment device having a cooling system disclosed in the present specification, the spraying section may include the inter-cooling section corresponding to a section in which a laser is emitted, and the control module may stop the cooling module from spraying a refrigerant on the skin surface in the inter-cooling section.

According to the embodiment of the laser treatment device having a cooling system disclosed in the present specification, the spraying section may include the post-cooling section after the inter-cooling section, and the cooling module may control at least one of the temperature and spray amount of the refrigerant such that the skin surface becomes the predetermined third set temperature different from the predetermined first set temperature in the post-cooling section.

According to the embodiment of the laser treatment device having a cooling system disclosed in the present specification, the predetermined first set temperature may be set as 0° C. or more.

According to the embodiment, the laser treatment device having a cooling system disclosed in the present specification may include: the laser module which irradiates a patient's skin with a laser; the sensing unit which obtains skin temperature information by detecting the patient's skin surface temperature; the cooling module including the flow rate control unit which controls the spray amount of cryogen, which is sprayed in the form of spray by including at least one of solid, liquid and gas states, sprayed on the skin; the refrigerant condition control unit which controls the temperature of the cryogen, based on the skin temperature information; and the control module which controls the cooling module such that the cryogen is sprayed on the skin in the spraying section which at least includes the pre-cooling section which starts at time before emitting time of the laser and the inter-cooling section corresponding to a section in which the laser is emitted, wherein the cooling module may control at least one of the temperature and spray amount of the cryogen such that the skin surface temperature is the predetermined first set temperature in the pre-cooling section, and such that the skin surface temperature is the predetermined second set temperature in the inter-cooling section, and the predetermined second set temperature may be preset as a temperature or more at which the cryogen of solid state reflecting at least a portion of the laser is formed in a path in which the laser is emitted.

According to the embodiment of the laser treatment device having a cooling system disclosed in the present specification, the predetermined second set temperature may be set as the temperature of −20° C. or more.

According to the embodiment of the laser treatment device having a cooling system disclosed in the present specification, the spraying section may include the post-cooling section which starts at time after the laser irradiation, and the cooling module may control the temperature of the cryogen such that the skin surface temperature becomes the predetermined third set temperature lower than the predetermined second set temperature in the post-cooling section.

According to the embodiment, the laser treatment device having a cooling system disclosed in the present specification may include: the laser module which irradiates a patient's skin with a laser; the sensing unit which obtains skin temperature information by detecting the patient's skin surface temperature; the cooling module which controls the gas status ratio of cryogen sprayed by applying thermal energy to cryogen, which is sprayed in the form of spray by including at least one of solid, liquid, and gas states, sprayed on the skin based on the skin temperature information; and the control module which controls the cooling module such that the cryogen is sprayed on the skin in the spraying section which at least includes the pre-cooling section which starts at time before the emitting time of the laser and the inter-cooling section corresponding to a section in which the laser is emitted, wherein the control module may apply thermal energy to the cryogen by using the cooling module such that the gas state ratio of the cryogen is a predetermined value or more in the inter-cooling section.

According to the embodiment of the laser treatment device having a cooling system disclosed in the present specification, cryogen may include carbon dioxide, and the control module may apply thermal energy to the cryogen by using the cooling module such that a droplet or dry ice included in the sprayed cryogen is a predetermined amount or less.

According to the embodiment of the laser treatment device having a cooling system disclosed in the present specification, the control module may apply thermal energy to the cryogen by using the cooling module such that the gas phase ratio of the cryogen is 90% or more in the inter-cooling section.

The laser treatment method using a cooling system disclosed in the present specification according to the embodiment may include: obtaining skin temperature information by detecting the patient's skin surface temperature by using the sensing unit; applying thermal energy to cryogen, by a thermoelectric element, which is sprayed in the form of a spray by including at least one of solid, liquid and gas states, sprayed on the skin, based on the skin temperature information; irradiating a patient's skin with a laser by using the laser module; controlling the temperature of the cryogen such that the skin surface temperature is the predetermined first set temperature in the pre-cooling section which starts at time before time at which the laser is sprayed on the skin; and controlling the temperature of the cryogen such that the skin surface temperature is the predetermined second set temperature, which is set as a temperature or more at which the solid cryogen reflecting at least a portion of the laser is formed in a path in which the laser is emitted, in the inter-cooling section corresponding to a section in which the laser is emitted.

According to the embodiment, the laser treatment device having a cooling system disclosed in the present specification may include: the laser module which irradiates a patient's skin with a laser; the sensing unit which measures the temperature of the skin before, during, or after the skin is heated by the laser; the nozzle which sprays a refrigerant on the skin; the refrigerant condition control unit which controls the thermal energy applied to the refrigerant by the thermoelectric element; and the control module in which in the spraying section including the inter-cooling section corresponding to a section in which the laser is emitted, the pre-cooling section before the inter-cooling section, and the post-cooling section after the inter-cooling, the refrigerant is controlled to be sprayed by the nozzle; the temperature of the refrigerant to be sprayed based on the temperature of the skin is controlled by the refrigerant condition control unit so as to cool the skin to reach the desired temperature; the desired temperature is controlled to a skin temperature corresponding to the temperature of a blood vessel at which the blood vessel under the skin does not constrict in the pre-cooling section; and the desired temperature is controlled to a skin temperature corresponding to the temperature of the blood vessel at which the blood vessel contracts in at least a portion of the post-cooling section.

According to the embodiment, the laser treatment device having a cooling system disclosed in the present specification may include the flow rate control unit which controls whether to perform the spraying of a refrigerant by using the valve or the spray amount of the refrigerant, and to control the skin to the desired temperature, the control module may control the spray amount of a refrigerant to be sprayed, through the flow rate control unit, based on the temperature of the skin, and in the pre-cooling section, the control module may control the desired temperature to a skin temperature corresponding to the temperature of the blood vessel at which a blood vessel under the skin does not constrict and, in at least a portion of the post-cooling section, may control the desired temperature to a skin temperature corresponding to the temperature of the blood vessel at which the blood vessel constricts.

According to the embodiment of the laser treatment device having a cooling system disclosed in the present specification, the refrigerant condition control unit may apply different thermal energy to a refrigerant in each of the pre-cooling section and the post-cooling section.

According to the embodiment of the laser treatment device having a cooling system disclosed in the present specification, the control module may control the period of opening/closing time of the flow rate control unit in the pre-cooling section and the period of opening/closing time of the flow rate control unit in the post-cooling section to be different from each other such that the amount of a sprayed refrigerant can be controlled.

According to the embodiment of the laser treatment device having a cooling system disclosed in the present specification, a skin temperature corresponding to the temperature of the blood vessel at which the blood vessel under the skin does not constrict may be a temperature within the temperature range of 18° C. or more to 40° C. or less.

According to the embodiment of the laser treatment device having a cooling system disclosed in the present specification, a skin temperature corresponding to the temperature of the blood vessel at which the blood vessel under the skin does not constrict may be a temperature within the temperature range of −10° C. or more to 2° C. or less.

According to the embodiment, the laser treatment method using a cooling system disclosed in the present specification may include: irradiating a patient's skin with a laser on through the laser module; measuring the temperature of the skin before, during, or after the skin is heated by the laser through the sensing unit; spraying a refrigerant on the skin through the nozzle; controlling thermal energy applied to the refrigerant through the refrigerant condition control unit using a thermoelectric element; and through the control module, controlling the spraying of the refrigerant through the nozzle in the spraying section including the inter-cooling section corresponding to a section in which the laser is emitted, the pre-cooling section before the inter-cooling section, and the post-cooling section after the inter-cooling, controlling the temperature of the refrigerant to be sprayed through the refrigerant condition control unit based on the temperature of the skin so as to cool the temperature of the skin to the desired temperature, controlling the desired temperature to a skin temperature corresponding to the temperature of the blood vessel at which the blood vessel under the skin does not constrict in the pre-cooling section, and controlling the desired temperature to a skin temperature corresponding to the temperature of the blood vessel at which the blood vessel constricts in at least a portion of the post-cooling section.

According to the embodiment, the laser treatment method using a cooling system disclosed in the present specification may further include controlling at least one of whether to perform the spraying of a refrigerant and the spray amount of the refrigerant through the flow rate control unit using the valve, wherein the control module may control the spray amount of a refrigerant to be sprayed based on the temperature of the skin through the flow rate control unit so as to control the temperature of the skin to the desired temperature; may control the desired temperature to a skin temperature corresponding to the temperature of the blood vessel at which the blood vessel under the skin does not constrict in the pre-cooling section; and may control the desired temperature to a skin temperature corresponding to the temperature of the blood vessel at which the blood vessel constricts in at least a portion of the post-cooling section.

According to the embodiment of the laser treatment method using a cooling system disclosed in the present specification, the refrigerant condition control unit may apply different thermal energy to a refrigerant in the pre-cooling section and the post-cooling section.

According to the embodiment of the laser treatment method using a cooling system disclosed in the present specification, the control module may control the period of opening/closing time of the flow rate control unit in the pre-cooling section and the period of opening/closing time of the flow rate control unit in the post-cooling section to be different from each other such that the amount of a refrigerant sprayed can be controlled.

According to the embodiment of the laser treatment method using a cooling system disclosed in the present specification, a skin temperature corresponding to the temperature of the blood vessel at which the blood vessel under the skin does not constrict may be a temperature within the temperature range of 18° C. or more to 40° C. or less.

According to the embodiment of the laser treatment method using a cooling system disclosed in the present specification, a skin temperature corresponding to the temperature of the blood vessel at which the blood vessel under the skin does not constrict may be a temperature within the temperature range of −10° C. or more to 2° C. or less.

The present specification relates to the laser treatment device having a cooling system and the treatment method thereof. According to the embodiment of the present specification, the laser treatment device having a cooling system may emit a laser on the target area of the skin and may cool the skin surface.

Here, the laser treatment may mean all actions in which light energy is applied to a treatment target, the light energy is converted into thermal energy for the target so as to promote skin care or skin treatment. For example, the laser treatment may mean causing heat ablation by accumulating the thermal energy of the light energy of the laser in the treatment target.

A laser used in the laser treatment may be any type of laser that can be used for skin treatment, and a long pulse laser or a short pulse laser may be used according to a treatment type.

Specifically, a laser used in the laser treatment may be determined by considering a target of the laser treatment, absorption wavelengths in surrounding tissues, and a location (e.g., depth) in the skin, etc. Regarding the wavelength of a laser, in general, as the wavelength of the laser increases, the penetration depth into the skin may increases. However, since the penetration depth is affected not only by a simple wavelength but also by the absorption rate of the target object, the laser is required to be selected by considering the absorption wavelength of the target object. Additionally, when light with high absorption rate for a surrounding substance is used, before the treatment of the target object, the laser may be absorbed by the surrounding substance, so heat may not be sufficiently applied to the target object. For example, much melanin is distributed in a shallow depth near the epidermis of the skin and absorbs a lot of light in a short wavelength band, and thus in the case of laser treatment that targets melanin, it is preferable to use a laser with a relatively short wavelength and high absorption for melanin. In addition, a laser of wavelengths below 600 nm is effectively absorbed into the capillaries, and a laser of wavelengths above 1200 nm is effectively absorbed by moisture in the skin, and thus in the case of a treatment that targets melanin, it is preferable to use light with a wavelength of 700 nm to 1100 nm. In other words, a laser used in laser treatment is required to be selected in consideration of the absorption rate of a treatment target, a location in the skin (e.g., depth), and the absorption rate of a surrounding tissue.

Additionally, a target described in the present specification means a target of a treatment. Specifically, a target area means a specific area or tissue of the skin to receive a treatment, and as a region or tissue on which thermal energy is intensively applied by a laser and treatment is performed through heat ablation, the target may be a portion of parts constituting a patient's body including the skin, internal and external tissues of a body, various cells, blood, and saliva.

Additionally, a skin surface may mean an area of a skin surface located in a laser path when a target area is irradiated with a laser. That is, the skin surface may be an area located on the upper layer of the skin rather than the target area. Additionally, the target area may be located on the skin surface, and in this case, the target area and the skin surface may refer to substantially the same area. However, when the target area is located in a different area under the skin surface, it is clear that the target area of the skin and the skin surface refer to different areas.

Additionally, the skin and a skin surface described in the present specification are described as different concepts. Specifically, the skin may be a concept that includes all of a skin surface, epidermis, dermis, and a subcutaneous tissue, whereas the skin surface, which is an external surface tissue of a body, is used as a concept meaning the upper tissue of the skin. In other words, in the present specification, the skin is used as a more comprehensive concept than the skin surface.

Additionally, 'cooling' as described in the present specification means applying cooling energy to a target to be cooled through a refrigerant and absorbing the thermal energy of the target to be cooled such that the temperature of the target to be cooled is decreased. For example, cooling is performed by applying cooling energy to a target to be cooled in a method of 'spraying' a refrigerant to the target to be cooled. For another example, cooling may apply cooling energy to a target to be cooled by applying the cooling energy to a cooling medium and 'contacting' the cooling medium with the target to be cooled. For still another example, cooling energy may be applied to a target to be cooled by 'spraying' air gas. In other words, cooling is required to be understood as a comprehensive concept including all methods (e.g., a contact type, a non-contact type (or an injection type), and an air gas injection type, etc.) that apply cooling energy to a target to be cooled. However, in the exemplary embodiment disclosed in the present specification, it is possible to cool a skin surface by spraying a refrigerant on the skin surface by a non-contact method, in particular, a spray method.

Here, 'a target to be cooled', that is, a target on which cooling is performed may vary. For example, when laser treatment for a patient is performed, a target to be cooled may be a portion of parts constituting the patient's body, including the skin, internal and external tissues of the body, various cells, blood, and saliva, etc. on which the laser treatment is performed. In other words, in the present specification, a target to be cooled is required to be understood as a comprehensive concept that includes all areas to be subjected to laser treatment. Particularly, when cooling a portion of a patient's body by spraying a refrigerant, the refrigerant is generally sprayed on a skin surface, and in this case, cooling energy may be applied not only to the skin surface but also to a skin tissue in an area inside the skin surface due to the transfer of the cooling energy. In this case, a target to be cooled is required to be understood as a comprehensive concept that includes not only the skin surface but also the skin tissue in the area inside the skin surface.

Additionally, in the present specification, 'a refrigerant' may include any substance that can apply cooling energy to a target to be cooled. For example, a refrigerant may include cryogen, a refrigerant, and a refrigerant, etc. including liquid and/or gas phases. For another example, a refrigerant may further include substances including a part of a solid phase. For example, 'a refrigerant' is required to be understood as a comprehensive concept which includes all substances including a phase or combination of phases that can apply cooling energy, such as carbon dioxide, liquid nitrogen, nitrogen dioxide, HFC-based substances, methane, PFC, SF6, cooling water, and cooling gas. In the exemplary embodiment disclosed in the present specification, a refrigerant may be carbon dioxide. However, a refrigerant is not limited thereto, and any substance that is not harmful to the skin and can lower a skin temperature may be used as a refrigerant for the laser treatment device of the present specification.

Additionally, a cooling section in which cooling is performed will be referred to as 'the spraying section' hereinafter. In temporal relationship with a laser emission section, the spraying section may include the pre-cooling section (or a cooling section before emission), the inter-cooling section (or a cooling section during emission), and the post-cooling (or a cooling section after emission). The pre-cooling section means a spraying section located before the starting time of the laser emission section on a time axis. The inter-cooling section means a spraying section overlapping at least a portion of the laser emission section on a time axis. The post-cooling section means a spraying section located after the stopping time of the laser emission section on a time axis. In other words, the spraying section is a section included at least partially in a section other than the laser emission section and in the laser emission section, and according to a temporal relationship with the laser emission section, the section other than the laser emission section may include the pre-cooling section and the post-cooling section, and the section included at least partially in the laser emission section may be the inter-cooling section. In some embodiments, the laser emission section and the inter-cooling section may be referred to as substantially the same section. For example, when cooling is continuously performed from the starting time of laser emission to the stopping time of the laser emission, the laser emission section and the inter-cooling section may be referred to as substantially the same section.

In this case, a laser may continuously emit a plurality of pulses at short time intervals (e.g., at nanosecond and microsecond time intervals). In this case, a section between the starting time of the output of a first laser pulse and the stopping time of the output of a last laser pulse may be referred to as a laser emission section. In other words, in the case of treatment in which a laser with a plurality of pulses is emitted at a nanosecond time interval and a microsecond time interval, the output of the laser of the plurality of pulses may be used to have substantially the same meaning as the laser output of 'one group', and accordingly, a laser emission section may mean a section between the starting time of the first pulse in the plurality of pulses and the stopping time of the last pulse.

Additionally, the meaning of applying cooling energy may be used to have substantially the same meaning as absorbing thermal energy from a target to be cooled. Additionally, absorbing thermal energy from a target to be cooled may have substantially the same meaning as applying negative energy to the target to be cooled. That is, applying cooling energy may be substantially the same as applying negative energy.

Similarly, applying thermal energy may be substantially the same as applying positive energy.

The laser treatment device disclosed in the present specification having a cooling system may be used for skin treatment, and specifically, may be used for skin treatment such as a vascular lesion, warts, acne, and pigmentation, and for cosmetic such as hair removal, hair loss, wrinkle removal, spot removal, and local fat reduction.

The present disclosure relates to the laser treatment device having a cooling system. According to the embodiment of the present specification, the laser treatment device having a cooling system may emit a laser on a target area of the skin, and may cool a skin surface. In this case, after cooling the skin surface, a laser may be irradiated on the target area, and during the laser irradiation, the skin surface may be simultaneously cooled, and after the laser irradiation, the skin surface may be cooled. Cooling the skin surface may be preferably performed by spraying a refrigerant.

Hereinafter, the configuration of the laser treatment device having a cooling system according to the embodiment of the present specification will be described with reference to FIGS. 1 and 2.

FIG. 1 is a perspective view showing illustrative embodiment of the laser treatment device disclosed in the present specification having a cooling system. FIG. 2 is a schematic diagram showing the embodiment of the laser treatment device 100 disclosed in the present specification having a cooling system.

According to the embodiment of the present disclosure, the laser treatment device 100 having a cooling system may include the laser module 1100, the cooling module 1200, the storage unit 1500 (or a tank), and a tube 1600 (or the conduit).

The laser module 1100 may generate a laser and may output the laser to the target area of the skin 10. The laser module 1100 may include a laser generating unit 1110 and a laser emitting unit 1120. When a voltage is applied to the laser generating unit 1110, electrons may be emitted from an electron emission source thereof, and the electrons may move according to an electric field and collide with an electrode to generate a laser. The laser emitting unit 1120 may output the laser generated from the laser generating unit 1110 toward the target area of the skin 10.

The cooling module 1200 may apply cooling energy to the skin by spraying a refrigerant on the skin. Here, the cooling module 1200 may control the cooling energy applied to the skin 10. Specifically, the cooling module 1200 may control cooling energy applied to the skin 10 by controlling the characteristics of the sprayed refrigerant. Here, the characteristics of a refrigerant may include physical characteristics such as the temperature, amount, pressure, and speed of the refrigerant. Accordingly, by controlling the physical characteristics of a refrigerant, the cooling module 1200 may prevent or minimize damage to skin surface by laser treatment. In addition, the cooling module 1200 may control the physical characteristics of a refrigerant, and may control the temperature of the refrigerant to minimize pain caused by a laser by decreasing the activity of a nociceptor.

Additionally, the cooling module 1200 may cool a skin surface temperature by using a cooling method such as a spraying-type, a contact-type, or an air gas spraying-type cooling.

In addition, the cooling module 1200 may include the flow rate control unit 1210, the refrigerant condition control unit 1220, and a spraying unit 1230.

The flow rate control unit 1210 of the cooling module 1200 may control the amount of a refrigerant supplied to the refrigerant condition control unit 1220 or the spraying unit 1230. The refrigerant condition control unit 1220 may control the temperature, pressure, and/or amount of the refrigerant to be sprayed, and the spraying unit 1230 may spray the refrigerant toward a skin surface.

The storage unit 1500 may receive refrigerants. Specifically, the storage unit 1500 may receive refrigerants in a thermodynamic state including a liquid state. In addition, the storage unit 1500 may be configured in the form of a cartridge or a tank. The storage unit 1500 may receive refrigerants more than refrigerants received in the spraying unit 1230. Through this, the storage unit 1500 may have internal pressure stably maintained and may accommodate a larger mass of refrigerants of a liquid state under the same volume than refrigerants of a gaseous state.

In FIG. 1, the storage unit 1500 is shown to be located outside the handpiece of the laser treatment device 100, but may be configured to be located inside the handpiece of the laser treatment device 100. For example, when the storage unit 1500 is configured as a tank, the storage unit 1500 may be located outside the handpiece of the laser treatment device 100, but when the storage unit 1500 is configured as a cartridge, the storage unit 1500 may be configured to be located inside the handpiece of the laser treatment device 100 according to a situation.

Additionally, the laser treatment device 100 according to the embodiment of the present specification may further include the tube 1600 which connects the storage unit 1500 with the inlet of the cooling module 1200. In addition, although not shown in FIGS. 1 and 2, components of the cooling module 1200 may be connected to each other by the tube. For example, the inlet of the cooling module 1200 and a first side of the refrigerant condition control unit 1220 may be connected to each other by a tube, and a second side of the refrigerant condition control unit 1220 and one side of the spraying unit 1230 may be connected to each other by a tube.

In addition, the laser treatment device 100 may include at least one tube. In the laser treatment device 100, the tube may be used to form a flow path for spraying a refrigerant discharged from the storage unit 1500 to the outside through the spraying unit 1230.

The laser treatment device 100 may include a tube involved in forming a flow path between the refrigerant outlet of the storage unit 1500 and the inlet of the flow rate control unit 1210. In other words, at least one tube may be arranged between the refrigerant outlet of the storage unit 1500 and the inlet of the flow rate control unit 1210.

The laser treatment device 100 may include a tube involved in forming a flow path between the outlet of the flow rate control unit 1210 and the inlet of the refrigerant condition control unit 1220 and/or between the outlet of the flow rate control unit 1210 and the outlet of the refrigerant condition control unit 1220.

The laser treatment device 100 may include a tube involved in forming a flow path between the outlet of the flow rate control unit 1210 and the inlet of the spraying unit 1230 and/or between the outlet of the flow rate control unit 1210 and the outlet of the spraying unit 1230.

The laser treatment device 100 may include a tube involved in forming a flow path between the outlet of the refrigerant condition control unit 1220 and the inlet of the spraying unit 1230, and/or between the outlet of the refrigerant condition control unit 1220 and the outlet of the spraying unit 1230.

According to the embodiment of the present specification, the laser module 1100 and the cooling module 1200 of the laser treatment device 100 may be coupled to each other in various methods. For example, the laser module 1100 and the cooling module 1200 may be configured in an add-on type. Alternatively, the laser module 1100 and the cooling module 1200 may be configured in a stand-alone type.

The stand-alone type may mean a type in which the laser treatment method according to the embodiment of the present specification can be performed without a separate external device.

The add-on type may mean a type in which the laser treatment device according to the embodiment of the present specification can perform laser treatment in cooperation with an external device. The cooling system of the add-on type may be provided in a form in which some components are excluded from the cooling system of the stand-alone type. For example, the cooling system of the add-on type may be configured by excluding the laser module. In this case, the laser treatment method according to the embodiment of the present specification may be performed when an external device emitting a laser and the cooling system of the add-on type cooperate.

Hereinafter, the cooling module 1200 described above will be described in more detail.

Referring back to FIG. 2, the cooling module 1200 may include the flow rate control unit 1210, the refrigerant condition control unit 1220, and the spraying unit 1230. Additionally, the cooling module 1200 may further include the inlet which receives a refrigerant from the storage unit 1500 which receives the refrigerant.

According to the embodiment of the present disclosure, the flow rate control unit 1210 may be configured as the valve. The valve may function to control the flow and amount of a refrigerant. The valve may function to discharge or block a refrigerant passing through the valve. Alternatively, the valve may function to control the degree of discharging a refrigerant passing through the valve.

According to the embodiment of the present disclosure, the valve may be controlled according to a specific signal. The valve may be opened and closed in response to an electronic signal generated by the control module 1400. For a specific example, the valve may be an electronic valve (e.g., a solenoid valve), but is not limited thereto.

According to the embodiment of the present disclosure, the valve may be controlled according to the mechanical structure and the movement of fluid. The valve may be opened and closed according to pressure formed by fluid moving along a flow path in the laser treatment device 100. For a specific example, the valve may be a hydraulic valve (e.g., a pressure control valve), but is not limited thereto.

According to the embodiment of the present disclosure, the valve may be controlled according to a user's input. The valve may be opened or closed by a user. For specific example, the valve may be a manual valve (e.g., a globe valve), but is not limited thereto.

For example, the flow rate control unit 1210 may be located between the inlet of the cooling module 1200 and the refrigerant condition control unit 1220. In this case, the flow rate control unit 1210 may control the amount of a refrigerant supplied to the refrigerant condition control unit 1220 from the inlet of the cooling module 1200. For example, the valve may be located between the inlet of the cooling module 1200 and the refrigerant condition control unit 1220 and may control the amount of a refrigerant supplied to the refrigerant condition control unit 1220 from the inlet of the cooling module 1200. Specifically, when the valve is opened, a refrigerant may move from the inlet of the cooling module 1200 to the refrigerant condition control unit 1220, and when the valve is closed, the refrigerant may be limited to move from the inlet of the cooling module 1200 to the refrigerant condition control unit 1220. In addition, the opening hours and cycle of the valve may be controlled to control the amount of a refrigerant which can move from the inlet of the cooling module 1200 to the refrigerant condition control unit 1220.

For another example, the flow rate control unit 1210 may be located between the refrigerant condition control unit 1220 inside the cooling module 1200 and the spraying unit 1230. In this case, the flow rate control unit 1210 may control the amount of a refrigerant supplied to the spraying unit 1230 from the refrigerant condition control unit 1220. For example, the valve may be located between the refrigerant condition control unit 1220 and the spraying unit 1230 and may control the amount of a refrigerant supplied to the spraying unit 1230 from the refrigerant condition control unit 1220. Specifically, when the valve is opened, a refrigerant may move to the spraying unit 1230 from the refrigerant condition control unit 1220, and when the valve is closed, the refrigerant may be limited to move to the spraying unit 1230 from the refrigerant condition control unit 1220. In addition, by controlling the opening hours and opening cycle of the valve, it is possible to control a refrigerant which can move to the spraying unit 1230 from the refrigerant condition control unit 1220. In other words, by controlling the opening hours of the flow rate control unit 1210, the amount of a refrigerant supplied to the spraying unit 1230 may be controlled, and finally, the amount of a refrigerant to be sprayed may be controlled to control a skin surface temperature.

For example, the flow rate control unit 1210 may be configured as the solenoid valve, and the solenoid valve is electrically connected with the control module 1400 and an input unit, and thus a signal generated by manipulating the input unit by a user is input to the control module 1400, and based on this, the control module 1400 may control the solenoid valve to be opened such that the inflow or outflow of a refrigerant can be controlled.

For example, the flow rate control unit 1210 may be configured as the solenoid valve. In this case, the solenoid valve may control the inflow or outflow of a refrigerant by adjusting the opening cycle of the valve by a pulse width modulation (PWM) method according to the electrical signal of the control module 1400. Specifically, the solenoid valve automatically performs a plurality of opening/closing operations according to a protocol preset from the control module 1400, so that the valve can be opened only for a predetermined period of time during treatment. In this case, the opening cycle of the valve maybe a regular cycle or an irregular cycle.

Referring back to FIG. 2, the cooling module 1200 of the laser treatment device 100 may include the refrigerant condition control unit 1220. The refrigerant condition control unit 1220 according to the embodiment of the present disclosure may function to control the physical state of a refrigerant. In other words, the refrigerant condition control unit 1220 may perform the function of controlling the physical state of a refrigerant in the laser treatment device 100. That is, the refrigerant condition control unit 1220 may function to control the physical state of a refrigerant moving in the cooling module 1200 including the flow rate control unit 1210 and/or the spraying unit 1230.

In an embodiment, the refrigerant condition control unit 1220 may control the temperature and/or pressure of a refrigerant. The refrigerant condition control unit 1220 may heat a refrigerant. Alternatively, the refrigerant condition control unit 1220 may cool a refrigerant. Alternatively, the refrigerant condition control unit 1220 may heat and/or cool a refrigerant according to the state of the refrigerant to maintain the temperature of the refrigerant. Alternatively, the refrigerant condition control unit 1220 may heat and/or cool a refrigerant according to the state of the refrigerant to maintain the pressure of the refrigerant.

In an embodiment, the refrigerant condition control unit 1220 may control the speed and/or pressure of a refrigerant. The refrigerant condition control unit 1220 may provide space in which a refrigerant expands and may decrease the speed and the pressure of the refrigerant. Alternatively, the refrigerant condition control unit 1220 may provide space in which the refrigerant is compressed and may increase the speed and pressure of the refrigerant.

In an embodiment, the refrigerant condition control unit 1220 may perform controlling the amount of a refrigerant. For example, when thermal energy applied to a refrigerant from the refrigerant condition control unit 1220 is increased, the degree of the freedom of the refrigerant moving through the refrigerant condition control unit 1220 is increased and thus static pressure thereof is increased such that the amount of the refrigerant is decreased. Contrarily, when thermal energy applied to a refrigerant from the refrigerant condition control unit 1220 is decreased, the degree of the freedom of the refrigerant flowing through the refrigerant condition control unit 1220 is decreased and thus static pressure thereof is decreased such the amount of the refrigerant is increased.

The refrigerant condition control unit 1220 according to the embodiment of the present disclosure may include an element capable of supplying thermal energy. The refrigerant condition control unit 1220 can generate thermal energy.

The refrigerant condition control unit 1220 may generate thermal energy by using chemical energy or by using electrical energy. In addition, the refrigerant condition control unit 1220 may generate thermal energy by using a Joule-Thomson method in which condensed gas is used.

Alternatively, the refrigerant condition control unit 1220 may supply thermal energy by using a thermoelectric element such as a Peltier element. In a case in which the refrigerant condition control unit 1220 is a thermoelectric element, when a current is applied to the thermoelectric element, due to a Peltier effect, the first surface of the thermoelectric element may absorb heat, and heat may be generated in the second surface of the thermoelectric element.

According to the embodiment of the present disclosure, the laser treatment device 100 arranged such that a surface corresponding to the second surface of the thermoelectric element is in thermal contact with a flow path in which a refrigerant flows may be provided, and in this case, the thermoelectric element may function as the refrigerant condition control unit 1220.

Referring back to FIG. 2, the cooling module 1200 of the laser treatment device 100 may include the spraying unit 1230. The spraying unit 1230 according to the embodiment of the present disclosure may function to spray fluid inside the cooling module 1200 to the outside. The spraying unit 1230 may function to discharge a refrigerant passing through the flow rate control unit 1210 and/or the refrigerant condition control unit 1220 to the outside.

The spraying unit 1230 according to the embodiment of the present disclosure may be configured as a nozzle. The nozzle may perform the function of allowing a refrigerant flowing in at least one area in the cooling module 1200 to be ejected to free space and reach the area of a skin surface. In addition, the spraying unit 1230 may be configured to include a nozzle structure in which a Joule-Thomson effect can be optimized. Specifically, the nozzle is formed to be narrower in width than a flow path through which a high-pressure refrigerant flows, and when the flow path is opened, the high-pressure refrigerant is guided along the flow path to the nozzle, and the refrigerant discharged through the nozzle may be sprayed in a cooled state due to the Joule-Thomson effect.

The refrigerant sprayed through the spraying unit 1230 is sprayed in a cooled state due to the Joule-Thomson effect. Here, the Joule-Thomson effect is a phenomenon in which the temperature of a compressed gas decreases when the compressed gas expands. The phenomenon is a change of temperature in relation to a thermodynamic phase consisting of pressure-temperature, and is a phenomenon applied to liquefying air or cooling air through a refrigerant. When inserting an aperture such as an orifice into the flow path of fluid, the temperature of the fluid is lowered behind the aperture. The phenomenon is a phenomenon in which when a gas expands freely, that is, when gas expands adiabatically without exchanging work with the outside, internal energy is almost unchanged. The phenomenon refers to the effect of adiabatic free expansion in order to obtain a low temperature with a gas liquefaction device. Due to the Joule-Thomson effect, the refrigerant sprayed through the spraying unit 1230 is cooled due to rapid pressure decrease thereof, and when the refrigerant is sprayed on a treatment area, the refrigerant takes away heat from the treatment area by coming into contact with the treatment area and thus the treatment area can be cooled.

The refrigerant ejected into free space may be in a gas, liquid and/or solid phase. In other words, a refrigerant may be in a gas phase, a liquid phase, or a solid phase and may be a mixture in which refrigerants of at least two or more phases are distributed together. In an example, when a refrigerant is carbon dioxide ($CO_2$), the refrigerant sprayed may be distributed as a mixture of gas and solid. In another example, when a refrigerant is nitrogen ($N_2$), the refrigerant sprayed may be distributed as a mixture of gas and liquid.

Additionally, the nozzle may have wear-resistant properties. In other words, the nozzle may be formed of a substance that is less prone to friction damage. For example, the nozzle may be made of an aluminum alloy, steel alloy, stainless steel, or a copper alloy, but is not limited thereto.

Additionally, according to the embodiment of the present disclosure, the spraying unit 1230 may further include a spray limitation part to limit an area of a skin surface which a refrigerant discharged from the spraying unit 1230 reaches. In addition, the spraying unit may further include a guide part such that a refrigerant does not reach an area other than the spray limitation part.

Referring back to FIG. 2, according to the embodiment of the present disclosure, the laser treatment device 100 may include the sensing unit 1300. The sensing unit 1300 may detect a skin surface temperature, a refrigerant temperature, and temperature of components of the cooling module 1200, or any suitable combination thereof.

The sensing unit 1300 may include a first temperature sensing unit which measures the temperature of a skin surface.

Additionally, the sensing unit 1300 may include the second temperature sensing unit which measures the temperature of the refrigerant condition control unit 1220 and/or thermal energy applied to a refrigerant from the refrigerant condition control unit 1220.

Additionally, the sensing unit 1300 may include a third temperature sensing unit which measures the temperature of a refrigerant to be sprayed from the spraying unit 1230.

The first temperature sensing unit may measure the temperature of an area of a skin surface on which a laser will be irradiated, an area of a skin surface on which a laser is being irradiated, or an area of a skin surface on which laser irradiation is completed. The first temperature sensing unit may preferably measure the temperature of the center of a target area (e.g., an area of a skin surface in the laser path) of the skin surface. The first temperature sensing unit may be configured to measure an area other than the center of the target area of the skin surface, but the temperature of the center of the target area is increased the most by a laser output, and thus is more likely to reach a skin damage temperature, and thus it is possible to minimize the possibility of skin damage by measuring the temperature of the center of the target area of the skin surface.

In this case, the first temperature sensing unit may be configured as a non-contact temperature sensing unit. According to the embodiment of the present disclosure, a spacing distance between the laser treatment device 100 and a skin surface may be changed, and in this case, the angle of the non-contact temperature sensing unit may be adjusted such that the non-contact temperature sensing unit measures the center of a target area of the skin surface according to the spacing distance. For example, the laser treatment device 100 of the present disclosure may further include a cooling distance maintenance part by which a distance between the laser treatment device and a skin surface can be adjusted to a plurality of distances (e.g., 1 cm, 2 cm, and 3 cm). In this case, the cooling distance maintenance part is mechanically interlocked with the non-contact temperature sensing unit, and thus the installation angle of the non-contact temperature sensing unit is adjusted such that the center of the target area of the skin surface is examined according to a distance preset by the cooling distance maintenance part.

The second temperature sensing unit may measure the temperature of the refrigerant condition control unit 1220 and/or thermal energy applied to a refrigerant from the refrigerant condition control unit 1220. For an example, in a case in which the refrigerant condition control unit 1220 is a thermoelectric element such as a Peltier element, when a current is applied to the thermoelectric element, due to a Peltier effect, the first surface of the thermoelectric element may absorb heat, and heat may be generated in the second surface of the thermoelectric element. In this case, according to a current applied to the thermoelectric element, thermal energy generated or absorbed in the thermoelectric element is different, and thus the second temperature sensing unit may be configured to measure the temperature of at least one of the first surface and second surface of the thermoelectric element. Since the thermal energy generated or absorbed in the refrigerant condition control unit 1220 is one of direct variables in the control of the temperature of the target area of a skin surface, the temperature of the refrigerant condition control unit 1220 may be measured such that data by which the temperature of the target area of the skin surface can precisely be controlled can be obtained.

However, this is only an example, and the refrigerant condition control unit 1220 may measure the amount of thermal energy applied to a refrigerant based on information about a current value obtained by measuring a current applied to the thermoelectric element and the temperature of the refrigerant measured by the third temperature sensing unit to be described later.

The third temperature sensing unit may be configured to measure the temperature of a refrigerant sprayed by the spraying unit 1230. Since the temperature of the refrigerant sprayed by the spraying unit 1230 is one of direct variables in the control of the temperature of a target area of a skin surface, the temperature of the refrigerant sprayed by the spraying unit 1230 is measured such that data by which the temperature of the target area of the skin surface can be precisely controlled can be obtained. However, the third temperature sensing unit is not limited to the temperature of a refrigerant sprayed by the spraying unit 1230, and it is clear that even if the third temperature sensing unit is configured to measure the temperature of a refrigerant flowing through a flow path at any position inside the cooling module 1200 of the laser treatment device 100, the objective of the present disclosure for precisely controlling the temperature a target area of a skin surface can be obtained.

Referring back to FIG. 2, the laser treatment device 100 according to the embodiment of the present disclosure may include the control module 1400. In this case, the control module 1400 may further include a memory in which existing treatment information, temperature information such as the temperature of a refrigerant and a skin surface temperature, and treatment protocol information are stored.

The control module 1400 according to the embodiment of the present disclosure may control the overall operation of the laser treatment device 100. For example, the control module 1400 may load and execute a program for the operation of the cooling module 1200 from the memory, may generate a control signal for controlling a laser emitted by the laser emitting unit 1120, or may receive a triggering signal from a user through the input unit and transmit the triggering signal to the laser module 1100, the cooling module 1200, and the sensing unit 1300.

The control module 1400 according to the embodiment of the present disclosure may control the operation of the laser treatment device 100. For example, the control module 1400 may control the emission of a laser by the laser module 1100 of the laser treatment device 100. In addition, the control module 1400 may allow the physical characteristics of a refrigerant to be controlled by the cooling module 1200 of the laser treatment device 100 and may control the refrigerant to be sprayed. In addition, the control module 1400 may control the sensing unit 1300 of the laser treatment device 100 to detect a skin surface temperature and the temperature of a refrigerant.

The control module 1400 according to the embodiment of the present disclosure may control the operation of the laser generating unit 1110 and the laser emitting unit 1120 of the laser module 1100.

The control module 1400 according to the embodiment of the present disclosure may control the driving of the flow rate control unit 1210. For a more specific example, the control module 1400 may control the opening/closing of the flow rate control unit 1210, and may control the opening/closing of the flow rate control unit 1210 to have a repeating cycle when required.

Additionally, the control module 1400 may control the period of opening/closing time of the flow rate control unit 1210. Through this, the control module 1400 may control the amount of a refrigerant supplied to the spraying unit 1230 and may control the amount of cooling energy applied to a target area of a skin surface.

The control module 1400 according to the embodiment of the present disclosure may control the operation of the refrigerant condition control unit 1220. For example, the control module 1400 may control whether to operate the refrigerant condition control unit 1220 (e.g., whether to turn on/off the refrigerant condition control unit 1220), and may control the turning on/off of the refrigerant condition control unit 1220 in consideration of the relation of the refrigerant condition control unit with the opening/closing of the flow rate control unit 1210 (e.g., the valve) when required. Particularly, when the refrigerant condition control unit 1220 is the thermoelectric element (e.g., a Peltier element), the control module 1400 may control the amount of a current applied to the thermoelectric element. Through this, the degree of the heat absorption of the first surface of the thermoelectric element and the degree of the heat generation of the second surface thereof may be controlled, and thus the amount of thermal energy applied to a refrigerant by the thermoelectric element can be controlled.

Here, the increase of the amount of thermal energy applied to a refrigerant from the refrigerant condition control unit 1220 (e.g., the thermoelectric element) may be substantially the same as the increase of the temperature of a refrigerant flowing through a flow path inside the refrigerant condition control unit 1220, and the decrease of the amount of thermal energy applied to a refrigerant from the refrigerant condition control unit 1220 (e.g., the thermoelectric element) may be substantially the same as the decrease of the temperature of a refrigerant flowing through a flow path inside the refrigerant condition control unit 1220.

According to another embodiment of the present disclosure, by reversing the direction of the current applied to the thermoelectric element, the control module 1400 may control heat to be generated on the first surface of the thermoelectric element and may control heat to be absorbed on the second surface of the thermoelectric element. In this case, a refrigerant flowing through the refrigerant condition control unit 1220 may be 'cooled' by the heat absorption of the second surface of the thermoelectric element. Accordingly, when the thermoelectric element is applied to the refrigerant condition control unit 1220, the control module 1400 may control the direction of a current applied to the thermoelectric element and may heat or cool the refrigerant flowing through the refrigerant condition control unit 1220.

Figure 2:
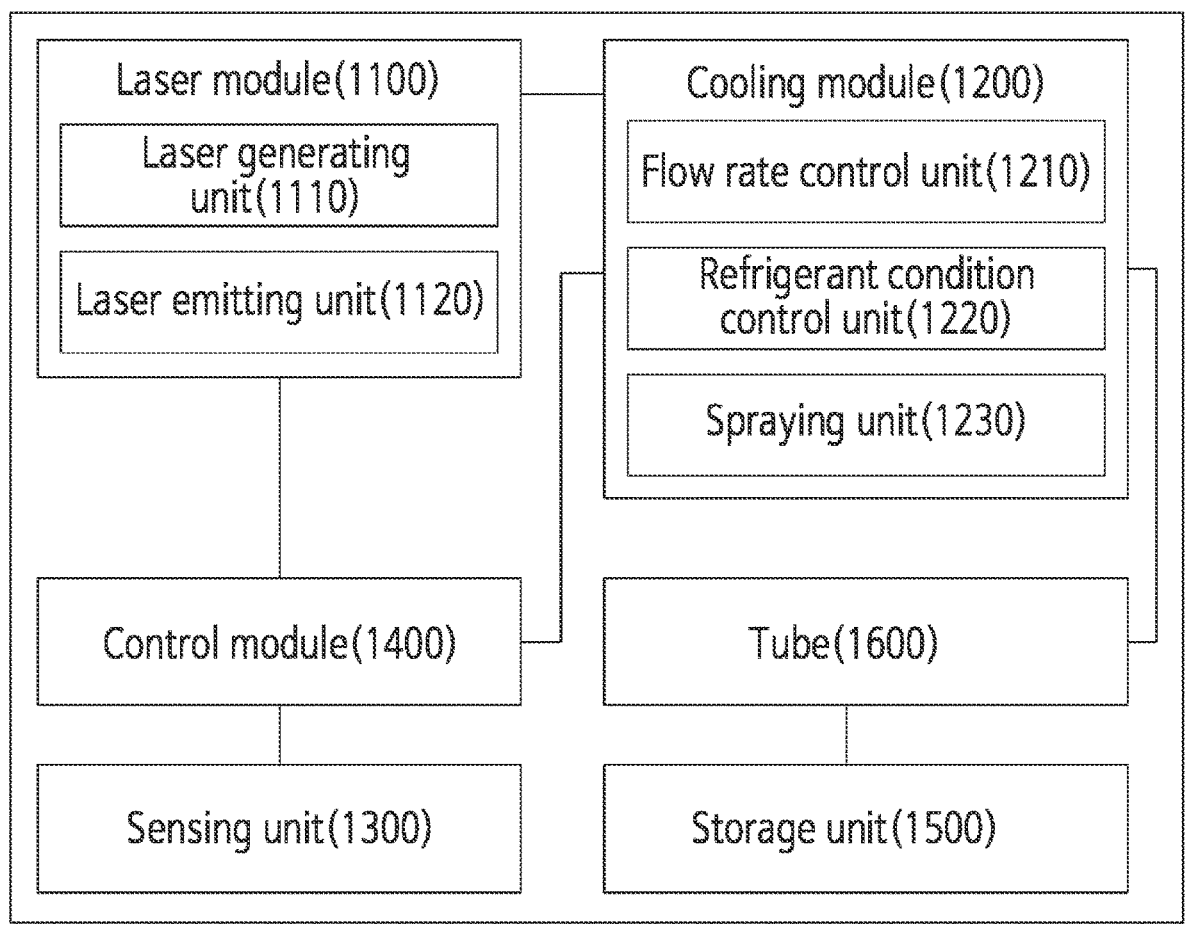
FIG. 2 is a schematic diagram of the embodiment of the laser treatment device disclosed in the present specification having a cooling system.

As illustrated in FIG. 2, the common control module 1400 is illustrated to control the laser module 1100 and the cooling module 1200, but is not limited thereto, and the laser treatment device 100 may include a plurality of control modules and may be configured such that a first control module of the plurality of control modules controls the operation of the laser module 1100, and a second control module of the plurality of control modules controls the operation of the cooling module 1200. In this case, the first control module and the second control module may be electrically connected to each other and may respectively control laser emission and refrigerant spray to be performed by considering connection between the laser module 1100 and the cooling module 1200.

The control module 1400 may be configured as a central processing unit (CPU) or a device similar thereto according to hardware or software or a combination thereof. For example, the control module 1400 may be configured as a controller or a processor. The control module 1400 may be provided in the form of an electronic circuit as hardware that performs a control function by processing electrical signals, and may be provided in the form of a program or code as software for driving a hardware circuit.

So far, the components of the laser treatment device 100 according to the embodiment of the present disclosure have been described. However, the laser treatment device 100 of the present disclosure is not required to include only the above components, and although not shown, may further include the input unit for receiving a user's input, an output unit such as a display for outputting specific information to a user, and a filter for filtering out impurities of a refrigerant flowing through the laser treatment device 100.

Additionally, the laser treatment device 100 may have a separate power source or may receive power from the outside by wire or wirelessly, and may have a separate switch for controlling the power source.

Hereinafter, connection relations between the components of the laser treatment device 100 according to the embodiment of the present disclosure and the specific operation of the laser treatment device 100 will be described in detail.

Figure 3:
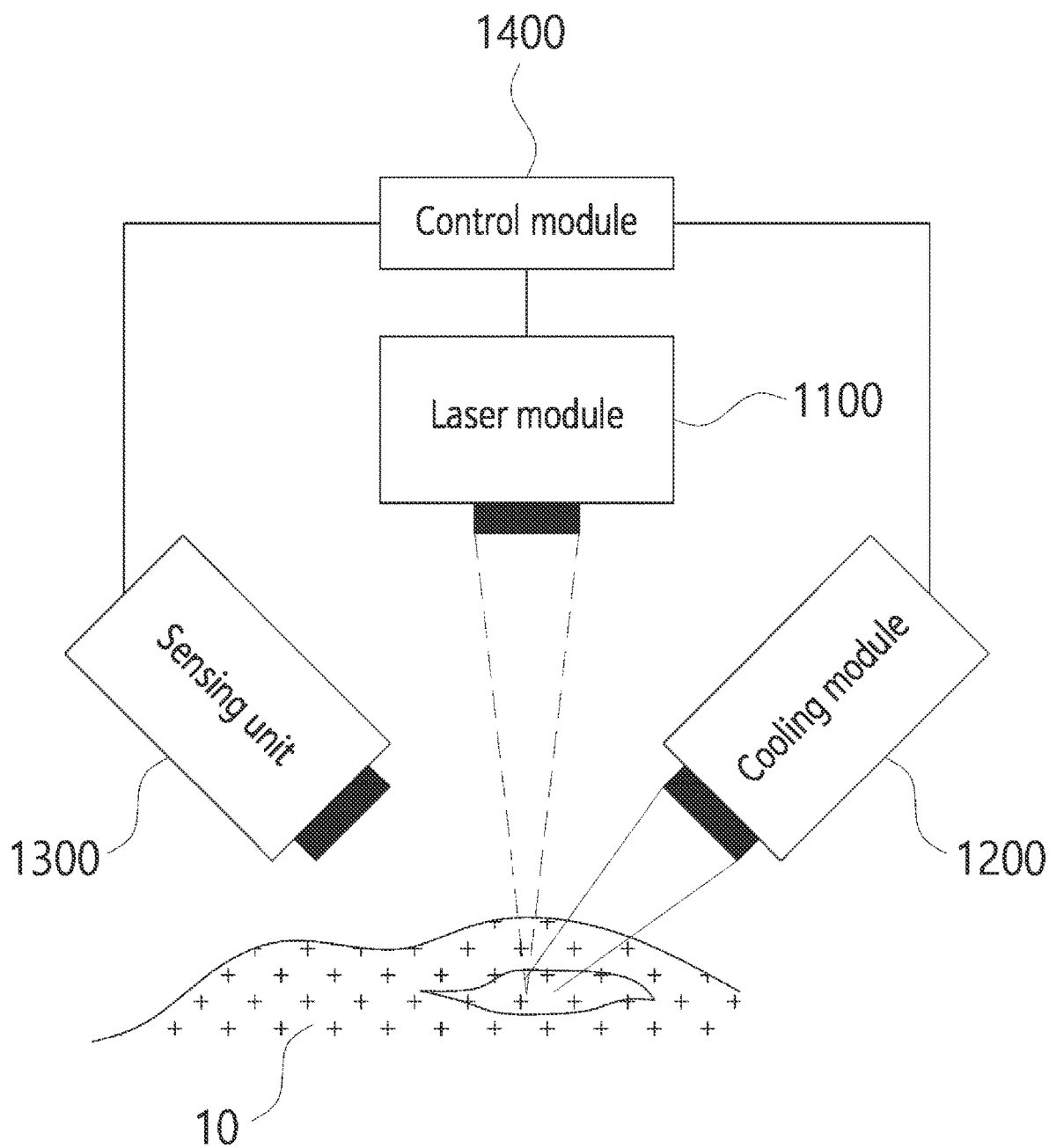
FIG. 3 is a schematic diagram illustrating the operation of the laser treatment device disclosed in the present specification having a cooling system according to the embodiment.

Hereinafter, description will be made with reference to FIG. 3. FIG. 3 is a schematic diagram illustrating the operation of the laser treatment device 100 disclosed in the present specification having a cooling system according to the embodiment. The laser module 1100 may emit a laser on the target of the skin 10, and the cooling module 1200 may spray a refrigerant on the target of the skin 10 and an area including a skin surface. In FIG. 3, when a laser is output from the laser module 1100, a refrigerant is sprayed by the cooling module 1200, but this is not restrictive, and the cooling module 1200 may spray a refrigerant before a laser is output, or after the outputting of the laser stops.

Additionally, the sensing unit 1300 can measure the skin surface temperature according to the emission of a laser and/or the spraying of a refrigerant. Additionally, the sensing unit 1300 can measure the change of the skin surface temperature according to the emission of a laser and/or the spraying of a refrigerant.

Additionally, each of the laser module 1100, the cooling module 1200, and the sensing unit 1300 may be electrically connected to the control module 1400 so as to transmit or receive an electrical signal to or from the control module 1400. The control module 1400 may control the operations of the laser module 1100, the cooling module 1200, and the sensing unit 1300 through the electrical signal.

The control module 1400 according to the embodiment of the present disclosure may control the first temperature sensing unit of the sensing unit 1300 to control the temperature of a skin surface which is the path of a laser when the laser module 1100 irradiates a target area with the laser. In this case, the first temperature sensing unit of the sensing unit 1300 may measure a skin surface temperature before, during, and after the laser irradiation, and a detected skin surface temperature may be transmitted to the control module 1400.

For example, the control module 1400 and the first temperature sensing unit of the sensing unit 1300 may be electrically connected to each other, and a skin surface temperature measured by the first temperature sensing unit may be transmitted to and stored in the control module 1400.

The refrigerant condition control unit 1220 of the laser treatment device 100 according to the embodiment of the present disclosure may control the temperature and/or pressure and/or amount of a refrigerant to be sprayed. In this case, the refrigerant condition control unit 1220 may control the temperature and/or pressure of the refrigerant by controlling the thermal energy applied to the refrigerant. In this case, the sensing unit 1300 may further include the second temperature sensing unit which measures the degree of the thermal energy applied to the refrigerant from the refrigerant condition control unit 1220. The second temperature sensing unit may measure the change amount of the temperature of the refrigerant condition control unit 1220 or the change amount of the temperature of a refrigerant passing through the refrigerant condition control unit 1220 (e.g., the change amount of the temperature of a refrigerant between the inlet and outlet of the refrigerant condition control unit 1220) and may measure the degree of the thermal energy applied to the refrigerant. However, without being limited thereto, the objective of measuring the degree of the thermal energy applied to the refrigerant from the refrigerant condition control unit 1220 may be achieved even by the method of measuring the intensity of a current applied to the refrigerant condition control unit 1220.

In this case, the temperature (e.g., temperatures of the first and second surfaces of the thermoelectric element) of the refrigerant condition control unit 1220 detected by the second temperature sensing unit, or temperature information about the change amount of the temperature of a refrigerant passing through the refrigerant condition control unit 1220 may be transmitted to the control module 1400.

For example, the control module 1400 and the second temperature sensing unit of the sensing unit 1300 may be electrically connected to each other, and temperature information measured by the second temperature sensing unit may be transmitted to and stored in the control module 1400.

Additionally, the spraying unit 1230 of the laser treatment device 100 according to the embodiment of the present disclosure may spray a refrigerant. In this case, the spraying unit 1230 may be configured such that a sprayed refrigerant can be sprayed by having the temperature and amount of the refrigerant controlled by the refrigerant condition control unit 1220 and/or the flow rate control unit 1210. In this case, the sensing unit 1300 may include the third temperature sensing unit which can measure the temperature of the refrigerant sprayed by the spraying unit 1230, and the temperature of the refrigerant detected by the third temperature sensing unit may be transmitted to the control module 1400.

For example, the control module 1400 and the third temperature sensing unit of the sensing unit 1300 may be electrically connected to each other, and the temperature information of a sprayed refrigerant detected by the third temperature sensing unit may be transmitted to and stored in the control module 1400.

The control module 1400 according to the embodiment of the present disclosure may control the period of opening/ closing time of the flow rate control unit 1210 or a current applied to the refrigerant condition control unit 1220 based on pieces of temperature information, received and stored in the control module 1400, detected by the first temperature sensing unit to the third temperature sensing unit.

The control module 1400 according to the embodiment of the present disclosure may be electrically connected to the flow rate control unit 1210, and the control module 1400 may precisely control the amount of a supplied refrigerant by controlling the opening/closing cycle or the period of opening/closing time of the flow rate control unit 1210 based on temperature data detected by the first temperature sensing unit to the third temperature sensing unit. In addition, data about the opening/closing cycle and period of opening/closing time of the flow rate control unit 1210 may be measured by a timer, and data about the opening/closing cycle and period of opening/closing time of the flow rate control unit 1210 measured by the timer may be transmitted to and stored in the control module 1400. The opening/closing cycle and period of opening/closing time of the flow rate control unit 1210 stored in the control module 1400, in combination with the skin surface temperature or/and the temperature of the refrigerant, may be a basis for controlling the temperature and/or amount of a refrigerant to be sprayed. The control module 1400 may control the temperature and/or amount of a refrigerant to be sprayed based on the data about the opening/closing cycle and period of opening/closing time of the flow rate control unit 1210 and the skin surface temperature and the temperature of the refrigerant.

Additionally, the control module 1400 according to the embodiment of the present disclosure may be electrically connected to the refrigerant condition control unit 1220, and the control module 1400 may be configured to control the thermal energy applied to the refrigerant from the refrigerant condition control unit 1220 and/or the amount of a refrigerant passing through the refrigerant condition control unit 1220 based on temperature data detected by the first temperature sensing unit to the third temperature sensing unit. In addition, information about the thermal energy applied to the refrigerant from the refrigerant condition control unit 1220 may be measured by the second temperature sensing unit, and the information about the thermal energy, measured by the second temperature sensing unit, applied to the refrigerant from the refrigerant condition control unit 1220 may be transmitted to and stored in the control module 1400. The information about the thermal energy, stored in the control module 1400, applied to the refrigerant from the refrigerant condition control unit 1220, in combination with the skin surface temperature or/and the temperature of the refrigerant, may be a basis for controlling the temperature and/or amount of a refrigerant to be sprayed later. In other words, the control module 1400 may control the temperature and/or amount of a refrigerant to be sprayed based on information about the thermal energy applied to the refrigerant from the refrigerant condition control unit 1220, the skin surface temperature, and the temperature of the refrigerant.

The control module 1400 according to the embodiment of the present disclosure may control the thermal energy applied to the refrigerant from the refrigerant condition control unit 1220 and/or the period of opening/closing time, opening/closing cycle, and opening/closing of the flow rate control unit 1210. Through this, the control module 1400 may control 'the skin surface temperature' by controlling the amount of a sprayed refrigerant. In this case, the control module 1400 may control the temperature of a refrigerant to be sprayed by using the existing information of the skin surface temperature detected by the first temperature sensing unit and stored in the control module 1400, and the information of temperature detected by at least one of the second and third temperature sensing units and stored in the control module 1400. Additionally, the control module 1400 may control the spraying unit 1230 to spray the refrigerant of a controlled temperature toward the skin surface so as to control 'the skin surface temperature'.

For example, the temperature of a refrigerant sprayed by using temperature information based on the degree of thermal energy applied to a refrigerant from the refrigerant condition control unit 1220 may be stored in the control module 1400 every treatment. Additionally, the information of the skin surface temperature controlled according to the temperature of the sprayed refrigerant may also be stored in the control module 1400. In other words, the control module 1400 may store and analyze information about the degree of thermal energy applied to the refrigerant from the refrigerant condition control unit 1220 to control the skin surface temperature to a specific temperature by using the stored temperature information. The control module 1400 according to the embodiment of the present disclosure may control the temperature of 'a refrigerant' by using the temperature information described above to control the skin surface temperature.

Additionally, the control module 1400 of the laser treatment device 100 according to the present specification may control the thermal energy applied to the refrigerant and/or the period of opening/closing time of the flow rate control unit 1210 by considering whether the laser emission section and the spraying section of a refrigerant overlap.

For example, in the case of a pre-cooling before laser emission, the control module 1400 receives the skin surface temperature information from the sensing unit 1300 and may control the temperature of a refrigerant sprayed before the starting time of the laser emission through the control of thermal energy applied to the refrigerant from the refrigerant condition control unit 1220 such that the skin surface temperature is controlled to a critical temperature or less at which the skin surface is damaged in 'the laser emission section'. In this case, the control module 1400 may control the temperature of a sprayed refrigerant in the pre-cooling section P1 such that the skin surface temperature is the critical temperature or less at which the skin surface is damaged by considering the increased value of the skin surface temperature by the laser in the laser emission section.

Additionally, in a section in the laser emission is performed, the control module 1400 may receive the information of a skin surface temperature caused by the laser emission from the sensing unit 1300, and may control the temperature of a sprayed refrigerant in the laser emission section through the control of thermal energy applied to a refrigerant from the refrigerant condition control unit 1220. In this case, the temperature of the refrigerant may be controlled by the control module 1400 such that the skin surface temperature caused by the laser emission is controlled to the critical temperature or less at which the skin surface is damaged.

Additionally, in the case of the post-cooling after a laser is emitted, the control module 1400 may receive the skin surface temperature information from the sensing unit 1300 and may control the temperature of a refrigerant sprayed after the stopping time of the laser emission section through the control of thermal energy applied to the refrigerant from the refrigerant condition control unit 1220. In this case, the control module 1400 may control the temperature of the refrigerant to be controlled to a temperature so as to minimize the pain of the skin 10.

Figure 4:
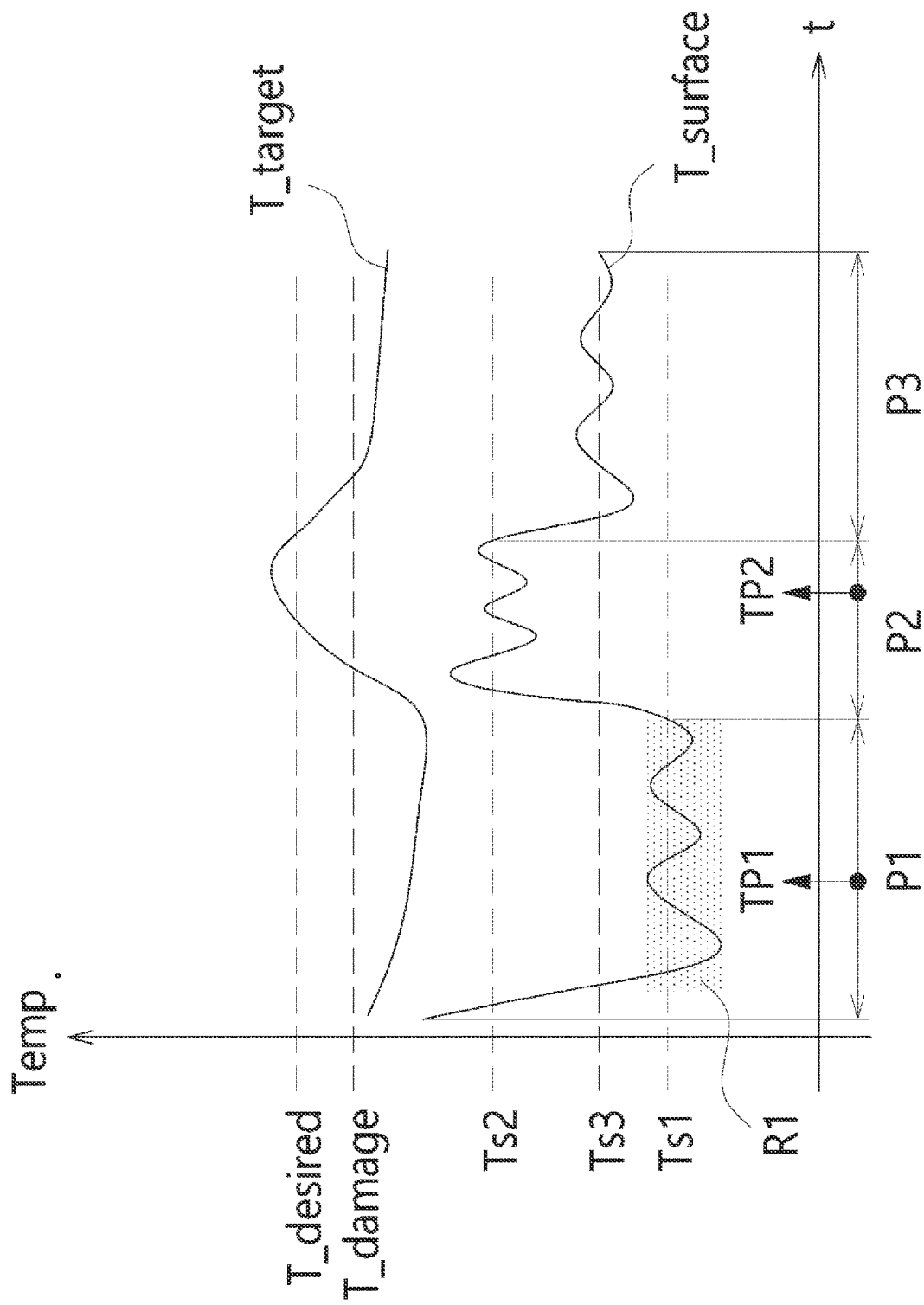
FIG. 4 is a graph illustrating changes in a skin surface temperature and the temperature of a target controlled according to the exemplary embodiment of the driving method of the laser treatment device disclosed in the present specification.

FIG. 4 is a graph illustrating changes in the skin surface temperature and the temperature of a target controlled according to the exemplary embodiment of the driving method of the laser treatment device 100 disclosed in the present specification. Here, 'T_surface' of FIG. 4 may refer to the skin surface temperature of the present specification. In addition, 'T_target' of FIG. 4 may refer to the temperature of a target of the present specification. In addition, 'T_damage' of FIG. 4 may refer to the skin damage temperature of the present specification. In addition, 'T_desired' of FIG. 4 may refer to the desired temperature of a target of the present specification. In addition, 'P1', 'P2', and 'P3' of FIG. 4 may respectively refer to 'the pre-cooling section', 'the inter-cooling section', and 'the post-cooling section' of the present specification. Additionally, 'Ts1', 'Ts2', and 'Ts3' of FIG. 4 may respectively refer to 'the first set temperature', 'the second set temperature', and 'the third set temperature' of the present specification.

According to the embodiment of the laser treatment device disclosed in the present specification 100, the control module 1400 may control the spraying section of a refrigerant to include at least a portion of the laser emission section through the flow rate control unit 1210. For example, in FIG. 4, the spraying section of a refrigerant includes the pre-cooling section P1, the inter-cooling section P2 of the laser emission section, and the post-cooling section P3, and the inter-cooling section P2 may include at least a portion of the laser emission section, and may be substantially the same section as the laser emission section.

Additionally, the control module 1400 may control the temperature of a refrigerant to be sprayed, through the refrigerant condition control unit 1220, based on the skin temperature information (e.g., the skin surface temperature and the temperature of a target, etc.) of the spraying section of a refrigerant. Through this, the skin surface temperature may be controlled such that damage to the skin surface by a laser is reduced. For example, referring to FIG. 4, a second set temperature Ts2 may be preset such that the skin surface temperature of the laser emission section is controlled to the skin damage temperature or less, and accordingly, the refrigerant may be sprayed by having the temperature of the refrigerant controlled through the refrigerant condition control unit 1220.

According to the embodiment of the laser treatment device disclosed in the present specification 100, through the flow rate control unit 1210, the control module 1400 may control the spraying section of a refrigerant to include at least a portion of the laser emission section. In this case the refrigerant condition control unit 1220 may apply different thermal energy to a refrigerant in the spraying section (e.g., the pre-cooling section P1 and/or the post-cooling section P3) other than the laser emission section of the refrigerant and in the spraying section of the laser emission section.

For example, referring to FIG. 4, the spraying section may include the pre-cooling section P1, the inter-cooling section P2 (the laser emission section), and the post-cooling section P3, and particularly, the inter-cooling section P2 may be controlled to include at least a portion of the laser emission section. In this case, thermal energy applied to the refrigerant from the refrigerant condition control unit 1220 in the laser emission section, and thermal energy applied to the refrigerant from the refrigerant condition control unit 1220 in the spraying section other than the laser emission section, for example, the pre-cooling section P1 and/or the post-cooling section P3 may be different from each other.

According to the embodiment of the laser treatment device disclosed in the present specification 100, difference between the skin surface temperature and the skin damage temperature in the laser emission section may be smaller than difference between the skin surface temperature and the skin damage temperature in a section other than the laser emission. Accordingly, the thermal energy applied to the refrigerant from the refrigerant condition control unit 1220 in the laser emission section may be smaller than the thermal energy applied to the refrigerant from the refrigerant condition control unit 1220 in the section other than the laser emission section. In other words, the temperature of a sprayed refrigerant in the laser emission section may be lower than the temperature of a sprayed refrigerant in the section other than the laser emission section.

For example, referring to FIG. 4, thermal energy applied to a refrigerant from the refrigerant condition control unit 1220 in the laser emission section may be smaller than thermal energy applied to a refrigerant from the refrigerant condition control unit in a section other than the laser emission section (for example, the pre-cooling section P1 and the post-cooling section P3). In other words, since the temperature rise of the skin 10 by a laser output may be higher in the laser emission section than in the section other than the laser emission section, the thermal energy applied to the refrigerant from the refrigerant condition control unit 1220 may be controlled to be smaller in the laser emission section than in the spraying section other than the laser emission section such that the temperature of the refrigerant to be sprayed can be controlled to be lower in the laser emission section.

However, the above description is only illustrative, and whether or not it is under the laser emission section, the thermal energy applied to the refrigerant from the refrigerant condition control unit 1220 may be controlled based on difference between the skin surface temperature measured by the sensing unit 1300 and the skin damage temperature.

According to the embodiment the laser treatment device 100 disclosed in the present specification, the spraying section may include the first time point TP1 and the second time point TP2. The first time point TP1, which is a time point in the spraying section, may be a time point included in the first section (e.g., the pre-cooling section P1) before the laser emission section or in the second section (e.g., the post-cooling section P3) after the laser emission section. The second time point TP2 may be a time point included in the laser emission section. In this case, the refrigerant condition control unit 1220 applies the first thermal energy to the refrigerant at the first time point TP1 of the spraying section, and applies the second thermal energy to the refrigerant at the second time point TP2 of the laser emission section, and the second thermal energy may be smaller than the first thermal energy.

For example, referring to FIG. 4, the first time point TP1 may be a time point included in the pre-cooling section P1 of the spraying section, and the second time point TP2 may be a time point included in the inter-cooling section P2 of the laser emission section and spraying section. In this case, since temperature rise is caused by the laser emission in the second time point TP2, the temperature of a sprayed refrigerant may be controlled to be relatively lower in the spraying section of the laser emission section by controlling the thermal energy applied to the refrigerant from the refrigerant condition control unit 1220 to be larger in the first time point TP1 than in the second time point TP2.

According to the embodiment the laser treatment device 100 disclosed in the present specification, the spraying section may include the first time point TP1 and the second time point TP2. The first time point TP1, which is a time point in the spraying section, may be a time point included in the first section (e.g., the pre-cooling section P1) before the laser emission section or in the second section (e.g., the post-cooling section P3) after the laser emission section. The second time point TP2 may be a time point included in the laser emission section. In this case, when the skin surface temperature at the first time point TP1 is lower than the skin surface temperature at the second time point TP2, the control module 1400 may apply the first thermal energy at the first time point TP1, and may apply the second thermal energy 'smaller' than the first thermal energy at the second time point TP2. Through the refrigerant condition control unit 1220, the control module 1400 may control the thermal energy applied to the refrigerant at each of the first time point TP1 and the second time point TP2.

In FIG. 4, a first set temperature Ts1, the second set temperature Ts2, and the third set temperature Ts3 are illustrated to be different temperatures, but are not limited thereto, and at least two temperatures of the first set temperature Ts1, the second set temperature Ts2, the third set temperature Ts3 may be the same. Alternatively, the first set temperature Ts1, the second set temperature Ts2, and the third set temperature Ts3 may be preset to be the same. This will be described in detail later with reference to FIGS. 6 to 8.

Additionally, in FIG. 4, the pre-cooling section P1, the inter-cooling section P2, and the post-cooling section P3 are illustrated to be all included, but are not limited thereto, and a refrigerant may be sprayed such that only some sections of the pre-cooling section P1, the inter-cooling section P2n and the post-cooling section P3 are included according to objectives of treatment and types of treatment.

In the above, various operations of the laser module 1100, the cooling module 1200, the sensing unit 1300, the control module 1400, the storage unit 1500, and the tube 1600 of the laser treatment device 100 according to the embodiment of the present disclosure have been described. This may be inferred and applied to the driving method of the laser treatment device 100 having a cooling system to be described later.

Figure 5:
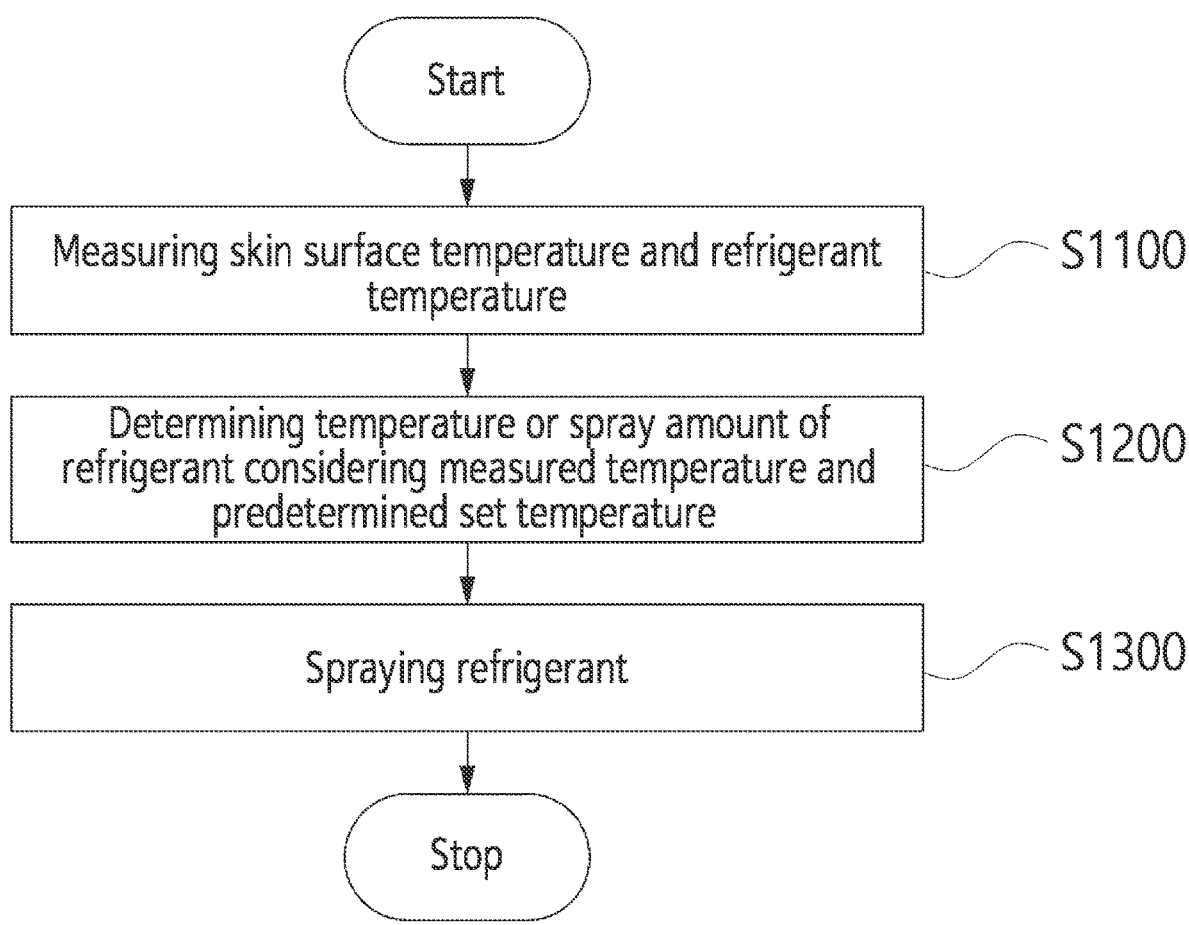
FIG. 5 is a flowchart illustrating the embodiment of the driving method of the laser treatment device disclosed in the present specification.

FIG. 5 is a flowchart illustrating one embodiment of the driving method S1000 of the laser treatment device 100 disclosed in the present specification.

The laser treatment method S1000 by the laser treatment device 100 according to the embodiment of the present disclosure may include measuring the skin surface temperature and the temperature of a refrigerant at S1100; determining the temperature or spray amount of the refrigerant at S1200; and spraying the refrigerant at S1300.

In the laser treatment method S1000 according to the embodiment of the present disclosure, when laser treatment starts, the skin surface temperature and/or the temperature of the refrigerant may be measured at S1100, and the temperature or spray amount of the refrigerant may be determined by considering a measured temperature and a predetermined set temperature at S1200. Additionally, according to the temperature or spray amount of the refrigerant determined at S1200, the spraying of the refrigerant may be performed at S1300.

According to the embodiment, before S1000 starts (or before S1100), a temperature may be preset.

The set temperature may be a desired temperature intended to control the skin surface temperature. Alternatively, the set temperature may be a desired temperature intended to control the temperature of a refrigerant sprayed. Alternatively, the set temperature may be a desired temperature intended to control the temperature of a target which receives a treatment by a laser.

In this case, a user may directly preset each of the skin surface temperature, the temperature of a refrigerant sprayed, and/or the desired temperature of a target as a specific temperature desired to be controlled. For example, the laser treatment device 100 according to the embodiment of the present disclosure may include the input unit that can receive a user's input, and through the input unit, the user may input at least one temperature of the skin surface temperature, the temperature of the refrigerant, and the desired temperature of a target as a specific temperature desired to be controlled. The at least one temperature of the skin surface temperature, the temperature of the refrigerant, and the desired temperature of a target which are input to the input unit may be transmitted to the control module 1400 and may be used as a factor to be considered in determining the temperature or spray amount of the refrigerant at S1200.

In another example, the set temperature may be set by 'the control module' 1400 in consideration of a treatment area, the type of lesion to receive a treatment, the objective of the treatment, and the type of a laser to be used. For example, the laser treatment device 100 according to the embodiment of the present disclosure may include the input unit which can receive a use's input, and through the input unit, the user may input treatment information such as the type of lesion to receive a treatment, the treatment area, the objective of the treatment, and the type of a laser to be used. In this case, the treatment information input to the input unit is transmitted to the control module 1400, and the control module 1400 may preset at least one temperature of the skin surface temperature, the temperature of the refrigerant, and the desired temperature of a target as a specific value based on the received treatment information. The at least one of the skin surface temperature, the temperature of the refrigerant, and the desired temperature of a target preset by the control module 1400 may be modified or confirmed by a user. The at least one temperature of the skin surface temperature, the temperature of the refrigerant, and the desired temperature of a target preset by the control module 1400 may be transmitted to the control module 1400, and may be used as a factor to be considered in determining the temperature or spray amount of the refrigerant at S1200.

Additionally, in the setting of the set temperature, the temperature of at least one of the skin surface temperature, the temperature of a sprayed refrigerant, and the desired temperature of a target may be set to be different according to the laser emission section and the spraying section. In other words, in the setting of the set temperature, the first set temperature Ts1 of the pre-cooling section P1, the second set temperature Ts2 of the inter-cooling section P2, and the third set temperature Ts3 of the post-cooling section P3 may be preset. Additionally, in the setting of the set temperature, the first set temperature Ts1 of the pre-cooling section P1, the second set temperature Ts2 of the inter-cooling section P2, and the third set temperature Ts3 of the post-cooling section P3 may be set to be different. This will be described in detail with reference to FIGS. 6 to 8.

The input unit may be formed on the outer surface of the laser treatment device 100, and may be provided in space separate from the laser treatment device 100 to communicate with the laser treatment device 100 by wire or wirelessly. For example, the input unit may be provided in the form of a display on the outer surface of the handpiece of the laser treatment device 100. For another example, the input unit may be configured as an external device capable of wirelessly communicating with the laser treatment device 100. However, the input unit is not limited thereto, and may be provided in various methods in which set temperature information or treatment information can be transmitted to the control module 1400 of the laser treatment device 100.

As described above, the step of setting the set temperature is described to be performed before S1000 starts, but this is only illustrative, and the set temperature may be set at any suitable step within the S1000.

Hereinafter, each step will be described in detail.

Referring back to FIGS. 2 and 5, at S1100, the skin surface temperature and/or the temperature of the refrigerant may be measured.

Measuring the skin surface temperature and/or the temperature of the refrigerant at S1100 may be performed by transmitting detected temperature information to the control module 1400 after detecting the temperature information by using the sensing unit 1300 of the laser treatment device 100. The temperature information may include at least one of the skin surface temperature and the temperature of the refrigerant. In other words, the laser treatment device 100 may measure the skin surface temperature and/or the temperature of the refrigerant, and specifically, the temperature information may be detected through the sensing unit 1300.

For example, the sensing unit 1300 may include the first temperature sensing unit which can measure the temperature of a skin surface, and the skin surface temperature measured by the first temperature sensing unit may be transmitted to and stored in the control module 1400 of the laser treatment device 100.

For another example, the sensing unit 1300 may include the third temperature sensing unit which can measure the temperature of a refrigerant sprayed by the spraying unit 1230, and the measured temperature of the refrigerant measured by the third temperature sensing unit may be transmitted to and stored in the control module 1400 of the laser treatment device 100.

As illustrated in FIG. 5, the temperature information is illustrated to include the skin surface temperature and the temperature of the refrigerant, but is not limited thereto, and may include temperature information in relation to the refrigerant condition control unit 1220. For example, the sensing unit 1300 may include the second temperature sensing unit which can measure the degree of thermal energy applied to a refrigerant from the refrigerant condition control unit 1220, and temperature information measured by the second temperature sensing unit may be transmitted to and stored in the control module 1400 of the laser treatment device 100.

Additionally, according to FIG. 5, the temperature information is illustrated to include all of the skin surface temperature and the temperature of the refrigerant, but only the skin surface temperature except for the temperature of the refrigerant may be measured and may be considered when determining the temperature or spray amount of the refrigerant at S1200 to be described later. In other words, at S1100 of FIG. 5, the measurement of the temperature of the refrigerant may be omitted.

Referring back to FIG. 5, the laser treatment method according to the embodiment of the present disclosure may include determining the temperature or spray amount of the refrigerant in consideration of the measured temperature at S1100 and a predetermined set temperature at S1200.

According to the embodiment of the present disclosure, in consideration of the measured temperature and the predetermined set temperature, determining the temperature or spray amount of the refrigerant at S1200 may consider the temperatures measured at S1100 when determining the temperature or spray amount of the refrigerant. In addition, S1200 may consider the predetermined set temperature when determining the temperature or spray amount of the refrigerant. In addition, S1200 may consider difference between the measured temperature and the predetermined set temperature when determining the temperature or spray amount of the refrigerant.

The measured temperatures may be temperatures including at least one of a skin surface temperature measured by the sensing unit 1300 and the temperature of a refrigerant sprayed. Specifically, the skin surface temperature may be a temperature which is measured by the first temperature sensing unit and is transmitted to the control module 1400 to be stored. Additionally, the temperature of the refrigerant, which is the temperature of a refrigerant sprayed, may be a temperature which is measured by the third temperature sensing unit and is transmitted to the control module 1400 to be stored.

The predetermined set temperature may be the desired temperature of the skin surface temperature or the desired temperature of a refrigerant preset in the presetting of the temperature described above. Specifically, the predetermined set temperature may be temperature information input to the input unit by a user. Alternatively, the set temperature may be a temperature set by the control module 1400 based on the treatment information input to the input unit by a user.

According to the embodiment of the present disclosure, at S1200, in consideration of the measured temperature and the predetermined set temperature, the characteristics of a refrigerant such as the temperature or spray amount of the refrigerant may be determined. Specifically, the temperature and/or spray amount of the refrigerant may be determined by the refrigerant condition control unit 1220 or the flow rate control unit 1210 controlled by the control module 1400.

According to the embodiment, the temperature of the refrigerant may be controlled by the refrigerant condition control unit 1220 controlled by the control module 1400.

For example, the control module 1400 may be configured such that the refrigerant condition control unit 1220 controls 'the temperature of a refrigerant' to be sprayed by controlling thermal energy applied to the refrigerant such that the skin surface temperature is close to the predetermined set temperature of the skin surface. The temperature of the refrigerant to be sprayed may be controlled and finally the skin surface temperature may be controlled to be close to the predetermined set temperature. In this case, just after being sprayed from the spraying unit 1230, temperature of the refrigerant may increase by air present between the spraying unit 1230 and the target area, that is, outside air, and thus the refrigerant having just sprayed from the spraying unit 1230 may be controlled to be lower than the temperature of the target area by the refrigerant condition control unit 1220. In this case, difference between the temperature of the refrigerant having just sprayed from the spraying unit 1230 and the temperature of the target area may vary according to the temperature of the outside air, and as the temperature of the outside air increases, difference between the temperature of the refrigerant having just sprayed from the spraying unit 1230 and the temperature of the target area may increase. For a specific example, the refrigerant condition control unit 1220 may control the thermal energy applied to the refrigerant such that the temperature of a sprayed refrigerant (e.g., carbon dioxide) is −20° C. or less such that the skin surface temperature is close to the temperature range of −20° C. or more to 10° C. or less. Alternatively, the refrigerant condition control unit 1220 may control thermal energy applied to the refrigerant such that the temperature of the sprayed refrigerant (e.g., carbon dioxide) is 10° C. or less such that the skin surface temperature is close to the temperature range of −20° C. or more to 10° C. or less. The refrigerant condition control unit 1220 may preferably control the thermal energy applied to the refrigerant such that the temperature of the sprayed refrigerant (e.g., carbon dioxide) is −60° C. or more to −20° C. or less such that the skin surface temperature is close to the temperature range of −20° C. or more to 10° C. or less.

Alternatively, thermal energy applied to a refrigerant from the refrigerant condition control unit 1220 may be controlled such that the temperature of a sprayed refrigerant (e.g., carbon dioxide) is −20° C. or less such that the skin surface temperature is close to the temperature range of −20° C. or more to −10° C. or less. Alternatively, thermal energy applied to a refrigerant from the refrigerant condition control unit 1220 such that the temperature of sprayed refrigerant (e.g., carbon dioxide) is −10° C. or less such that the skin surface temperature is close to the temperature range of −20° C. or more to −10° C. or less. Thermal energy applied to a refrigerant from the refrigerant condition control unit 1220 may be preferably controlled such that the temperature of a sprayed refrigerant (e.g., carbon dioxide) is −60° C. or more and −30° C. or less such that the skin surface temperature is close to the temperature range of −20° C. or more and −10° C. or less.

Alternatively, thermal energy applied to a refrigerant from the refrigerant condition control unit 1220 may be controlled such that the temperature of a sprayed refrigerant (e.g., carbon dioxide) is −10° C. or less such that the skin surface temperature is close to the temperature range of −10° C. or more and 0° C. or less. Alternatively, thermal energy applied to a refrigerant from the refrigerant condition control unit 1220 may be controlled such that the temperature of a sprayed refrigerant (e.g., carbon dioxide) is 0° C. or less such that the skin surface temperature is close to the temperature range of −10° C. or more and −10° C. or less. Thermal energy applied to a refrigerant from the refrigerant condition control unit 1220 may be preferably controlled such that the temperature of a sprayed refrigerant (e.g., carbon dioxide) is −60° C. or more and −25° C. or less such that the skin surface temperature is close to the temperature range of −10° C. or more and 0° C. or less.

Alternatively, thermal energy applied to a refrigerant from the refrigerant condition control unit 1220 may be controlled such that the temperature of a sprayed refrigerant (e.g., carbon dioxide) is 0° C. or less such that the skin surface temperature is close to the temperature range of 0° C. or more and 10° C. or less. Alternatively, thermal energy applied to a refrigerant from the refrigerant condition control unit 1220 may be controlled such that the temperature of a sprayed refrigerant (e.g., carbon dioxide) is 10° C. or less such that the skin surface temperature is close to the temperature range of 0° C. or more and 10° C. or less. Thermal energy applied to a refrigerant from the refrigerant condition control unit 1220 may be preferably controlled such that the temperature of a sprayed refrigerant (e.g., carbon dioxide) is −55° C. or more and −25° C. or less such that the skin surface temperature is close to the temperature range of 0° C. or more and 10° C. or less.

When a refrigerant is sprayed by the spraying distance of about 25 mm (a distance between the spraying unit and the skin surface) to control the skin surface temperature to a specific temperature, the temperature of the sprayed refrigerant described above may be the temperature of the refrigerant measured after installing a thermocouple at a distance of about 3 mm from the spraying unit.

However, this is just an example, and the temperature of a sprayed refrigerant may be controlled such that the skin surface temperature is close to a specific temperature range, and the temperature of the sprayed refrigerant may be different according to a measurement protocol (e.g., spraying distance and temperature measurement location of the sprayed refrigerant temperature, etc.).

According to the embodiment, the spray amount of a refrigerant may be controlled by the flow rate control unit 1210 controlled by the control module 1400.

For example, in order to control the skin surface temperature to be close to the predetermined set temperature of the skin surface, the control module 1400 may control the period of opening/closing time or opening/closing cycle of the flow rate control unit 1210 and may control the amount of a refrigerant to be sprayed. By controlling the amount of the refrigerant to be sprayed, the degree of cooling energy applied to the skin surface may be controlled. Additionally, through this, finally, the skin surface temperature may be controlled to be close to the predetermined temperature.

According to the another embodiment, the spray amount of a refrigerant may be controlled by the refrigerant condition control unit 1220.

For example, when the refrigerant condition control unit 1220 increases the degree of thermal energy applied to a refrigerant, that is, increases the temperature of the refrigerant, the degree of freedom of a refrigerant flowing through the refrigerant condition control unit 1220 increases and accordingly static pressure of the refrigerant increases such that the amount of the refrigerant is decreased. Contrarily, when the refrigerant condition control unit 1220 decreases thermal energy applied to a refrigerant, the degree of freedom of a refrigerant flowing through the refrigerant condition control unit 1220 decreases and accordingly, static pressure decreases such that the amount of the refrigerant is increased. By controlling the amount of a refrigerant to be sprayed, the degree of cooling energy applied to the skin surface may be controlled. Additionally, finally, the skin surface temperature may be controlled to be close to the predetermined set temperature.

The control of thermal energy applied to a refrigerant from the refrigerant condition control unit 1220 may be performed through a thermoelectric element, such as a Peltier element, and the control module 1400 may control whether to supply power to the thermoelectric element and/or the amount of a current applied to the thermoelectric element such that the refrigerant condition control unit 1220 can control the amount of the thermal energy applied to the refrigerant. However, this is an example, and through various operations of the control module 1400 and the refrigerant condition control unit 1220 descried above, the refrigerant condition control unit 1220 may control the degree of the thermal energy applied to the refrigerant so as to control the temperature or amount of the refrigerant.

According to the embodiment, at S1200, in consideration of the predetermined set temperature and the measured temperature, the characteristics of a refrigerant may be controlled. The characteristics of a refrigerant may include the temperature, amount, pressure, or speed of the refrigerant, or any suitable combination thereof.

For example, the characteristics of a refrigerant may be controlled based on difference between a preset skin surface temperature and a measured actual skin surface temperature. Specifically, based on whether the measured skin surface temperature is higher or lower than the preset skin surface temperature, the characteristics of a refrigerant may be controlled. When the preset skin surface temperature is lower than the measured actual skin surface temperature, the control module 1400 may control the flow rate control unit 1210 and/or the refrigerant condition control unit 1220 to decrease the actual skin surface temperature. For example, the control module 1400 may increase the amount of a refrigerant by increasing the period of opening/closing time of the flow rate control unit 1210, and may increase the amount of energy applied to the skin surface. For another example, the control module 1400 may control the temperature of a refrigerant to be decreased by decreasing a current applied to the refrigerant condition control unit 1220. On the other hand, when the preset skin surface temperature is higher than the measured actual skin surface temperature, the control module 1400 may control the flow rate control unit 1210 and/or the refrigerant condition control unit 1220 to increase the actual skin surface temperature. For example, the control module 1400 may decrease the amount of a refrigerant by decreasing the period of opening/closing time of the flow rate control unit 1210 and may decrease the amount of cooling energy applied to the skin surface. For another example, the control module 1400 may control the temperature of a refrigerant to be increased by increasing a current applied to the refrigerant condition control unit 1220.

For example, the characteristics of a refrigerant may be controlled based on difference between a predetermined temperature of 'a refrigerant' and a measured actual temperature of 'a refrigerant'. Specifically, the characteristics of a refrigerant may be controlled based on whether the measured temperature of a refrigerant is higher than the predetermined temperature of a refrigerant. When the predetermined temperature of the refrigerant is lower than the measured actual temperature of the refrigerant, the control module 1400 may control the refrigerant condition control unit 1220 to decrease the actual temperature of the refrigerant. For example, the control module 1400 may control the temperature of the refrigerant to be decreased by reducing a current applied to the refrigerant condition control unit 1220. On the other hand, when the predetermined temperature of the refrigerant is higher than the measured actual temperature of the refrigerant, the control module 1400 may control the refrigerant condition control unit 1220 to increase the actual temperature of the refrigerant to be sprayed. For example, the control module 1400 may control the temperature of the refrigerant to be increased by increasing a current applied to the refrigerant condition control unit 1220.

According to the embodiment, at S1200, according to 'the degree of difference' between the predetermined temperature and the measured actual temperature, the characteristics of a refrigerant such as the temperature and/or amount of a refrigerant may be controlled.

For example, there may be difference in detail in the control of the temperature and/or amount of the refrigerant between a case in which difference between the predetermined skin surface temperature and the measured actual skin surface temperature is a first temperature difference and a case in which difference between the predetermined skin surface temperature and the measured actual skin surface temperature is a second temperature difference 'larger' than the first temperature difference.

For example, a case in which difference between the preset skin surface temperature and the measured actual skin surface temperature is the first temperature difference may mean to be closer to the preset skin surface temperature than a case in which difference between the predetermined skin surface temperature and the measured actual skin surface temperature is the second temperature difference. Accordingly, 'the amount of change' between the temperature of a sprayed refrigerant and the temperature of a refrigerant to be sprayed by being controlled may be smaller in the case of the first temperature difference than in the case of the second temperature difference. Similarly, 'the amount of change' between the amount of a sprayed refrigerant and the amount of a refrigerant to be sprayed by being controlled may be smaller in the case of the first temperature difference than in the case of the second temperature difference.

On the other hand, it may be meant that difference between the preset skin surface temperature and the measured actual skin surface temperature is larger in a case in which difference between the preset skin surface temperature and the measured actual skin surface temperature is the second temperature difference than in a case in which difference between the predetermined skin surface temperature and the measured actual skin surface temperature is the first temperature difference. Accordingly, the temperature and/or amount of a refrigerant may be required to be corrected more than in the case of the first temperature difference. In other words, 'the amount of change' between the temperature of a sprayed refrigerant and the temperature of the refrigerant to be sprayed by being controlled may be larger in the case of the second temperature difference than in the case of the first temperature difference. To this end, 'the amount of change' between a current applied previously to the refrigerant condition control unit 1220 and a current to be applied to the refrigerant condition control unit 1220 by being controlled may be larger in the case of the second temperature difference than in the case of the first temperature difference. Similarly, 'the amount of change' between the amount of a sprayed refrigerant and the amount of a refrigerant to be sprayed by being controlled may be larger in the case of the second temperature difference than in the case of the first temperature difference. To this end, 'the amount of change' between the existing opening time of the flow rate control unit 1210 and the opening time of the flow rate control unit 1210 to be opened by being controlled may be larger in the case of the second temperature difference than in the case of the first temperature difference. The above described example has been described based on the predetermined skin surface temperature and the measured actual skin surface temperature, but may be similarly applied to the predetermined temperature of a refrigerant and the measured actual temperature of a refrigerant.

According to the embodiment, at S1200, the characteristics of a refrigerant such as the temperature and/or amount of a refrigerant may be preferably controlled by a proportional integral derivative (PID) control method by considering the predetermined temperature and the measured actual temperature.

According to the embodiment, at S1200, the characteristics of a refrigerant such as the temperature and/or amount of a refrigerant may be controlled by considering an outside temperature. For example, when the preset skin surface temperature is constant, the refrigerant condition control unit may control thermal energy applied to a refrigerant to be different according to the outside temperature. For a specific example, when the preset skin surface temperature is constant, and when the outside temperature is in the temperature range of 10° C. or more to 25° C. or less, generally, as the outside temperature increases, the temperature of a refrigerant sprayed to achieve the preset skin surface temperature may be decreased. Accordingly, as the outside temperature increases, the refrigerant condition control unit may control thermal energy applied to the refrigerant to be decreased.

According to the embodiment, at S1200, by considering 'type' of a refrigerant as well as the measured temperature and the predetermined set temperature, the control module 1400 may control the temperature and/or amount of the refrigerant. Specifically, the control method of the temperature and/or amount of a refrigerant may vary depending on the essential physical characteristics of the refrigerant under atmospheric pressure of the refrigerant.

For example, when carbon dioxide ($CO_2$) is used as a refrigerant, the refrigerant of carbon dioxide may be applied to a skin surface at a relatively lower temperature than HFC-based refrigerants under atmospheric pressure after being sprayed from the spraying unit 1230. For example, in a case in which the refrigerant condition control unit 1220 is the thermoelectric element (e.g., a Peltier element, etc.), when spraying the refrigerant of carbon dioxide by turning off the power of the thermoelectric element, the refrigerant may be sprayed at the temperature of about −40° C. to −70° C. and applied to the skin surface. Specifically, the temperature of the sprayed refrigerant may be affected by the outside temperature, and when the temperature of the outside air is the temperature of 15° C. to 25° C., the temperature of the sprayed refrigerant of carbon dioxide with the power of the thermoelectric element turned off may be the temperature of about −70° C. or more and −50° C. or less. Additionally, when the temperature of the outside air is the temperature of 25° C. to 35° C. or less, the temperature of the sprayed refrigerant of carbon dioxide with the power of the thermoelectric element turned off may be the temperature of about −40° C. or more and −60° C. or less. In this case, the measured temperature of the sprayed refrigerant may be a temperature measured after installing a thermocouple at a distance of about 3 mm from the spraying unit. Accordingly, when carbon dioxide is used as a refrigerant, the refrigerant condition control unit 1220 may control the temperature of the refrigerant by controlling only the degree of heating the refrigerant. In other words, since the temperature of the refrigerant is substantially low even when there is no thermal energy applied to the refrigerant by the refrigerant of carbon dioxide (that is, no heating), the temperature of the sprayed refrigerant may be preferably controlled by controlling the amount of the thermal energy applied to the refrigerant from the refrigerant condition control unit 1220 through 'heating'.

For example, in a case in which an HFC-based substance is used as a refrigerant, when the refrigerant condition control unit 1220 is turned off, the refrigerant may be sprayed at a relatively higher temperature (e.g., −20° C.) than the refrigerant of carbon dioxide. This may be a relatively high temperature to control the skin surface temperature over a wide range. Particularly, it may be difficult to adjust the skin surface temperature to the temperature of about −10° C. or less by using an HFC-based refrigerant without additional cooling. Accordingly, when an HFC-based substance is used as a refrigerant, the refrigerant condition control unit 1220 may be operated to heat and cool the refrigerant. Particularly, in a case in which the refrigerant condition control unit 1220 is the thermoelectric element (e.g., a Peltier element), when a current is applied to the thermoelectric element in a first direction, heat absorption may occur on a first surface of the thermoelectric element, and heat generation may occur on a second surface thereof. Additionally, when a current is applied to the thermoelectric element in a second direction, heat generation may occur on the first surface of the thermoelectric element, and heat absorption may occur on the second surface thereof. In this case, a flow path through which the refrigerant flows may be configured to be in contact with at least one of the first surface and the second surface, and the control module 1400 may be configured to control the direction of a current applied to the thermoelectric element so as to heat or cool the refrigerant depending on a situation.

As described above, it has been mainly described that the control module 1400 determines the temperature or spray amount of the refrigerant in consideration of the measured temperature and the predetermined set temperature at S1200.

However, this is only an example, and according to the embodiment, the control module 1400 may be configured to determine whether the measured actual temperature (e.g., the actual temperature of the skin surface and the actual temperature of a sprayed refrigerant) corresponds to 'condition' of the predetermined set temperature. In this case, the 'condition' of the predetermined set temperature may be a temperature range in which an allowable 'error range' relative to the predetermined set temperature is set.

When the measured actual temperature (e.g., the actual temperature of a skin surface and the actual temperature of a sprayed refrigerant) corresponds to a predetermined set temperature condition, the control module 1400 may determine the temperature or spray amount of a refrigerant to be sprayed by the temperature or spray amount of the refrigerant sprayed previously.

When the measured actual temperature (e.g., the actual temperature of a skin surface and the actual temperature of a sprayed refrigerant) does not correspond to the predetermined set temperature condition, the control module 1400 may be configured to control the temperature or amount of the refrigerant through the refrigerant condition control unit 1220. Alternatively, the control module 1400 may be configured to control the amount of a refrigerant through the flow rate control unit 1210.

Referring back to FIG. 5, the laser treatment method according to the embodiment of the present disclosure may include spraying the refrigerant at S1300.

In this case, in the spraying of the refrigerant at S1300, according to the temperature or spray amount of the refrigerant determined at S1200, the refrigerant may be sprayed.

FIG. 5 illustrates that the driving of the laser treatment device 100 stops when the refrigerant is sprayed, but this is only an example, and when the refrigerant is sprayed, the measuring S1100 of the skin surface temperature and/or the temperature of the refrigerant may be performed again, and accordingly, a series steps may be repeatedly performed.

According to the driving method of the laser treatment device 100 disclosed in the present specification, the temperature or spray amount of the refrigerant to be sprayed may be determined by considering information about the skin surface temperature information and/or temperature of the refrigerant which is measured after measuring the skin surface temperature and/or the temperature of the refrigerant, so the skin surface temperature may be controlled to be close to the predetermined set temperature. Through this temperature feedback, the skin surface temperature, which is the most direct parameter of skin damage, can be stably maintained close to the set temperature. Particularly, by setting the set temperature to be lower than the skin damage temperature, skin damage can be minimized.

Above, the laser treatment method according to the embodiment of the present disclosure has been described, and the above description may be equally applied to the laser treatment method by the laser treatment device 100 according to the another embodiment of the present specification to be described later.

The laser treatment method by the laser treatment device 100 according to the embodiment of the present disclosure may include measuring a temperature; determining the temperature or amount of a refrigerant; and spraying the refrigerant; and emitting a laser.

The emitting of the laser may include emitting a laser toward a target area to receive a treatment. The laser may be generated in the laser generating unit 1110 of the laser module 1100 and may be emitted in the laser emitting unit 1120.

Specifically, the laser module 1100 is connected electrically connected with the control module 1400 and receives the laser emission signal of the control module 1400 so as to emit a laser.

In this case, the control module 1400 may receive a laser emission input by a user and may transmit a laser emission signal to the laser module 1100, so the laser emission of the laser module 1100 may be performed. Alternatively, a condition for the laser emission may be preset in the control module 1400. In this case, when the preset condition is satisfied, the laser module 1100 may be controlled by the control module 1400 such that a laser is emitted. For example, when the skin surface temperature reaches a specific temperature due to the cooling system, the laser module 1100 may be controlled to emit a laser by the control module 1400. In this case, the specific temperature may be preset by considering the skin damage temperature, a temperature at which frost is formed on a skin surface, and a temperature at which interfering substances in the laser path are minimized. This will be described in detail later with reference to FIGS. 17 to 22.

The laser treatment method by the driving of the laser treatment device 100 according to the embodiment of the present disclosure may include the spraying section of a refrigerant and the laser emission section.

In this case, referring to FIG. 4, the refrigerant spraying section may include the pre-cooling section P1, the inter-cooling section P2, and the post-cooling section P3. The refrigerant spraying section may mean a section in which cooling energy is applied to a skin surface by the spraying of a refrigerant. However, there may be difference between the time point of the spraying of a refrigerant and a time point at which cooling energy is applied to the skin surface, and the time difference may be very small, and in this case, the refrigerant spraying section and a section in which the cooling energy is applied to the skin surface may be used to have substantially the same meaning.

The pre-cooling section P1 may mean a section in which cooling energy is applied to the skin surface by a refrigerant before the starting point of the laser emission section. However, although it is described that the cooling energy is applied to the skin surface 'before' the starting point of the laser emission section, when cooling energy is applied to the skin surface by a refrigerant at the starting point of the laser emission, the starting point of the laser emission may also be included in the pre-cooling section P1. The pre-cooling section P1 may be intended to decrease the skin surface temperature 'in advance' so as to prevent the skin surface from reaching the skin damage temperature due to the increase of the skin surface temperature by accumulation of thermal energy by laser emission in the laser emission section. Alternatively, the pre-cooling section P1 can be performed to anesthetize the skin 10 before laser emission.

The inter-cooling section P2 may mean a section in which cooling energy is applied to the skin surface by a refrigerant in the laser emission section. The inter-cooling section P2 may also be used as terms such as an inter-cooling section, a real-time cooling section, and a cooling section during laser emission. At least a portion of the inter-cooling section P2 and at least a portion of the laser emission section may overlap on a time axis. That is, cooling in the inter-cooling section P2 and laser emission in the laser emission section may be performed at least partially at the same time.

At least a portion of the inter-cooling section P2 may overlap the laser emission section on a time axis and may be a section in which the skin surface temperature may increase greatly by laser emission. In this case, cooling the skin surface such that the skin surface temperature is controlled to be less than the skin damage temperature may be the main objective of the inter-cooling.

The post-cooling section P3 may mean a section in which cooling energy is applied to the skin surface by a refrigerant after the stopping time of the laser emission section. However, although cooling energy is applied 'after' the stopping time of the laser emission section, when cooling energy is applied to the skin surface by a refrigerant at the stopping time of the laser emission, the stopping time of the laser emission may also be included in the post-cooling section P3.

The post-cooling section P3 is a section after the stopping time of the laser emission and may be intended to decrease the skin surface temperature and/or the temperature of a target to a normal temperature or to alleviate pain after laser treatment.

Hereinafter, the embodiments of the driving method of the laser treatment device in the pre-cooling section P1, the inter-cooling section P2, and the post-cooling section P3 will be described in detail.

The laser treatment method by the laser treatment device 100 according to the embodiment of the present disclosure may be performed through the pre-cooling, the inter-cooling, and the post-cooling. In other words, the laser treatment method by the laser treatment device 100 according to the embodiment of the present disclosure may include the pre-cooling section P1, the inter-cooling section P2, and the post-cooling section P3.

Figure 6:
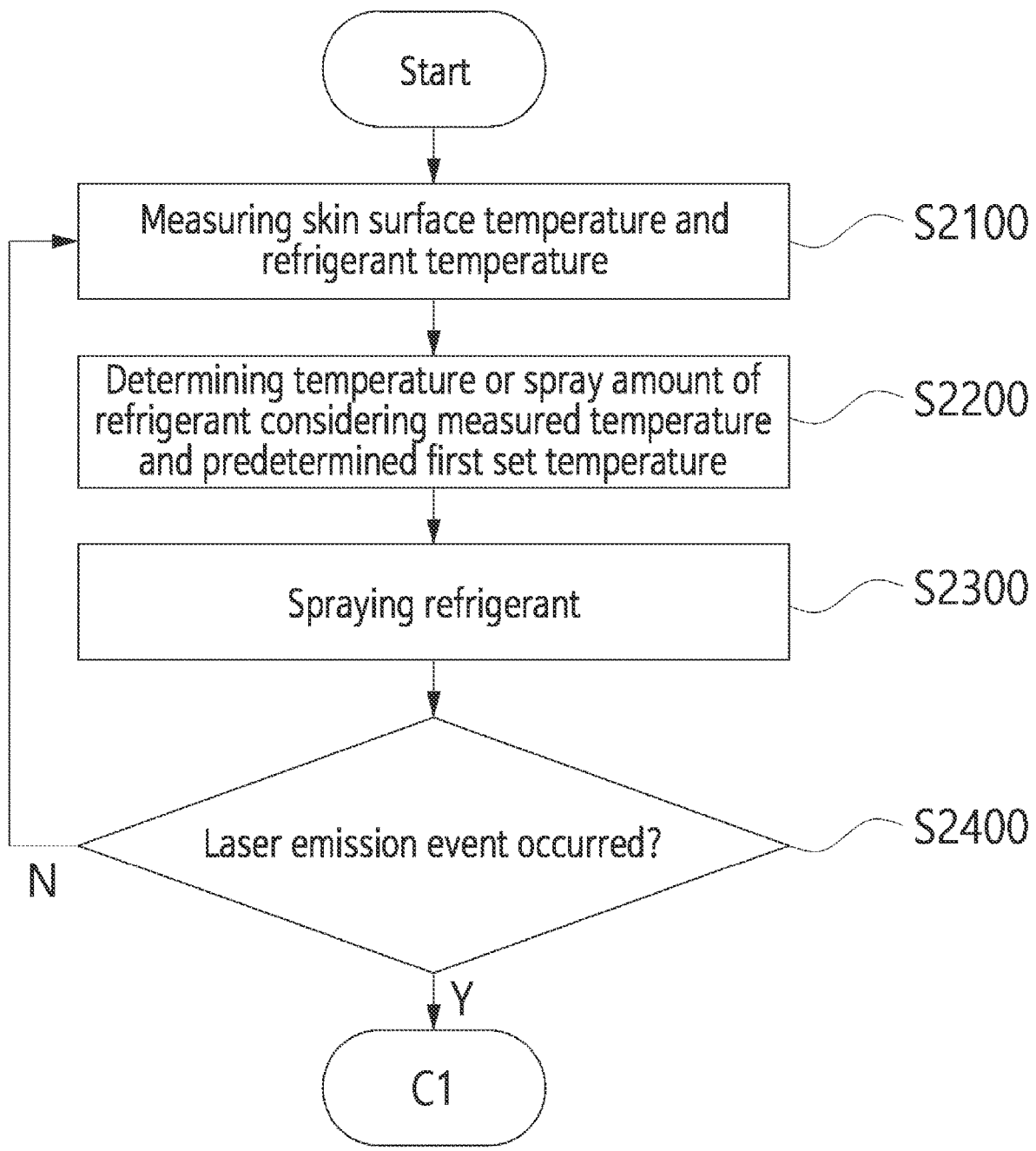
FIG. 6 is a flowchart illustrating a pre-cooling and a laser irradiation method according to the embodiment of the laser treatment method disclosed in the present specification.

Hereinafter, description will be made referring to FIGS. 4 and 6. FIG. 6 is a flowchart S2000 illustrating the pre-cooling and the laser irradiation method according to the embodiment of the laser treatment method disclosed in the present specification.

The pre-cooling may include measuring the skin surface temperature and/or the temperature of the refrigerant at S2100; determining the temperature or spray amount of the refrigerant at S2200; spraying the refrigerant at S2300; and determining whether a laser emission event occurs at S2400.

S1100 described above may be equally applied to the measuring of the skin surface temperature and/or the temperature of the refrigerant at S2100. When described around the feature of the pre-cooling section P1, the temperature of a refrigerant sprayed before the start point of the laser emission section and a skin surface temperature before the start point of the laser emission section may be measured at S2100.

According to FIG. 6, the temperature of the refrigerant and the skin surface temperature are illustrated be measured at S2100, but except for the temperature of the refrigerant, only the skin surface temperature may be measured and be considered in determining the temperature or spray amount of the refrigerant at S2200 to be described later. In other words, at S2100 of FIG. 6, the measurement of the refrigerant temperature may be omitted.

S1200 may be equally applied to the determining of the temperature or spray amount of the refrigerant at S2200. Accordingly, hereinafter, characteristics of the pre-cooling section P1 will be mainly described.

Referring back to FIG. 6, the laser treatment method according to the embodiment of the present disclosure may include determining the temperature or spray amount of the refrigerant at S2200 by considering a temperature measured at S2100 and the predetermined first set temperature.

The first set temperature Ts1 may be a desired temperature intended to control the skin surface temperature in the pre-cooling section. Alternatively, the first set temperature Ts1 may be a desired temperature intended to control the temperature of a sprayed refrigerant in the pre-cooling section. Alternatively, the first set temperature Ts1 may be a desired temperature intended to control the temperature of a target on which a treatment is performed by a laser in the pre-cooling section.

In an embodiment, the first set temperature Ts1 may be determined by considering the degree of the increase of the skin surface temperature in the laser emission section, the skin damage temperature, and whether a laser interfering substance is generated in the laser emission section. In addition, the first set temperature Ts1 may be set by a user or may be set in such a manner that a user selects a value set by the control module 1400 by using treatment information and temperature information stored in the control module 1400.

For example, in the laser emission section, light energy of a laser may be converted into thermal energy in a target and the converted thermal energy may be accumulated in the target, so the temperature of the skin including the target and the skin surface may be increased. In this case, when the skin surface temperature increased higher than the skin damage temperature in the laser emission section, the skin surface may be damaged. Accordingly, in order to control the skin surface temperature to increase only below the skin damage temperature even if the skin surface temperature increases in the laser emission section, the skin surface temperature may be decreased before the laser emission in the pre-cooling section P1. To this end, in the pre-cooling section P1, the skin surface temperature may be set as the first set temperature Ts1 by considering the degree of temperature increase by the laser emission and the skin damage temperature. In this case, the skin damage temperature may vary depending on a treatment type and skin type, but in general, when a skin temperature reaches a temperature within the range of 40° C. to 60° C., the skin may be damaged by heat. According to the exemplary embodiment, a skin temperature reaches a temperature within the range of 50° C. to 60° C., the skin may be damaged by heat. However, the damage to the skin is not limited thereto, and those skilled in the art may set the first set temperature Ts1 in consideration of the degree of accumulation of thermal energy that may cause skin damage. For example, even when a skin temperature is continuously maintained at the temperature of 40° C. or less, skin damage may occur, and in this case, the first set temperature Ts1 may be set in consideration of the amount of time for which heat is exposed to the skin and/or the degree of heat accumulation.

For another example, to minimize skin damage in the laser emission section, the first set temperature Ts1 may be set by considering the position of a treatment target, the type of the skin which received a treatment, the type of a laser, and the intensity of the laser's output, etc. For example, as the position of a treatment target is close to a skin surface, the increasing degree of a skin surface temperature by the laser emission is likely to be high, and thus in consideration of this, the first set temperature Ts1 of the pre-cooling section P1 may be set. Additionally, as the intensity of the output of the laser to be used increases, the amount of thermal energy accumulated in a target may be increased, and thus by considering the intensity of the output of the laser according to the type of the laser to be used, the first set temperature Ts1 of the pre-cooling section P1 may be set.

For another example, the first set temperature Ts1 may be set in consideration of whether a laser interfering substance is generated in the laser emission section. For example, when in the laser emission section after the pre-cooling section P1, the laser interfering substance such as frost, ice, dry ice, and vapor remains in a laser emission path or on the skin surface, a laser may be scattered. Accordingly, in the pre-cooling section P1, the first set temperature Ts1 may be set such that the laser interfering substance does not remain in the laser emission section.

In an embodiment, the first set temperature Ts1 may be set by considering a treatment area and a lesion to receive a treatment. For example, during a laser treatment for a vascular lesion, when the pre-cooling of the skin is performed to a temperature corresponding to a blood vessel constriction temperature condition, a blood vessel may constrict and a treatment target may not be seen. Accordingly, during the pre-cooling of the laser treatment for the vascular lesion, the first set temperature Ts1 may be set by considering the constriction temperature condition of the vascular lesion. The laser treatment method of the present disclosure for vascular lesion will be described in detail later with reference to FIGS. 23 and 24.

In the embodiment, the first set temperature Ts1 may be set to be different even in the pre-cooling section P1.

For example, as described above, to minimize the possibility of skin damage due to temperature rise by the laser emission of the laser emission section in the pre-cooling section P1, it may be required to set the first set temperature Ts1 relatively low, and to prevent laser interfering substances from remaining on a skin surface in the laser emission section, it may be required to set the first set temperature Ts1 relatively high.

In this case, in the later section of the pre-cooling section P1 and a section adjacent to the starting point of the laser emission section, the first set temperature Ts1 may be set such that laser interfering substances do not remain on a skin surface. When laser interfering substances on the skin surface are not present from time at which the laser emission section starts, laser scattering may be sufficiently prevented, and thus the first set temperature Ts1 may be set to a temperature at which the laser interfering substances do not remain in only a section just before the laser emission such that laser scattering may be prevented.

Additionally, in a section except for the later section of the pre-cooling section P1, the first set temperature Ts1 may be set to be relatively low, and thus in the laser emission section, the possibility of skin damage by the laser emission may be minimized.

In other words, in a section except for the later section of the pre-cooling section P1 (e.g., the first and half section of the pre-cooling section P1), the first set temperature Ts1 may be set to be as low as possible such that the possibility of skin damage in the laser emission section is minimized, and in the later section of the pre-cooling section P1, the first set temperature Ts1 may be set to a temperature at which laser interfering substances do not remain on the skin surface such that laser scattering can be minimized in the laser emission section. Accordingly, even in the pre-cooling section P1, the first set temperature Ts1 may be set to be different.

In the embodiment, the first set temperature Ts1 may be a temperature of a specific range. Specifically, the first set temperature Ts1 may be a temperature range including an allowable 'error range' relative to the first set temperature Ts1.

In this case, the error range of the first set temperature Ts1 may be set to be different even in the pre-cooling section P1. For example, in a section just before the laser emission section included in the pre-cooling section P1, a skin surface temperature may be controlled to a temperature at which a laser interfering substance such as frost is not formed on a skin surface. In this case, in order to control the skin surface temperature to a temperature at which the laser interfering substance is not formed on the skin surface, the error range may be preferably set to be narrow. In other words, in a section just before the laser emission section included in the pre-cooling section P1, to precisely control the skin surface temperature such that frost is not formed on a skin surface, the error range may be set to be relatively narrow. On the other hand, in the initial section of the pre-cooling section P1, which is separated in time from the laser emission section, cooling may be performed to decrease the skin surface temperature as much as possible such that the possibility of skin damage is reduced in the laser emission section. In this case, in the initial section of the pre-cooling section P1, the skin surface temperature is allowed to be controlled relatively less precisely, and thus the error range may be preset to be relatively wide.

In the above, the first set temperature Ts1 is explained to be set based on the skin surface temperature, but is not limited thereto, and it is clear to those skilled in the art that a specific temperature may be preset based on the temperature of a refrigerant, which is a direct variable of the skin surface temperature.

The laser treatment method may include determining S2200 of the temperature or spray amount of the refrigerant by considering a skin surface temperature and/or the temperature of a refrigerant measured at S2100. Specifically, the control module 1400 may control the refrigerant condition control unit 1220 by considering the skin surface temperature and/or the temperature of the refrigerant measured at S2100 and may determine the temperature and/or spray amount of a refrigerant at S2200. Alternatively, the control module 1400 may control the amount of a refrigerant supplied to the spraying unit 1230 by controlling the opening/closing cycle of the flow rate control unit 1210, the period of opening/closing time and may determine the spray amount of a refrigerant at S2200.

In the spraying of a refrigerant at S2300, a refrigerant may be sprayed according to the temperature or spray amount of the refrigerant determined at S2200.

When a refrigerant is sprayed at S2300, determining whether the laser emission event occurs at S2400 may proceed.

The laser emission event may occur by inputting a laser emission signal by a user. Alternatively, as a predetermined time elapses after the pre-cooling starts, the laser emission event may occur. Alternatively, the laser emission event may occur when a skin surface temperature and/or a temperature of a refrigerant is substantially the same as the first set temperature Ts1 set such that frost does not remain on a skin surface.

At the determining of whether the laser emission event occurs at S2400, whether the pre-cooling section P1 stops may be determined according to whether the laser emission event occurs. Specifically, at S2400, the control module 1400 may be configured to determine whether or not the laser emission event occurs when a refrigerant is sprayed at S2300. When the laser emission event does not occur, the control module 1400 may control the laser treatment device 100 such that the measuring of a skin surface temperature and a refrigerant temperature is performed at S2100 such that a series of the steps may be performed again.

On the other hand, when the laser emission event occurs, the control module 1400 may control the laser treatment device 100 such that the pre-cooling stops and the inter-cooling C1 is performed.

However, here, the control module 1400 is described to 'determine' whether the laser emission event occurs, but is not limited thereto, and when the laser emission event occurs, a laser emission signal is transmitted to the control module 1400, and the control module 1400 may control the laser treatment device 100 such that the inter-cooling C1 is performed even if the control module 1400 does not determine whether the laser emission event occurs.

As described above, after the control module 1400 'considers' the measured temperature and the predetermined first set temperature Ts1 at S2200, 'the determining' of the temperature or spray amount of the refrigerant has been mainly described. However, this is only an example, and according to the embodiment, the control module 1400 may be configured to 'determine' whether a measured actual temperature (e.g., the actual temperature of a skin surface and the actual temperature of a sprayed refrigerant) corresponds to the predetermined first set temperature condition. In this case, the predetermined first set temperature condition may be a temperature range in which an allowable 'error range' relative to the predetermined first set temperature is set. Alternatively, the first set temperature condition may be any suitable condition including a condition in which the skin surface temperature is maintained for a specific period of time relative to a specific temperature value.

When the measured actual temperature (e.g., the actual temperature of a skin surface, the actual temperature of a sprayed refrigerant) corresponds to the predetermined first set temperature condition, the control module 1400 may determine the temperature or spray amount of a refrigerant to be sprayed such that the refrigerant is sprayed by having the temperature or spray amount of a sprayed refrigerant.

When the measured actual temperature (e.g., the actual temperature of a skin surface, the actual temperature of a sprayed refrigerant) does not correspond to the predetermined first set temperature condition, the control module 1400 may control the temperature or amount of a refrigerant through the refrigerant condition control unit 1220. Alternatively, the control module 1400 may control the amount of a refrigerant through the flow rate control unit 1210.

Figure 7:
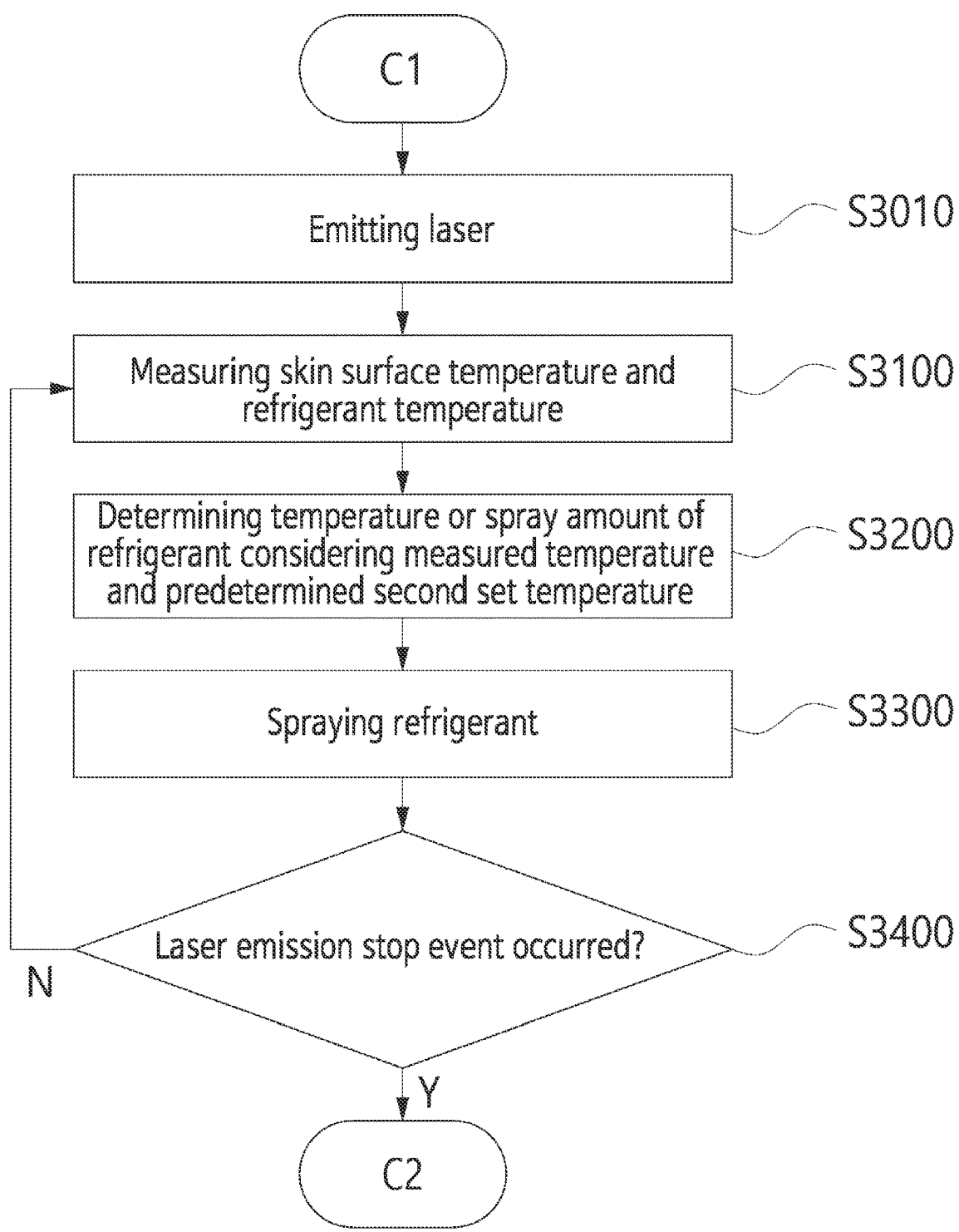
FIG. 7 is a flowchart illustrating an inter-cooling and the laser irradiation method according to the embodiment of the laser treatment method disclosed in the present specification.

The following will be described with reference to FIGS. 4 and 7. FIG. 7 is a flowchart S3000 illustrating the inter-cooling and the laser irradiation method according to the embodiment of the laser treatment method disclosed in the present specification.

The inter-cooling may include: emitting a laser at S3010; measuring the skin surface temperature and/or the temperature of a refrigerant at S3100; determining the temperature or amount of the refrigerant at S3200; spraying the refrigerant at S3300; and determining whether a laser emission stop event occurs at S3400.

The emitting of a laser at S3010 may be performed such that thermal energy is applied to a target by a laser output by the laser module 1100 such that the temperature of a treatment target is the desired temperature of the target or more. The desired temperature of a target may mean a temperature that can cause heat ablation in the target.

The desired temperature of a target may be different according to a treatment type and/or the type of a target tissue but may generally be the temperature within about 40° C. to 60° C. The desired temperature of a target may preferably be a temperature within about 50° C. to 60° C.

However, thermal energy accumulated in a target by a laser may be conducted or transmitted to a skin surface, and thus a skin surface temperature may be increased. In this case, when the skin surface temperature is a skin damage temperature or more, the side effect of skin damage may occur, so through measuring a skin surface temperature and/or temperature of a refrigerant at S3100; controlling the temperature or amount of a refrigerant at S3200; and spraying a refrigerant at S3300 as described later, the side effect of skin damage by laser emission may be minimized.

S1100 described above may be applied to the measuring of a skin surface temperature and/or the temperature of a refrigerant at S3100 in the same way. When mainly describing the characteristics of the inter-cooling section P2, at S3100, the temperature of a sprayed refrigerant in the laser emission section may be measured, and the skin surface temperature of the laser emission section may be measured. According to FIG. 7, the temperature of a refrigerant and the skin surface temperature are illustrated to be all measured at S3100, but only the skin surface temperature except for the temperature of the refrigerant may be measured and be considered when determining the temperature or spray amount of the refrigerant at S3200 to be described later. In other words, at S3100 of FIG. 7, the measurement of the refrigerant temperature may be omitted.

S1200 described above may be applied to the determining S3200 of the temperature or spray amount of the refrigerant in the same way. Accordingly, hereinafter, the characteristics of the inter-cooling section P2 will be mainly described.

Referring back to FIG. 7, the laser treatment method according to the embodiment of the present disclosure may include determining the temperature or spray amount of the refrigerant at S3200 by considering the measured temperature and the predetermined second set temperature Ts2 at S3100.

The second set temperature Ts2 may be a desired temperature intended to control a skin surface temperature in the inter-cooling section P2. Alternatively, the second set temperature Ts2 may be a desired temperature intended to control the temperature of a sprayed refrigerant in the inter-cooling section P2. Alternatively, the second set temperature Ts2 may be a desired temperature intended to control the desired temperature of a target on which a treatment will be performed by a laser in the inter-cooling section P2.

In an embodiment, the second set temperature Ts2 may be set by considering the degree of the increase of the skin surface temperature of the laser emission section, the temperature of a target and the desired temperature of a target in the laser emission section, the skin damage temperature, and whether the laser interfering substance of the laser emission section is generated. In addition, the second set temperature Ts2 may be set directly by a user or in such a manner that a user selects a value set by the control module 1400 using the treatment information and temperature information stored in the control module 1400.

For example, the second set temperature Ts2 may be set by considering the degree of the increase of the skin surface temperature of the laser emission section. The degree of the increase of the skin surface temperature may be different according to the type of a laser related to output and wavelength, a treatment area, and the position of the treatment area. Specifically, as the output of the laser increases, the degree of the increase of the skin surface temperature may increase, and the type and position of a target in which the laser is absorbed may be different according to the wavelength of the laser, so the degree of the increase of the skin surface temperature may be different according to the laser type related to the laser output and wavelength. Additionally, as the treatment area is located close to a skin surface, the degree of the increase of the skin surface temperature may be increased. Accordingly, the second set temperature Ts2 may be set in consideration of the above variables.

For example, the second set temperature Ts2 may be set by considering 'a temperature of a target and 'the desired temperature of a target' in the laser emission section. Specifically, in at least a portion of the laser emission section, for heat ablation of the treatment area (a target), thermal energy by a laser is required to be applied to the treatment area such that the temperature of the treatment area is the desired temperature of a target or more. Accordingly, the second set temperature Ts2 for the skin surface temperature may be set such that the temperature of a target can sufficiently reach the desired temperature of a target.

For example, the second set temperature Ts2 may be set by considering a skin damage temperature. Specifically, in the laser emission section, the skin surface temperature may also be increased by the conduction and transmission of thermal energy applied to a target by a laser. In this case, when the skin surface temperature is higher than the skin damage temperature, the side effect of skin damage may occur. Accordingly, to minimize the side effect of skin damage, the second set temperature Ts2 may be set to a temperature considered such that the skin surface temperature does not reach the skin damage temperature.

For example, the second set temperature Ts2 may be set by considering whether a laser interfering substance (e.g., a substance of a solid phase) is produced 'in a laser path' during laser output. Specifically, when a refrigerant is sprayed from the cooling module 1200, the refrigerant expands adiabatically due to the Joule-Thomson effect, and the temperature of the refrigerant may be significantly decreased. In this case, a substance of solid phase may also occur in the refrigerant, and moisture in a surrounding atmosphere may be instantaneously changed into a solid phase such as ice. When the substance of a solid phase is present in the laser path, the substance may scatter a laser and may decrease the efficiency of a laser treatment. Accordingly, the second set temperature Ts2 may be set as a temperature corresponding to the temperature of a refrigerant considered to minimize the ratio of the solid phase in the laser path.

For example, the second set temperature Ts2 may be set by considering whether a laser interfering substance is generated 'on a skin surface'. Specifically, when a skin surface temperature is controlled to be 0° C. or less, a laser interfering substance such as frost may be generated on the skin surface, and the laser interfering substance may scatter a laser and may interfere with efficient laser treatment. Accordingly, the second set temperature Ts2 may be set by considering a skin surface temperature in which a laser interfering substance is not generated. The second set temperature Ts2 may be preferably set as a temperature higher than 0° C. in which a laser interfering substance such as frost is not generated.

In an embodiment, the second set temperature Ts2 may be set to be different even in the inter-cooling section P2. For example, in the initial section of the inter-cooling section P2, the total amount of thermal energy applied by a laser may be relatively small, so in the initial section of the inter-cooling section P2, whether laser interfering substance is generated in the laser path and/or on the skin surface, rather than the skin damage temperature, may be an important factor to be considered when presetting the second set temperature Ts2. On the other hand, in the later section of the inter-cooling section P2, the total amount of thermal energy applied by the laser may be relatively large, so the possibility of skin damage may be relatively high. Accordingly, in the later section of the inter-cooling section P2, the second set temperature Ts2 may be set by considering the skin damage temperature to be relatively important. Accordingly, even in the inter-cooling section P2, the second set temperature Ts2 may be suitably set to be different according to a situation.

In an embodiment, the second set temperature Ts2 may be the temperature of a specific range. Specifically, the second set temperature Ts2 may be a temperature range in which an allowable 'error range' relative to the second set temperature Ts2 is included. The error range of the second set temperature Ts2 may be set to be different even in the laser emission section. For example, the amount of heat accumulation by the laser treatment is larger in the later section of the laser emission section than in the initial section of the laser emission section, and the possibility of skin damage is relatively high, so the error range of the later section of the laser emission section may be preset to be narrower than the error range of the initial section of the laser emission section such that the skin surface temperature is precisely controlled.

In the above, the second set temperature Ts2 is described to be set based on the skin surface temperature, but is not limited thereto, and it is clear to those skilled in the art that a specific temperature can be set based on the temperature of a refrigerant which is a direct variable of the skin surface temperature.

Referring back to FIG. 7, the laser treatment method may include determining S3200 of the temperature or spray amount of a refrigerant by considering the skin surface temperature and/or the temperature of the refrigerant measured at S3100. Specifically, the control module 1400 may determine the temperature and/or spray amount of a refrigerant at S3200 by controlling the refrigerant condition control unit 1220 by considering the skin surface temperature and/or the temperature of the refrigerant measured at S3100. Alternatively, the control module 1400 may determine the spray amount of a refrigerant at S3200 by controlling the amount of a refrigerant supplied to the spraying unit 1230 by the opening/closing cycle and period of opening/closing time of the flow rate control unit 1210.

In the spraying of a refrigerant at S3300, a refrigerant may be sprayed according to the temperature or spray amount of the refrigerant determined at S3200.

When the refrigerant is sprayed at S3300, determining whether the stop event of the laser emission occurs may be performed at S3400.

The laser emission stop event may occur when stopping the input of a laser emission signal by a user, and as a predetermined time elapses after the inter-cooling starts, the laser emission stop event may occur. Alternatively, the laser emission stop event may occur when a skin surface temperature and/or a temperature of a refrigerant is substantially the same as the predetermined second set temperature. Alternatively, the laser emission stop event may occur as a predetermined time elapses relative to time at which the temperature of a target reaches the desired temperature of a target. However, the laser emission stop event is not limited thereto, and may occur in any suitable method.

At the determining S3400 of whether the laser emission stop event occurs, whether the inter-cooling section P2 stops according to whether the laser emission stop event occurs. Specifically, at S3400, when a refrigerant is sprayed at S3300, the control module 1400 may determine whether or not the stop event of the laser emission occurs.

When the laser emission stop event does not occur, the control module 1400 may control the laser treatment device 100 such that the measuring of the skin surface temperature and the refrigerant temperature is performed at S3100 such that a series of the steps can be performed again.

On the other hand, when the stop event of the laser emission occurs, the control module 1400 may stop the inter-cooling and may control the laser treatment device 100 such that the post-cooling C2 is performed.

However, here, the control module 1400 is described to 'determine' whether the laser emission stop event occurs, but is not limited thereto, and when the laser emission stop event occurs, a laser stop signal is transmitted to the control module 1400, and even if the control module 1400 does not determine whether the stop event of the laser emission occurs, the laser treatment device 100 may be controlled such that the post-cooling C2 is performed.

As described above, it has been mainly described that the control module 1400 determines the temperature or spray amount of a refrigerant by considering the measured temperature and the predetermined second set temperature Ts2 at S3200. However, this is only an example, and according to the embodiment, the control module 1400 may be configured to determine whether the measured actual temperature (e.g., the actual temperature of a skin surface and the actual temperature of a sprayed refrigerant) corresponds to the predetermined second set temperature condition. In this case, 'the condition' of the predetermined second set temperature may be a temperature range in which an allowable 'error range' relative to the predetermined second set temperature is preset. Alternatively, the second set temperature condition may be any suitable condition including a condition in which the skin surface temperature is maintained for a specific period of time relative to a specific temperature value.

When the measured actual temperature (e.g., the actual temperature of a skin surface, and the actual temperature of a sprayed refrigerant) corresponds to the predetermined second set temperature condition, the control module 1400 may determine the temperature or spray amount of a refrigerant to be sprayed such that the refrigerant is sprayed by having the temperature or spray amount of a sprayed refrigerant.

When the measured actual temperature (e.g., the actual temperature of a skin surface, the actual temperature of a sprayed refrigerant) does not correspond to the predetermined second set temperature condition, the control module 1400 may control the temperature or amount of a refrigerant through the refrigerant condition control unit 1220. Alternatively, the control module 1400 may control the amount of a refrigerant through the flow rate control unit 1210.

Figure 8:
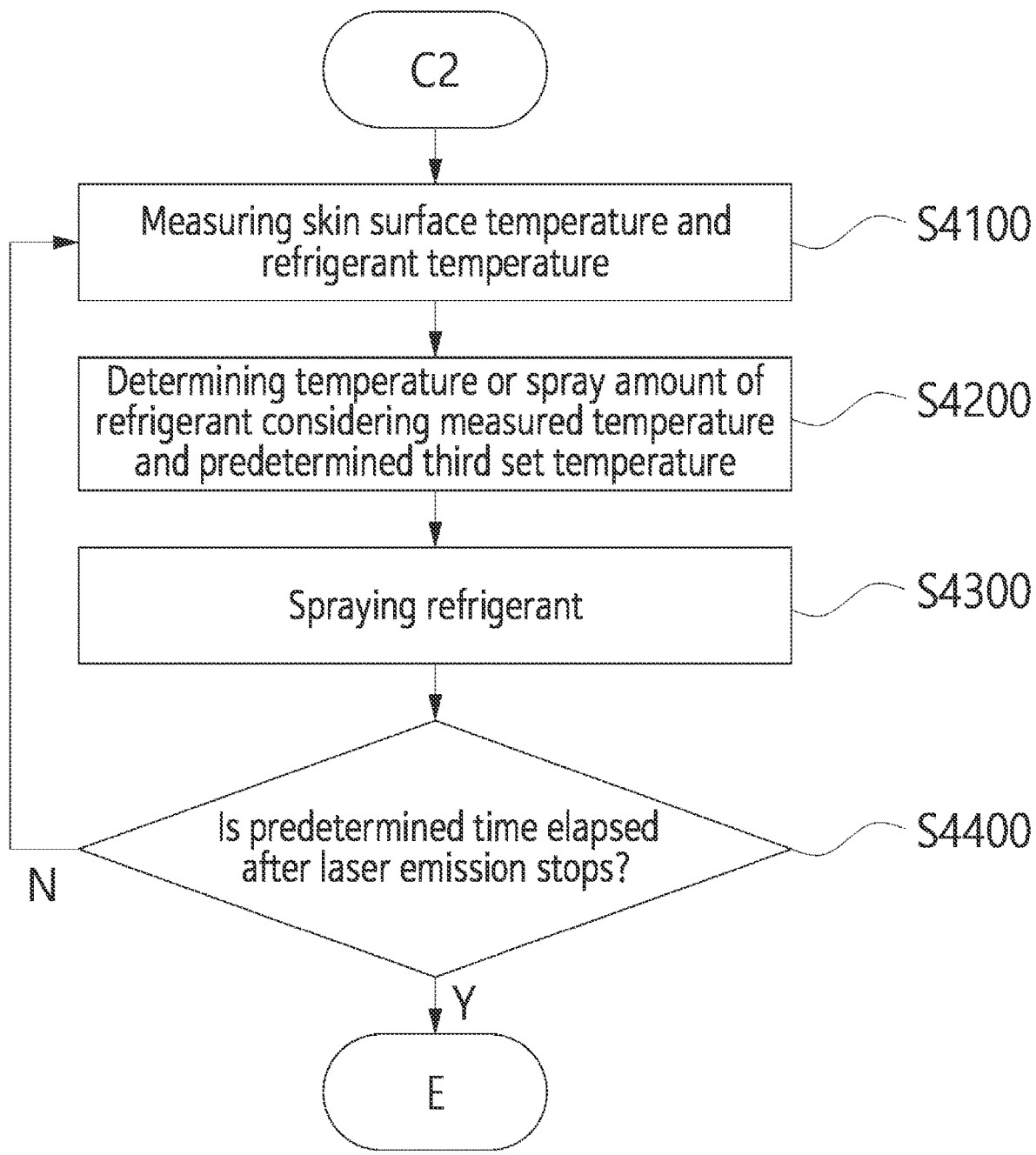
FIG. 8 is a flowchart illustrating the post-cooling and the laser irradiation method according to the embodiment of the laser treatment method disclosed in the present specification.

The following will be described with reference to FIGS. 4 and 8. FIG. 8 is a flowchart S4000 illustrating the post-cooling and laser irradiation method of the laser treatment method disclosed in the present specification according to the embodiment.

The post-cooling may include: measuring a skin surface temperature and/or the temperature of a refrigerant at S4100; determining the temperature or amount of a refrigerant at S4200; spraying a refrigerant at S4300; and determining whether a preset period of time elapses after laser emission stops at S4400.

S1100 described above may be applied to the measuring S4100 of the skin surface temperature and the temperature of the refrigerant in the same way. When mainly describing the characteristics of the post-cooling section P3, at S4100, the temperature of a refrigerant sprayed after the 'stopping' time of the laser emission section may be measured, and the skin surface temperature after the stopping time of the laser emission section may be measured. That is, a temperature of a sprayed refrigerant and/or a skin surface temperature after the laser emission stops may be measured at S4100. According to FIG. 8, the temperature of the refrigerant and the skin surface temperature are illustrated to be all measured at S4100, but only the skin surface temperature except for the temperature of the refrigerant may be measured and may be considered when determining the temperature or spray amount of the refrigerant at S4200 to be described later. In other words, at S4100 of FIG. 8, the measurement of the refrigerant temperature may be omitted.

S1200 described above may be applied to the determining S4200 of the temperature or spray amount of the refrigerant in the same way. Accordingly, hereinafter, the characteristics of the post-cooling section P3 will be mainly described.

Referring back to FIG. 8, the laser treatment method according to the embodiment of the present disclosure may include determining the temperature or spray amount of the refrigerant at S4200 by considering the measured temperature measured at S4100 and the predetermined third set temperature Ts3.

The third set temperature Ts3 may be a desired temperature intended to control the skin surface temperature in the post-cooling section P3. Alternatively, the third set temperature Ts3 may be a desired temperature intended to control the temperature of a sprayed refrigerant in the post-cooling section P3. Alternatively, the third set temperature Ts3 may be a target temperature intended to control the desired temperature of a target to receive a laser treatment in the post-cooling section P3.

In an embodiment, the third set temperature Ts3 may be set by considering the degree of the increase of the skin surface temperature, a pain-minimizing temperature, and a skin dying temperature by cooling, etc. in the laser emission section. In addition, the third set temperature Ts3 may be set directly by a user or in such a manner that a user selects a value set by the control module 1400 using treatment information and temperature information stored in the control module 1400.

For example, the third set temperature Ts3 may be set by considering the degree of the increase of the skin surface temperature in the laser emission section. Specifically, the post-cooling may be performed to decrease the skin surface temperature increased by laser output in the laser emission section to a normal body temperature. Accordingly, in the post-cooling section P3, a refrigerant may be sprayed by considering the skin surface temperature according to the degree of the increase of the skin surface temperature in the laser emission section, and in consideration of the above description, the set temperature of the skin surface to be controlled in the post-cooling section P3 may be set as the third set temperature Ts3.

For example, the third set temperature Ts3 may be set by considering temperature at which pain of a skin surface or a tissue adjacent to a target is minimized. Specifically, the post-cooling may function to minimize damage to the skin surface and to minimize pain. Accordingly, the third set temperature Ts3 of the post-cooling section P3 may be set by considering a temperature at which pain is minimized. For example, the third set temperature may be set as the temperature of 30° C. or less which is a temperature at which the activity of the nociceptor of the skin surface or a tissue adjacent to a target is decreased. Alternatively, the third set temperature Ts3 may be set as the temperature (preferably, the temperature of 0° C. or more and 10° C. or less) of 10° C. or less which is a temperature at which the activity of the nociceptor of a skin surface or a tissue adjacent to a target is decreased.

For example, the third set temperature Ts3 may be set by considering a temperature at which a skin surface or a tissue of the skin dies due to cooling. Specifically, for example, when a skin surface or the skin is exposed to the temperature of 0° C. or less for a long period of time, the death of the tissue of the skin may be caused by frostbite. For another example, when a skin surface or the skin is exposed to the temperature of −20° C. or less, the death of the tissue of the skin may be caused in spite of the exposure for a short period of time. Accordingly, in the post-cooling section P3, the third set temperature Ts3 may be set as a temperature higher than a temperature (e.g., 0° C. or less) at which a skin surface or the skin dies.

In an embodiment, the third set temperature Ts3 may be required to be set differently according to each section even in the post-cooling section P3. For example, since the initial section of the post-cooling section P3 is adjacent to the stopping time of the laser emission section, the degree of the increase of the skin surface temperature of the laser emission section may be an important factor to be considered when presetting the third set temperature Ts3 in the initial section of the post-cooling section P3. On the other hand, in a section after the initial section of the post-cooling section P3, a pain minimizing temperature and the temperature of a skin death may be relatively important factors to be considered when setting the third set temperature Ts3. In this case, the third set temperature Ts3 may be set differently even in the post-cooling section P3 since factors to be considered in the initial section and later section of the post-cooling section P3 are different.

In the above, the third set temperature Ts3 has been described to be set relative to the skin surface temperature, but is not limited thereto, and it is clear to those skilled in the art that a specific temperature may be set based on the temperature of a refrigerant which is a direct variable of the skin surface temperature and is controlled by the refrigerant condition control unit 1220.

Referring back to FIG. 8, the laser treatment method may include the determining S4200 of the temperature or spray amount of the refrigerant by considering the skin surface temperature and/or the temperature of the refrigerant measured at S4100. Specifically, the control module 1400 may determine the temperature and/or spray amount of a refrigerant at S4200 by controlling the refrigerant condition control unit 1220 by considering the skin surface temperature and/or the temperature of the refrigerant measured at S4100. Alternatively, the control module 1400 may determine the spray amount of a refrigerant by controlling the amount of the refrigerant supplied to the spraying unit 1230 by controlling the opening/closing cycle and period of opening/closing time of the flow rate control unit 1210 at S4200.

In the spraying of a refrigerant at S4300, a refrigerant may be sprayed according to the temperature or spray amount of the refrigerant determined at S4200.

When a refrigerant is sprayed at S4300, determining S4400 whether a predetermined time elapses after the laser emission stops may be performed.

In the determining S4400 of whether a predetermined time elapses after the laser emission stops, the control module 1400 may determine whether a period of time for which the post-cooling is performed is within the predetermined period of time after the laser emission.

The predetermined time may be set by considering the degree of pain according to treatment type and the degree of the increase of the skin surface temperature in the laser emission section, etc. The predetermined time may mean a period of time for which the post-cooling can be performed, and the period of time of the post-cooling may have a linear relationship with the amount of energy applied to the skin surface and thus may be set by considering the degree of pain according to treatment and the degree of the increase of the skin surface temperature in the laser emission section.

For example, the degree of pain may be different according to treatment type or treatment area, and when the degree of pain is relatively high, the period of time of the post-cooling, that is, a predetermined period of time is set to be relatively long such that the relatively large amount of cooling energy is applied to the skin surface. On the other hand, when the degree of pain is relatively low, the period of time of the post-cooling, that is, a predetermined period of time is set to be relatively short such that the relatively small amount of cooling energy is applied to the skin surface. In other words, the predetermined period of time may be set by considering the degree of pain according to treatment.

The predetermined period of time may be set directly by a user or in such a manner that a user selects a value set by the control module 1400 using treatment information and temperature information stored in the control module 1400. In addition, the predetermined period of time may be set before laser treatment starts (e.g., before the start step of FIG. 5).

When a period of time for which the post-cooling is performed is within a predetermined period of time, the measuring S4100 of a skin surface temperature and the temperature of a refrigerant is performed such that a series of the steps can be performed again.

On the other hand, when a period of time for which the post-cooling is performed passes a predetermined period of time, the control module 1400 may stop the post-cooling.

However, here, the control module 1400 is described to 'determine' whether a predetermined period of time elapses after the laser emission, but is not limited thereto, and when the predetermined period of time elapses after the laser emission, a time-lapse signal is transmitted to the control module 1400, and the control module 1400 may control the laser treatment device 100 such that the post-cooling stops even if the control module does not determine whether the predetermined period of time elapses after the laser emission.

Additionally, in FIG. 8, the post-cooling is illustrated to stop when a predetermined period of time elapses after the laser emission stops, but this is only an example. The post-cooling may stop even through the stop of the input of the spray of a refrigerant by a user.

As described above, it has been mainly described that the control module 1400 determines the temperature or spray amount of a refrigerant by considering the measured temperature and the predetermined third set temperature Ts3 at S4200. However, this is only an example, and according to the embodiment, the control module 1400 may determine whether the measured actual temperature (e.g., the actual temperature of a skin surface and the actual temperature of a sprayed refrigerant) corresponds to 'the condition' of the predetermined third set temperature. In this case, the predetermined third set temperature condition may be a temperature range in which an allowable 'error range' relative to the predetermined third set temperature is preset. Alternatively, the predetermined third set temperature condition may be any suitable condition including a condition in which the skin surface temperature is maintained for a specific period of time relative to a specific temperature value.

When the measured actual temperature (e.g., the actual temperature of a skin surface and the actual temperature of a sprayed refrigerant) corresponds to the predetermined third set temperature condition, the control module 1400 may determine the temperature or spray amount of a refrigerant to be sprayed such that the refrigerant is sprayed by having the temperature or spray amount of a sprayed refrigerant.

When the measured actual temperature (e.g., the actual temperature of a skin surface and the actual temperature of a sprayed refrigerant) does not correspond to the predetermined third set temperature condition, the control module 1400 may control the temperature or amount of a refrigerant through the refrigerant condition control unit 1220. Alternatively, the control module 1400 may control the amount of a refrigerant through the flow rate control unit 1210.

According to the laser treatment method by the laser treatment device 100 disclosed in the present specification, at least two set temperatures of the first set temperature Ts1 in the pre-cooling section P1, the second set temperature Ts2 in the laser emission section, and the third set temperature Ts3 in the post-cooling section P3 may be set to be different. Specifically, factors to be considered in the pre-cooling section P1, the laser emission section, and the post-cooling section P3 may be different. For example, the first set temperature Ts1 may be set by considering the increasing degree of the skin surface temperature of the laser emission section and whether the laser interfering substance of the laser emission section is generated, and the second set temperature may be set by considering a temperature of a target and a desired temperature of a target in the laser emission section, and the skin damage temperature, etc. Additionally, the third set temperature Ts3 may be set by considering a pain minimizing temperature and a skin dying temperature by cooling, etc. In this case, since factors to be considered in each section may be different, the first set temperature Ts1, the second set temperature Ts2, and the third set temperature Ts3 may be set to be different from each other.

For example, the first set temperature Ts1 may be lower than the second set temperature Ts2, and the third set temperature Ts3 may be a temperature between the first set temperature Ts1 and the second set temperature Ts2. Specifically, since the second set temperature Ts2 may correspond to a section in which a skin surface temperature is increased by laser emission, the second set temperature Ts2 may be set to be higher than the first set temperature Ts1 and the third set temperature Ts3. In addition, the first set temperature Ts1 may be set as a temperature lower than the third set temperature Ts3 to maintain the skin surface temperature as low as possible before the laser emission.

For example, the first set temperature Ts1 may be lower than the second set temperature Ts2, and the first temperature Ts1 may be higher than the third set temperature Ts3. Specifically, since the second set temperature Ts2 may correspond to a section in which the skin surface temperature is increased by laser emission, the second set temperature Ts2 may be set to be higher than the first set temperature Ts1 and the third set temperature Ts3. In addition, the first set temperature Ts1 may be set as a temperature (0° C. or more) at which frost is not present on the skin surface during the laser emission, and the third set temperature Ts3 may be set as a temperature lower than 0° C. to restore the skin surface temperature to a normal temperature as soon as possible.

For example, the first set temperature Ts1 may be lower than the second set temperature Ts2 and may be the same as the third set temperature Ts3. Specifically, since the second set temperature Ts2 may correspond to a section in which the skin surface temperature is increased by the laser emission, the second set temperature Ts2 may be set to be higher than the first set temperature Ts1 and the third set temperature Ts3. In addition, the first set temperature Ts1 and the third set temperature Ts3 may be set as any suitable equal temperatures in consideration of the above description.

For example, in the laser emission section, the second set temperature may be set such that the skin surface temperature is close to the second set temperature. However, since high-output energy is applied to the skin surface in the laser emission section, there is possibility that the skin surface temperature is not controlled to the second set temperature. That is, there is the possibility that difference between the actual skin surface temperature and the second set temperature is large. In this example, regardless of the actual skin surface temperature, the second set temperature may be set as low as possible such that the possibility of damage to the skin surface can be minimized. In this case, the second set temperature Ts2 may be lower than the first set temperature Ts1 and/or the third set temperature Ts3.

However, the above description is only an example, and in consideration of the type and objective of a treatment, the first set temperature Ts1, the second set temperature Ts2, and the third set temperature Ts3 may be set. For example, the first set temperature Ts1, the second set temperature Ts2, and the third set temperature may all be set as the same temperatures. For another example, in consideration of the type and objective of a treatment, the first set temperature Ts1 and the second set temperature Ts2 may be set to be the same. For another example, in consideration of the type and objective of a treatment, the second set temperature Ts2 and the third set temperature Ts3 may be set to be the same.

According to the laser treatment method by the laser treatment device 100 disclosed in the present specification, the error range of the first set temperature Ts1 in the pre-cooling section P1, the error range of the second set temperature Ts2 in the laser emission section, and the error range of the third set temperature Ts3 in the post-cooling section P3 may be set. For example, referring back to FIG. 4, in the pre-cooling section P1, the skin surface temperature is set to be controlled to the first set temperature Ts1, and an error range R1 may be set such that the skin surface temperature is maintained within a predetermined temperature range.

In this case, the error ranges may be input directly by a user in a way similar to the set temperatures described above or may be set as any suitable value in the control module 1400.

Additionally, the error ranges may be set to be different according to the pre-cooling section P1, the inter-cooling section P2, and the post-cooling section P3.

For example, in the inter-cooling section P2, the error range may be set by considering the type of a laser, the output of the laser, a skin damage temperature, a desired temperature of a target, and the possibility of skin damage caused by a laser is relatively high, and thus the error range of a set temperature may be set to be narrower than other cooling sections.

On the other hand, the post-cooling section P3 is a cooling section after laser output stops, and the possibility of skin damage due to the increase of a temperature caused by laser treatment may be lower in the post-cooling section than in other cooling sections, and thus an error range related to a set temperature in the post-cooling section P3 may be set to be wider in the post-cooling section P3 than in other cooling sections.

According to the laser treatment method by the laser treatment device 100 disclosed in the present specification, since the set temperature of a skin surface may be suitably set in consideration of treatment situation and temperature situation in each of the pre-cooling section P1, the laser emission section, and the post-cooling section P3, customized treatment can be performed for each treatment situation and each temperature situation, and more efficient cooling can be performed. Particularly, in the pre-cooling section P1, a skin surface temperature may be decreased before laser emission such that the possibility of skin damage due to temperature rise in the laser emission section is prevented, and in the laser emission section, the skin surface temperature may be controlled to a skin damage temperature or less such that the possibility of skin damage is minimized. In addition, in the post-cooling section P3, the skin surface temperature may be controlled to a temperature at which pain can be minimized such that pain due to treatment is minimized. Additionally, in the laser emission section, the temperature and/or amount of a refrigerant may be controlled in relation to the laser emission such that the temperature of a target reaches the desired temperature of a target while the skin surface temperature is maintained to be the skin damage temperature or less. Accordingly, it is possible to achieve the objective of target treatment and the objective of the present specification to minimize the possibility of skin damage and pain, based on the above.

Figure 9:
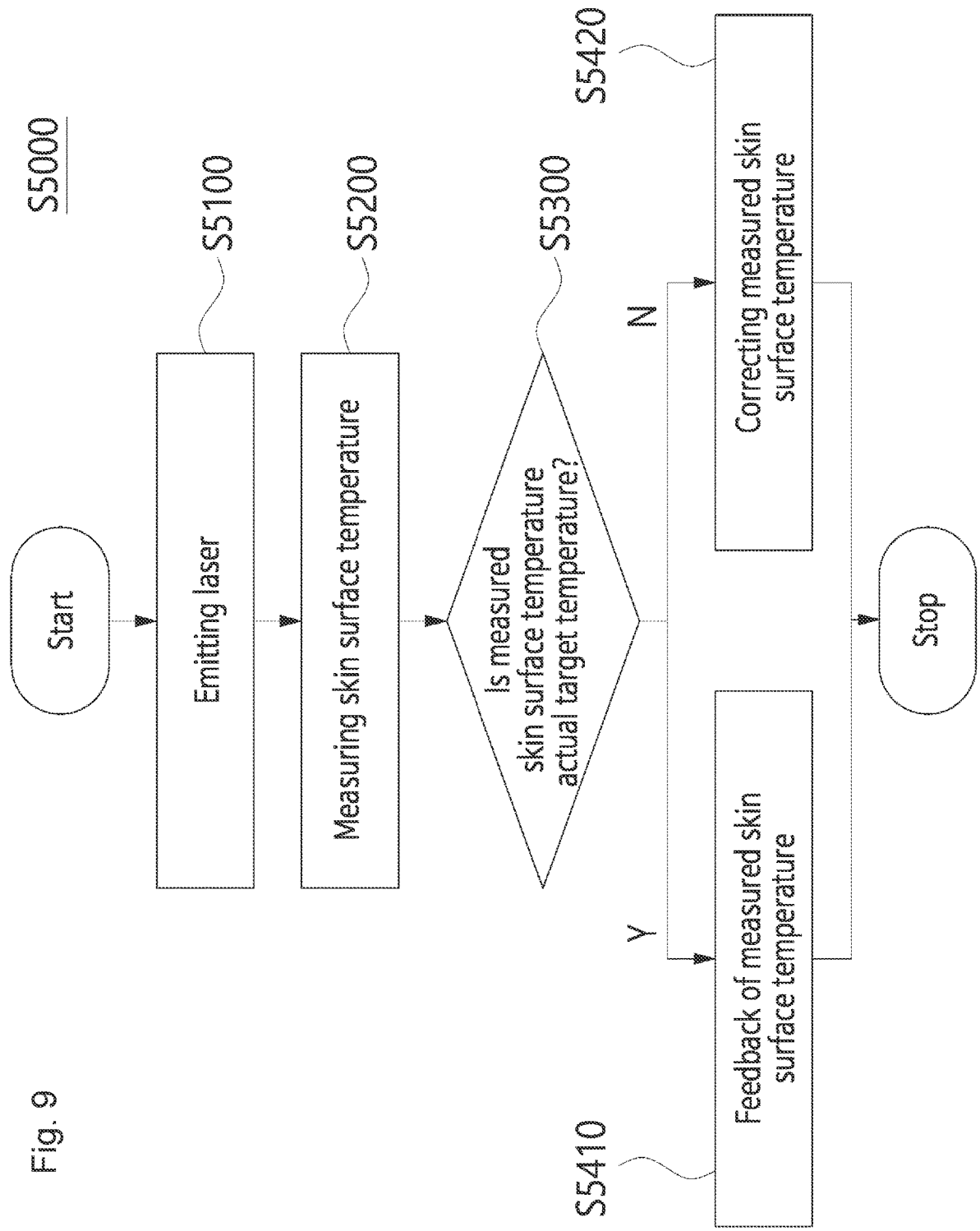
FIG. 9 is a flowchart illustrating a correction method of the skin surface temperature measured according to the embodiment of the laser treatment method disclosed in the present specification.

When measuring a skin temperature during laser irradiation, an error may occur. Specifically, in the laser emission section, when the sensing unit 1300 detects a temperature of a skin surface while the skin surface is irradiated with a laser, the output of the laser is significantly large, and thus the detection of the skin surface temperature by the sensing unit 1300 may interfere with the laser. Accordingly, when measuring a skin temperature in the laser emission section, a measured skin temperature may have an error. Hereinafter, referring to FIG. 9, the driving method of the laser treatment device for minimizing the error of the measured skin temperature in the laser emission section will be described. FIG. 9 is a flowchart 55000 illustrating the method of correcting the measured skin surface temperature according to the embodiment of the laser treatment method disclosed in the present specification.

Referring to FIG. 9, the driving method of the laser treatment device 100 disclosed in the present specification may include: emitting a laser at 55100; measuring a skin surface temperature at 55200; and determining whether a measured skin surface temperature is an actual skin surface temperature at 55300. In this case, when the measured skin surface temperature is the actual skin surface temperature, temperature feedback may be performed at 55410 by controlling the temperature and/or amount of a refrigerant based on the measured skin surface temperature. On the other hand, when it is determined that the measured skin surface temperature is not the actual skin surface temperature, the correcting of the measured skin surface temperature may be performed at S5420.

Hereinafter, as the method of correcting the measured skin surface temperature at S5420, the method of correcting an error or reducing the possibility of the error is proposed.

In an embodiment, by using the method of correcting and estimating data on a skin surface temperature measured by the sensing unit 1300 at the same time as laser emission time, the accuracy of temperature feedback due to the error of a measured temperature can be improved. Specifically, by using data on a skin surface temperature caused by laser emission, which is accumulated by a conventional treatment, the correction and/or estimation of data on the skin surface temperature measured by the sensing unit 1300 may be performed such that a difference between the data on skin surface temperature measured by the sensing unit 1300 at the same time as laser emission time and data on an actual skin surface temperature is small. For example, based on data on the change of a skin surface temperature due to laser emission, which is accumulated by the conventional treatment, tendency to the change of the skin surface temperature due to the laser emission can be analyzed, and to conform to the tendency of the skin surface temperature change, data on the skin surface temperature with a high possibility of error can be corrected and/or estimated. By correcting and/or estimating the data on the skin surface temperature with a high possibility of error to suitable temperature data, the accuracy of the temperature feedback can be improved.

When measuring a skin surface temperature by using the sensing unit during laser emission, difference between the measured skin surface temperature and the actual skin surface temperature may occur under the influence of a laser.

In an embodiment, to reduce such an error, the cycle of temperature measurement by the sensing unit 1300 may be set in consideration of a relation with a laser emission cycle. For example, when a laser is emitted, the laser may be output at a predetermined cycle, and in this case, the cycle of the temperature measurement of a skin surface by the sensing unit 1300 may be set to be different from the laser output cycle such that the error of the measured skin surface temperature can be prevented or reduced.

For example, the temperature measurement cycle of the sensing unit 1300 may be set to be shorter than a laser emission cycle. When the temperature measurement cycle of the sensing unit 1300 is set to be shorter than the laser emission cycle, the number of the measuring times of the temperature of a skin surface on which an error is highly likely to occur due to the influence of a laser is different from the number of measuring times of the temperature of a skin surface on which an error is not highly likely to occur and thus distinction therebetween is easy. Through this, the measured temperature (e.g., a skin surface temperature measured at the same time as the laser emission time) of the skin surface on which an error is highly likely to occur due to the influence of the laser is excluded or corrected from data, so the accuracy of temperature feedback according to the error of the measured temperature can be improved.

Here, the temperature measurement cycle of the sensing unit 1300 is described to be set shorter than the laser emission cycle, but is not limited thereto. The temperature measurement cycle is set as the same cycle as or a longer cycle than the laser emission cycle, and temperature data of time at which the laser emission time and temperature measurement time are the same is excluded or corrected such that the accuracy of the temperature feedback according to the error of the measured temperature can be improved.

For example, the sensing unit 1300 may be configured to randomly measure a skin surface temperature. Specifically, irrespective of time and cycle at which a laser is output, the sensing unit 1300 randomly measures the skin surface temperature, and thus it is possible to reduce the probability that the sensing unit 1300 measures the skin surface temperature at the same time as the output time of the laser. Through this, the possibility of the error of the measured temperature of the skin surface is decreased, and thus the accuracy of the temperature feedback can be improved.

Additionally, when measuring a skin surface temperature by using the sensing unit during laser emission, difference between the measured skin surface temperature and the actual skin surface temperature may occur under the influence of a laser. To reduce this error, only measured temperature data at desired time may be selectively filtered.

For example, the sensing unit 1300 continuously measures a skin surface temperature, and among measured temperature data, temperature data measured at laser emission time may be excluded and only temperature data measured at time other than the laser emission time may be selectively filtered. The filtering may be implemented through an external device or may be implemented in the control module 1400. The accuracy of the temperature feedback can be improved by filtering temperature data with a high possibility of error.

When measuring a skin surface temperature by using the sensing unit during laser emission, difference between measured skin surface temperature and an actual skin surface temperature may occur under the influence of a laser.

In an embodiment, to prevent the error of temperature measurement by the sensing unit 1300 due to interference with a laser, a filter which selectively blocks only the wavelengths of a laser used in treatment may be used. Specifically, the sensing unit 1300 for measuring a skin surface temperature may be configured as an infrared temperature sensing unit, and during laser emission, laser light or light partially reflected by a laser on a skin surface may interfere the infrared temperature sensing unit. In this case, a filter that can filter a laser wavelength band or a wavelength band of laser light reflected on the skin surface may be attached to the infrared temperature sensing unit. Through this, it is possible to minimize the temperature measurement error of the sensing unit 1300 due to laser or laser reflected light. In other words, a filter (e.g., an infrared radiation filter) may be attached to the sensing unit 1300 such that light of a specific wavelength does not pass through the filter, and through this, in temperature measurement by the sensing unit 1300, a temperature measurement error due to the interference of a laser and/or a laser reflected light can be minimized.

According to the driving method of the laser treatment device 100 disclosed in the present specification in which the error of the temperature measurement of a measured skin surface is prevented, the temperature measurement function of the sensing unit 1300 may not be used in a laser emission section. Specifically, in the laser emission section, the measurement of a skin surface temperature may interfere with a laser, and in this case, performing temperature feedback by measuring the skin surface temperature may not be efficient. Accordingly, in the laser emission section, the measurement of the skin surface temperature of the sensing unit 1300 may not be performed. However, the laser emission section is a section with high possibility of skin damage, and thus hereinafter, even if the temperature measurement of the sensing unit 1300 is not performed, an additional method for preventing skin damage is proposed.

In an embodiment, according to the driving method of the laser treatment device 100 disclosed in the present specification, in the laser emission section, it is possible to spray a refrigerant to be sprayed on a skin surface by setting the amount of the refrigerant to a fixed value regardless of a skin surface temperature. Specifically, in the laser emission section, the sensing unit 1300 may be configured such that the sensing unit 1300 does not perform the measurement of a skin surface temperature. To prevent damage to skin surface from thermal energy by a laser even in the laser emission section, a refrigerant may be sprayed on the skin surface by setting the amount of the refrigerant to a fixed value. In this case, the set value of the amount of a refrigerant may be a value considered such that the skin surface temperature does not reach a skin damage temperature based on treatment information and temperature information stored in the control module 1400.

In an embodiment, according to the driving method of the laser treatment device 100 disclosed in the present specification, in the laser emission section, it is possible to spray a refrigerant on a skin surface by setting the temperature of the refrigerant to a fixed value regardless of a skin surface temperature. Specifically, in the laser emission section, the sensing unit 1300 is configured such that the sensing unit 1300 does not measure the skin surface temperature. To prevent damage to skin surface from thermal energy by a laser even in the laser emission section, the temperature of a sprayed refrigerant may be set to a fixed value, and the refrigerant may be sprayed on the skin surface by having a specific temperature value. Since the temperature of the refrigerant is a direct variable of the skin surface temperature, a refrigerant may be sprayed by having a specific temperature such that the skin surface temperature can be controlled. In this case, the preset value of the temperature of the refrigerant may be a value considered such that the skin surface temperature does not reach a skin damage temperature based on treatment information and temperature information stored in the control module 1400.

In an embodiment, according to the driving method of the laser treatment device 100 disclosed in the present specification, in the laser emission section, the refrigerant condition control unit 1220 may be operated by fixing the value of the amount of thermal energy applied to a refrigerant regardless of a skin surface temperature. Specifically, in the laser emission section, the sensing unit 1300 may be configured such that the sensing unit 1300 does not measure the skin surface temperature. To prevent damage to a skin surface from thermal energy by a laser even in the laser emission section, the refrigerant condition control unit 1220 may fix the value of the amount of the thermal energy applied to a refrigerant. To this end, by fixing a current applied to the refrigerant condition control unit 1220, power applied to the refrigerant condition control unit 1220 may be fixed. In this case, at least one of a current value applied to the refrigerant condition control unit 1220, a power value applied to the refrigerant condition control unit 1220, and a value of the amount of thermal energy applied to a refrigerant may be a value considered such that the skin surface temperature does not reach a skin damage temperature based on treatment information and temperature information stored in the control module 1400.

In the above, it has been mainly described that in the laser emission section, the sensing unit 1300 does not perform the measurement of the skin surface temperature, but while the sensing unit 1300 measures the skin surface temperature in the laser emission section, the fixing of the amount of a refrigerant by the refrigerant condition control unit, the fixing of the temperature of a refrigerant by the refrigerant condition control unit, and the fixing of the amount of the thermal energy applied to a refrigerant by the refrigerant condition control unit, which have been described above, may be used in combination with each other, and it is clear to those skilled in the art that through this combination, it is possible to achieve the objective of the present disclosure for controlling the skin surface temperature not to exceed the skin damage temperature in the laser emission section.

In the driving method of the laser treatment device 100 disclosed in the present specification, in order to minimize the possibility of damage to the skin surface while preventing the occurrence of errors in the skin surface temperature measured by the sensing unit 1300, the changes of the skin surface temperature and the temperature of a target in the laser emission section may be estimated, based on the treatment information and/or temperature information obtained through a conventional treatment. Specifically, the control module 1400 may be configured to estimate and/or predict temperature change in the laser emission section based on a skin surface temperature, the temperature of a target, and the temperature of a refrigerant obtained in the conventional treatment using substantially the same treatment information as treatment information such as a treatment area in which treatment will be performed, and a laser type.

In the embodiment, when performing treatment by spraying a refrigerant on a skin surface such that the temperature and amount of the refrigerant have specific values at the same time as time at which a laser is emitted in the laser emission section of the conventional treatment, the control module 1400 may analyze the change and tendency of temperature information including a skin surface temperature and/or the temperature of a target based on treatment information and temperature information obtained from the conventional treatment. In this case, the control module 1400 may analyze information such as the temperature and amount of a refrigerant, a laser type, and a treatment area, and the connection of the same with the change of the skin surface temperature and/or the temperature of a target. Additionally, when substantially the same treatment as the conventional treatment is performed, the control module 1400 may estimate and predict a skin surface temperature and the temperature of a target and may control the temperature and/or amount of a refrigerant such that the spraying of a refrigerant is controlled. In this case, the control module 1400 may be configured to control the temperature and/or amount of a refrigerant such that the skin surface temperature does not reach a skin damage temperature and the temperature of a target reaches the desired temperature of a target.

In an embodiment, based on the skin surface temperature and/or the temperature of a target of a conventional treatment that is substantially the same as a treatment to be performed, the control module 1400 may be configured to control the temperature and amount of a refrigerant to be sprayed. Particularly, based on the skin surface temperature and/or the temperature of a target of the starting time of the laser emission of the conventional treatment and the skin surface temperature and/or the temperature of a target of the stopping time of the laser emission thereof, the control module 1400 may be configured to control the temperature and amount of a refrigerant to be sprayed. In this case, the control module 1400 may be configured to control the temperature and/or amount of a refrigerant such that the skin surface temperature does not reach the skin damage temperature and the temperature of a target reaches the desired temperature of a target.

In an embodiment, the treatment of irradiating one target with a plurality of lasers may be performed. In this case, it is possible to control the temperature and/or amount of a sprayed refrigerant at the second shot by using skin information obtained by the first shot. This will be described in detail later.

In an embodiment, the treatment of irradiating a plurality of targets with a laser on may be performed. In this case, the temperature and/or amount of a refrigerant sprayed on a second spot may be controlled by using temperature information of a first spot. This will be described in detail later.

The laser treatment device disclosed in the present specification 100 may include: the laser module which outputs a laser to a patient's skin for laser treatment; the sensing unit which measures the temperature of the skin; the nozzle which sprays a refrigerant on the skin; the refrigerant condition control unit which controls at least one of the temperature and spray amount of the refrigerant; and the control module configured to control at least one of the temperature and amount of the refrigerant based on at least one of the first skin information and the second skin information when performing the laser treatment of the second shot after the laser treatment of the first shot after obtaining at least one of the first skin information and the second skin information through the sensing unit, the first skin information including at least a skin temperature when or before the laser output of the first shot starts, and the second skin information including at least a skin temperature when or after the laser output of the first shot stops.

Here, the first skin information or the second skin information is a concept including a skin type, a skin treatment area, a skin temperature, and any suitable information related to the skin, but hereinafter, the embodiment of information on a skin temperature will be mainly described.

The first skin information may be the skin temperature when or before the laser output of the first shot starts, and the second skin information may be the skin temperature when or after the laser output of the first shot stops.

When performing the laser treatment of the second shot after the laser treatment of the first shot, the control module 1400 of the laser treatment device 100 may be configured to control at least one of the temperature and amount of the refrigerant based on at least one of the first skin information and the second skin information.

According to the embodiment, the first skin information may indicate a skin temperature detected at substantially the same time as time at which the output of the laser starts, and the second skin information may indicate a skin temperature detected at substantially the same time as time at which the output of the laser stops. In this case, when performing the laser treatment of the second shot after the laser treatment of the first shot, the control module 1400 may be configured to control at least one of the temperature and amount of the refrigerant in least a portion of the emission section of the laser based on at least one of the first skin information and the second skin information.

According to the embodiment, when performing the laser treatment of the second shot after the laser treatment of the first shot, the control module 1400 may be configured to control at least one of the temperature and amount of a refrigerant based on 'difference' between the first skin information and the second skin information.

According to the embodiment, when performing the laser treatment of the second shot after the laser treatment of the first shot, the control module 1400 may be configured to control at least one of the temperature and amount of a refrigerant based on a temperature detected from a skin surface which is irradiated with the second shot in a remaining cooling section except for the laser emission section of the second shot. In other words, the control module 1400 may be configured to control at least one of the temperature and amount of a refrigerant in at least a portion of the emission section of the laser based on the first skin information and/or the second skin information related to the first shot in the laser emission section, and may be configured to control at least one of the temperature and amount of a refrigerant based on a temperature detected from a skin surface on which the second shot will be irradiated or is irradiated in the pre-cooling section P1 and/or the post-cooling section P3 except for the laser emission section.

According to the embodiment, the laser output of the first shot and the second shot may be performed to the same target. For example, when the laser of the first shot is output to the first spot, the laser of the second shot may also be output to the first spot. In other words, the laser output of the first shot and the laser output of the second shot may be performed to substantially the same position of the skin.

According to the embodiment, the laser output of the first shot and the second shot may be performed to different targets. For example, when the laser of the first shot is output to the first spot, the laser of the second shot may be output to the second spot. In other words, the first shot is a laser output to the first position of the skin, and the second shot may be a laser output to the second position of the skin different from the first position.

According to the embodiment, the driving method of the laser treatment device 100 disclosed in the present specification may include performing a plurality of laser shots on one target.

According to the embodiment, the driving method of the laser treatment device 100 disclosed in the present specification may further include performing one laser shot on a plurality of targets.

According to the embodiment, the driving method of the laser treatment device 100 disclosed in the present specification may include performing a plurality of laser shots on a plurality of targets, respectively.

Here, one laser shot may mean outputting one pulse. In addition, a plurality of laser shots may generally mean outputting a plurality of pulses. However, there may be a case in which a plurality of short pulses are continuously output at intervals of a very short time unit (e.g., nanosecond time unit), and in this case, one laser shot may mean encompassing a plurality of continuously output pulses.

Through this operation and implementation method, at least the measurement error of the skin surface temperature of the laser emission section may be prevented, and the possibility of skin damage may be minimized. Hereinafter, the above-described operation and implementation method will be described in more detail.

Figure 10:
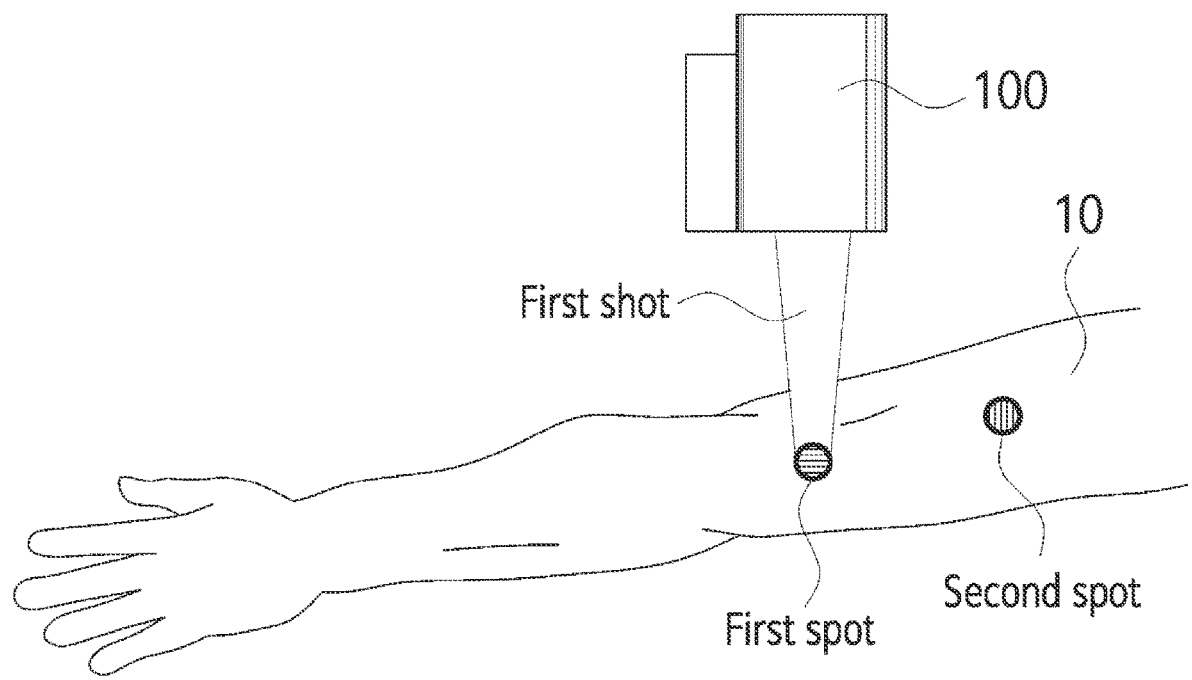
FIG. 10 is a view illustrating the laser irradiation on a first spot by a first shot.
Figure 11:
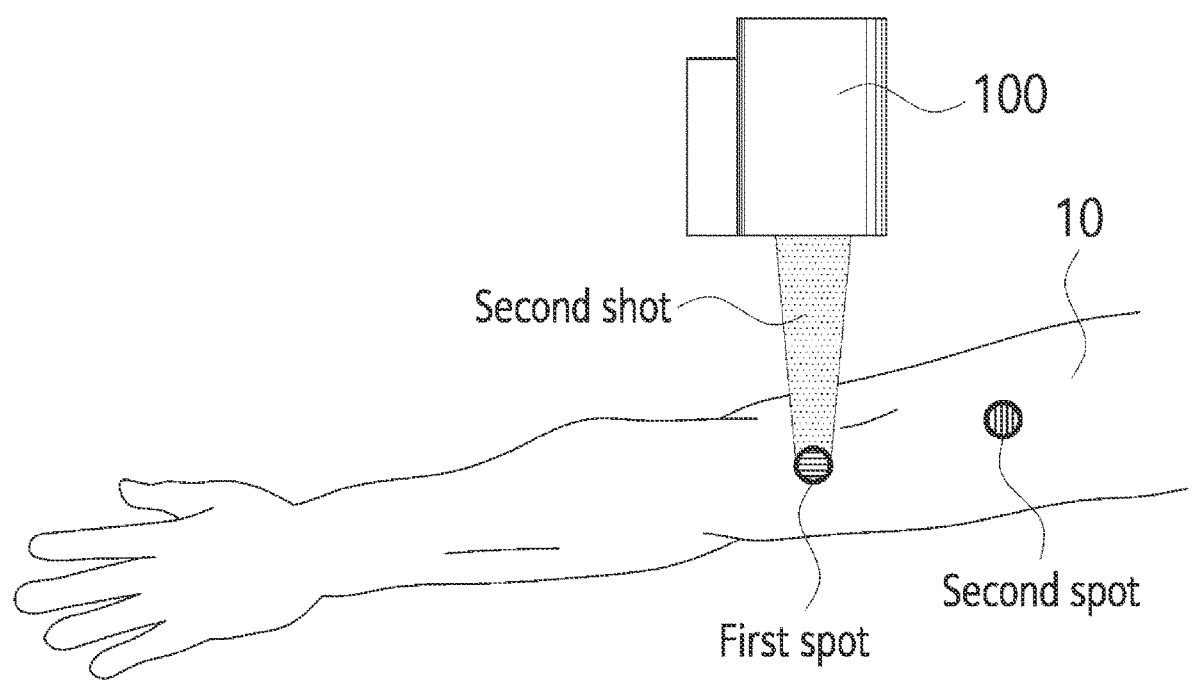
FIG. 11 is a view illustrating laser irradiation of a second shot on the first spot after a predetermined time from when the laser irradiation of the first shot on the first spot is completed.
Figure 12:
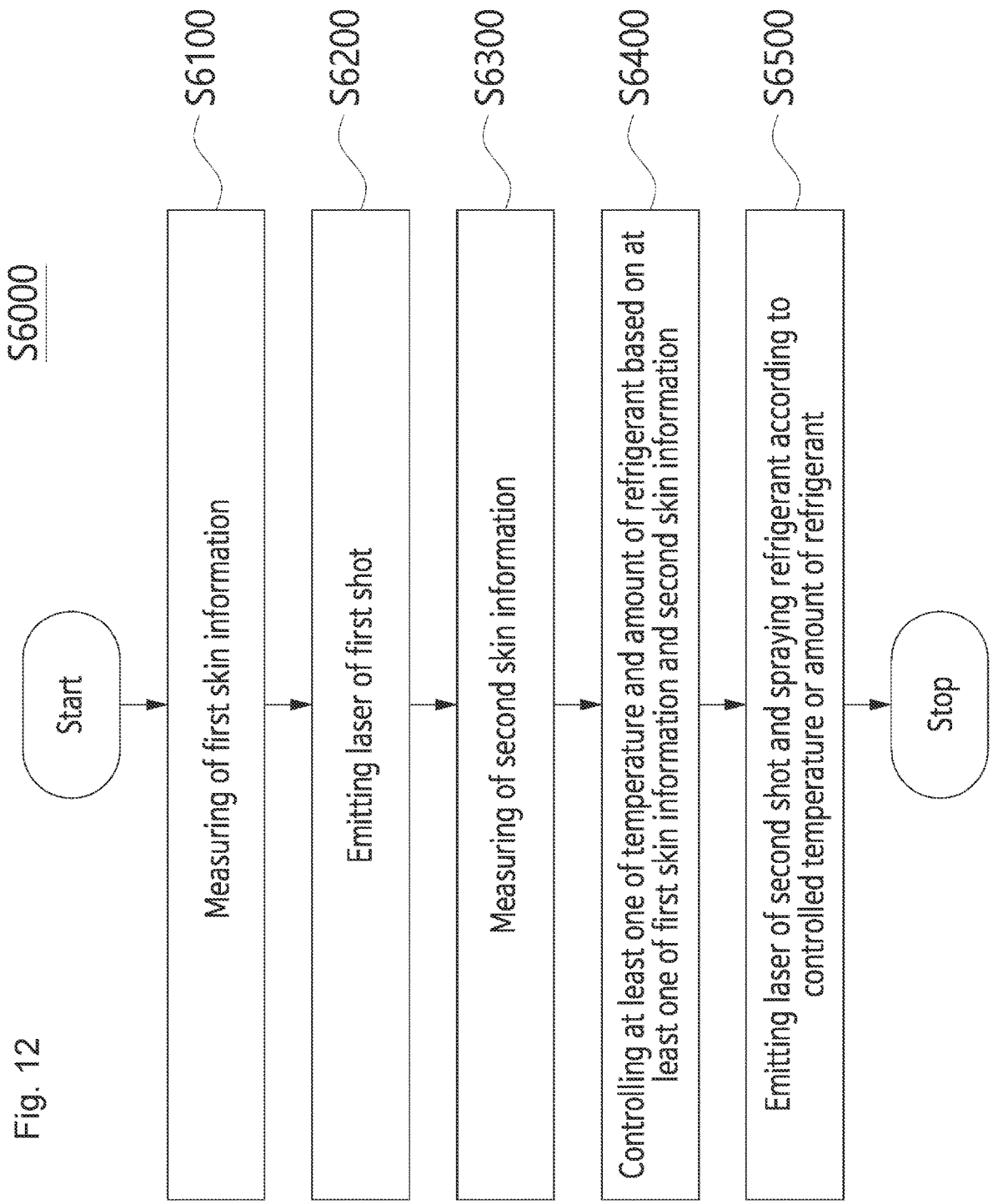
FIG. 12 is a flowchart illustrating the driving method of the laser treatment device when lasers of a plurality of shots on the first spot.

The following will be described with reference to FIGS. 10 to 12. FIG. 10 is a view illustrating laser irradiation on the first shot. FIG. 11 is a view illustrating the laser irradiation of the second shot on the first spot after a predetermined period of time elapses after the completion of the laser irradiation of the first shot on the first spot. FIG. 12 is a flowchart illustrating the driving method S6000 of the laser treatment device when performing a plurality of laser shots on the first spot.

The driving method of the laser treatment device 100 disclosed in the present specification may include: measuring first skin information at S6100 when laser treatment starts; emitting a laser of the first shot at S6200; measuring second skin information at S6300; controlling at least one of the temperature and amount of a refrigerant based on at least one of the first skin information and the second skin information at S6400; and spraying the refrigerant according to the laser emission of the second shot and the controlled temperature or amount of the refrigerant at S6500.

According to the embodiment, in the measuring of the first skin information at S6100, skin information of the skin surface of a target to receive a laser treatment or an area adjacent to the skin surface may be detected by the sensing unit 1300.

The first skin information may be detected when or before the output of a laser starts. Preferably, the first skin information may be skin information detected at substantially the same time as time at which the output of a laser starts.

The first skin information may be the temperature of the skin surface of a target to receive a laser treatment or 'a skin temperature' of an area adjacent to the skin surface. For example, the first skin information may be a skin surface temperature before a laser is output and thermal energy thereof is applied to a skin surface. However, the first skin information is not limited to the skin surface temperature, and may include a patient's skin type and treatment area, and the position and/or depth of the target. For example, in the case of treatment for hair removal, information on the characteristics (e.g., moisture and sensitivity, etc.) of the skin on which the hair is located and skin information on the location or depth of the target are measured, and the information may be used during the laser emission of the second shot.

According to the embodiment, the first skin information may be detected at time before the starting time of the output of the laser. In this case, at time before the starting time of the output of the laser, the pre-cooling may be performed. When the pre-cooling is performed, in addition to the first skin information, information on the temperature and/or amount of a sprayed refrigerant in the pre-cooling may be obtained and may be used to control the temperature and/or amount of a refrigerant to be sprayed during the laser emission of the second shot to be described later.

In the laser emission of the first shot at S6200, the laser module 1100 may output a laser to a treatment target. Preferably, the emission of the laser of the first shot may be intended to obtain skin information for precisely controlling the temperature and/or amount of a refrigerant to be sprayed together when emitting the laser of the second shot. In other words, the emission of the laser of the first shot may be intended to control the temperature and/or amount of a refrigerant such that the skin surface temperature does not reach the skin damage temperature during the laser treatment of the second shot based on skin information obtained at the emission starting time and emission stopping time of the laser emission section of the first shot.

According to the embodiment, in the measuring of the second skin information at S6300, the second skin information may be detected by the sensing unit 1300 in the same skin surface area as a skin surface area in which the first skin information is measured. That is, the second skin information on the skin surface of a target to receive a treatment by a laser or an area adjacent to the skin surface may be measured.

The second skin information may be detected when or after a laser output is completed. Preferably, the second skin information may be skin information detected at substantially the same time as time at which the laser output stops.

The second skin information may be 'a skin temperature' of the skin surface of a target to receive a treatment by a laser or an area adjacent to the skin surface. For example, the second skin information may be a skin surface temperature after thermal energy is applied to a skin surface after a laser output stops. However, the second skin information is not limited to the skin surface temperature and may include a laser type (laser wavelength and output) and laser emission time, etc. in the laser emission section.

According to the embodiment, the second skin information may be detected at time when or after a laser output stops. In this case, in the laser emission section, in addition to the output of a laser, a refrigerant may be sprayed. That is, the inter-cooling may be performed. When the inter-cooling is performed, information on the temperature and/or amount of a sprayed refrigerant may be additionally obtained in the inter-cooling. In addition, information on the change of skin surface temperature according to the temperature and/or amount of a sprayed refrigerant may also be obtained in the inter-cooling. The temperature of a refrigerant, information on the amount of a refrigerant, and/or the information on the change of the skin surface temperature in the inter-cooling may be used to control the temperature and/or amount of a refrigerant to be sprayed before, during, or after the laser emission of the second shot to be described later.

In the controlling of at least one of the temperature and amount of a refrigerant at S6400 based on at least one of the first skin information and the second skin information, the control module 1400 may control at least one of the temperature and amount of a refrigerant to be sprayed during the laser emission of the second shot based on at least one of the first skin information and the second skin information which are detected. In this case, the control module 1400 may control the temperature and/or amount of the refrigerant to be sprayed during the laser emission of the second shot by controlling the amount of thermal energy applied to the refrigerant through the refrigerant condition control unit 1220. Alternatively, the control module 1400 may control the amount of a refrigerant to be sprayed during the laser emission of the second shot by controlling the period of opening/closing time and/or the opening/closing cycle of the flow rate control unit 1210.

In the controlling of at least one of the temperature and amount of a refrigerant based on at least one of the first skin information and the second skin information at S6400, a skin surface temperature may be controlled to the temperature of a skin damage temperature or less during the emission of the second shot by controlling at least one of the temperature and amount of a refrigerant to be sprayed during the laser emission of the second shot. Accordingly, the possibility of skin damage can be minimized.

For example, in the controlling at least one of the temperature and amount of the refrigerant based on at least one of the first skin information and the second skin information at S6400, the temperature and/or amount of a refrigerant to be sprayed during the laser emission of the second shot may be controlled based on the first skin information.

For example, the temperature and/or amount of a refrigerant to be sprayed during the laser emission of the second shot may be controlled based on 'a skin surface temperature' of a treatment area at starting time of the laser emission of the first shot. When the skin surface temperature is relatively high, the skin surface temperature is highly likely to reach a skin damage temperature due to the increase of the skin surface temperature by heat accumulation by a laser, and thus a refrigerant to be sprayed during the laser emission of the second shot may be controlled to be sprayed by having relatively low temperature or in a relatively large amount.

On the other hand, when the skin surface temperature is relatively low, the skin surface temperature is less likely to reach the skin damage temperature due to the increase of the skin surface temperature due to heat accumulation by a laser, and thus a refrigerant to be sprayed during the laser emission of the second shot is controlled to be sprayed by having a relatively high temperature or in a relatively low amount, so it is possible to reduce the power consumption of the refrigerant condition control unit 1220 and to save a refrigerant.

For example, in the controlling of at least one of the temperature and amount of a refrigerant based on at least one of the first skin information and the second skin information at S6400, the temperature and/or amount of a refrigerant to be sprayed during the laser emission of the second shot may be controlled based on 'the second skin information'.

For example, based on 'the skin surface temperature' of a treatment area at substantially the same time as the stopping time of the laser emission of the first shot, the temperature and/or amount of a refrigerant to be sprayed during the laser emission of the second shot may be controlled. When the skin surface temperature is the skin damage temperature or higher or is a temperature relatively close to the skin damage temperature at substantially the same time as the stopping time of the laser emission, it means that the possibility of skin damage is high due to the laser emission, and thus a refrigerant to be sprayed during the laser emission of the second shot may be controlled to be sprayed by having a relatively low temperature or in a relatively large amount. Accordingly, it is possible to minimize the possibility of skin damage On the other hand, when the skin surface temperature is not relatively close to the skin damage temperature, it means that the skin surface temperature is less likely to reach the skin damage temperature due to the increase of the skin surface temperature due to heat accumulation by a laser, and thus a refrigerant to be sprayed during the laser emission of the second shot is controlled to be sprayed by having a relatively high temperature or in a relatively low amount, so it is possible to reduce the power consumption of the refrigerant condition control unit 1220 and to save a refrigerant.

For example, in the controlling of at least one of the temperature and amount of a refrigerant based on at least one of the first skin information and the second skin information at S6400, the temperature and/or amount of a refrigerant to be sprayed during the laser emission of the second shot may be controlled based on the first skin information and the second skin information. In some examples, in the controlling of at least one of the temperature and amount of a refrigerant based on at least one of the first skin information and the second skin information at S6400, the temperature and/or amount of a refrigerant to be sprayed during the laser emission of the second shot may be controlled based on 'difference' between the first skin information and the second skin information.

For example, in the controlling of at least one of the temperature and amount of a refrigerant based on at least one of the first skin information and the second skin information at S6400, based on 'difference' between the skin surface temperature of a treatment area at substantially the same time as the starting time of the laser emission of the first shot and the skin surface temperature of the treatment area at substantially the same time as the stopping time of the laser emission of the first shot, the temperature and/or amount of a refrigerant to be sprayed during the laser emission of the second shot may be controlled. That is, based on difference between the skin surface temperatures at the starting time and stopping time of the laser emission of the first shot, the temperature and/or amount of a refrigerant to be sprayed during the laser emission of the second shot may be controlled. When difference between the skin surface temperatures is relatively large, it may be interpreted to mean that the skin surface temperature at the starting time is greatly increased by the laser emission and is highly likely to reach the skin damage temperature. Accordingly, in this case, a refrigerant to be sprayed during the laser emission of the second shot may be controlled to be sprayed by having a relatively low temperature or in a relatively large amount. Accordingly, it is possible to minimize the possibility of skin damage.

On the other hand, when difference between the skin surface temperatures is relatively small, it may be interpreted to mean that the skin surface temperature at the starting time is increased in a small amount by the laser emission and is less likely to reach the skin damage temperature. Accordingly, in this case, a refrigerant to be sprayed during the laser emission of the second shot may be controlled to be sprayed by having a relatively high temperature or in a relatively small amount. Accordingly, it is possible to reduce the power consumption of the refrigerant condition control unit 1220 and to save a refrigerant.

In the controlling of at least one of the temperature and amount of a refrigerant based on at least one of the first skin information and the second skin information at S6400, at least one of the temperature and amount of a refrigerant may be controlled in additional consideration of difference between the stopping time of the first shot and the starting time of the second shot.

For example, when difference between the stopping time of the first shot and the starting time of the second shot is relatively large, thermal energy transmitted to a skin surface by the laser emission of the first shot is highly likely to be distributed to surrounding tissues. On the other hand, when the difference between the stopping time of the first shot and the starting time of the second shot is relatively small, thermal energy remaining in the skin surface due to the laser emission of the first shot may be relatively high, and due to the laser emission of the second shot, additional thermal energy may be accumulated in the skin surface, so the skin surface temperature may be relatively more likely to reach the skin damage temperature. Accordingly, when the time difference is relatively small, a refrigerant to be sprayed during the laser emission of the second shot may be controlled to be sprayed by having a relatively low temperature or in a relatively large amount.

In the spraying of a refrigerant according to the laser emission of the second shot and the controlled temperature or amount of a refrigerant at S6500, a refrigerant may be sprayed on a treatment area according to the temperature and/or amount of a refrigerant controlled in the controlling of at least one of the temperature and amount of a refrigerant based on at least one of the first skin information and the second skin information at S6400. In this case, the spraying of a refrigerant may be performed in at least a portion of the laser emission section of the second shot. That is, a refrigerant is sprayed according to the controlled temperature or amount of the refrigerant, and thus the inter-cooling may be performed during the laser emission of the second shot. Additionally, through this cooling, a skin surface temperature in the laser emission section of the second shot may be controlled not to reach the skin damage temperature.

However, the control of a refrigerant is not limited to the inter-cooling, and according to the controlled temperature or amount of a refrigerant, 'the pre-cooling' before the laser emission of the second shot and/or 'the post-cooling' after the laser emission of the second shot may be performed and thus it is possible to achieve the objective of the present disclosure for minimizing the possibility of skin damage and pain. In other words, in the above, the inter-cooling in which at least one of the temperature and amount of a refrigerant is controlled based on the first skin information and/or the second skin information of the first shot has been mainly described, but the control of a refrigerant is not limited to the inter-cooling, and at least one of the temperature and amount of a refrigerant to be sprayed may be controlled in the pre-cooling and/or the post-cooling of the second shot based on the first skin information and/or the second skin information of the first shot.

In the above, the treatment of performing a plurality of laser shots on one target has been described, but the above description is not limited to the performing of a plurality of laser shots on one target, and may be inferred and applied even to the irradiation of plurality of targets with a laser, which will be described later, in the same or similar manner. Hereinafter, the characteristics of laser treatment on a plurality of targets will be mainly described.

Figure 13:
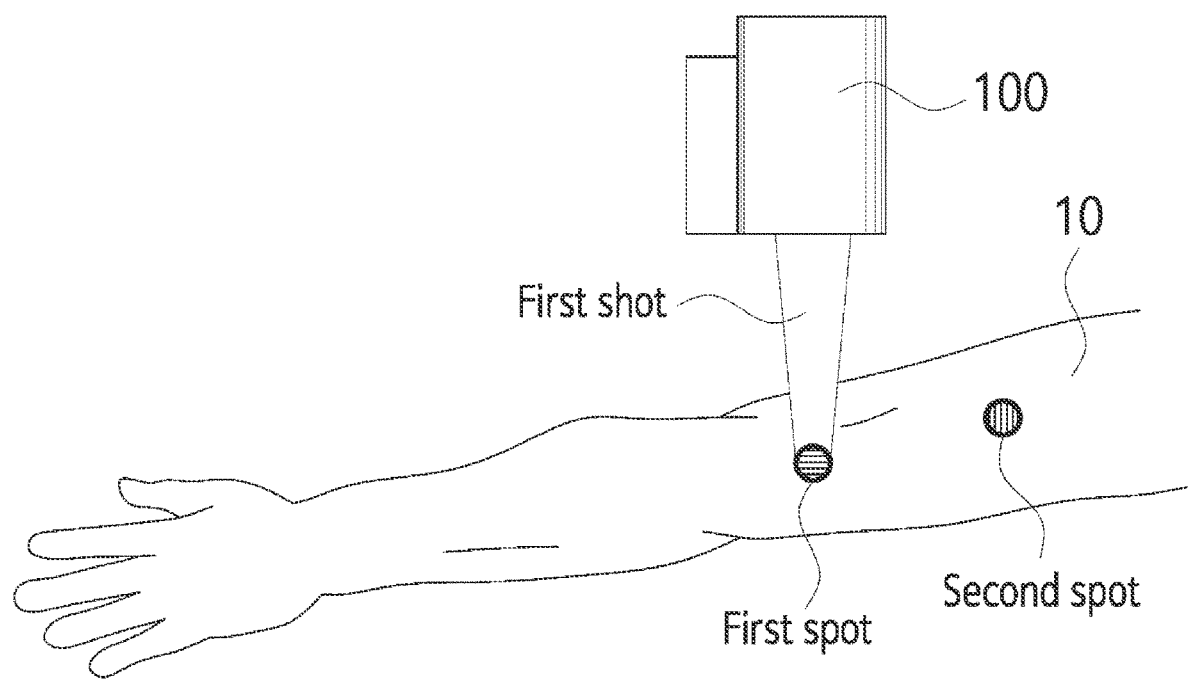
FIG. 13 is a view illustrating laser irradiation on the first spot.
Figure 14:
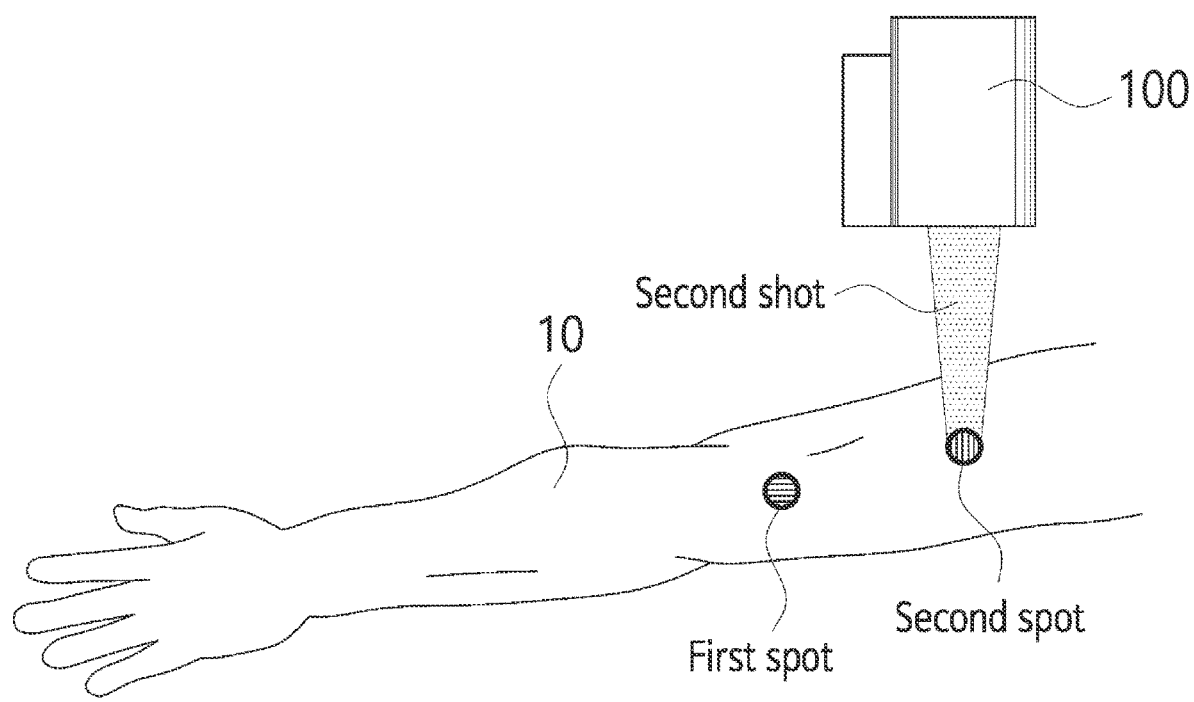
FIG. 14 is a view illustrating laser irradiation on a second spot after a predetermined time elapsed from when the laser irradiation on the first spot is completed.
Figure 15:
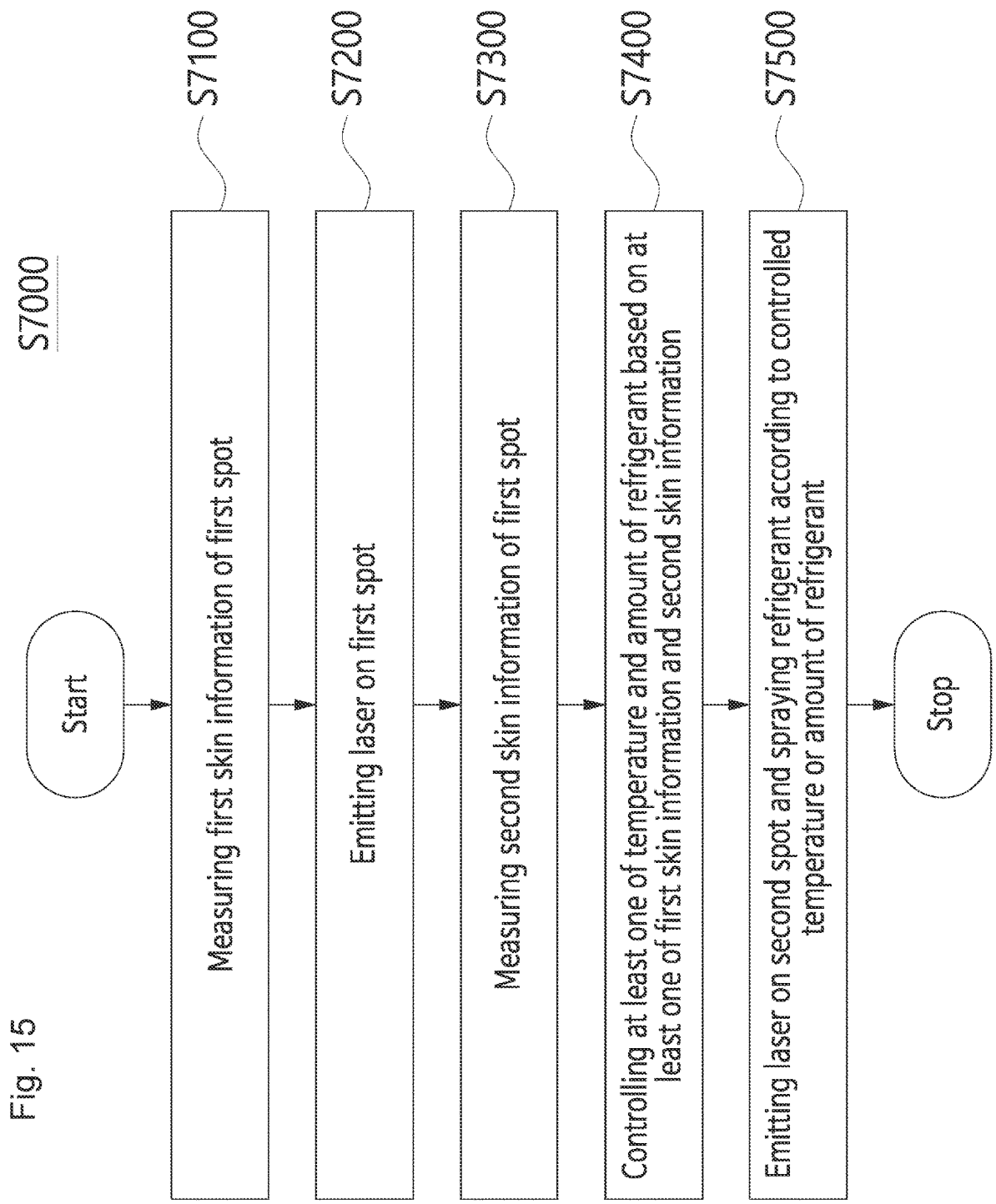
FIG. 15 is a flowchart illustrating the driving method of the laser treatment device when irradiating a plurality of spots with lasers.

The following will be described with reference to FIGS. 13 and 15. FIG. 13 is a view illustrating the irradiation of the first spot with a laser. FIG. 14 is a view illustrating the irradiation of the second spot with a laser after a predetermined period of time elapses after the irradiation of the first spot with a laser. FIG. 15 is a flowchart illustrating the driving method S7000 of the laser treatment device when irradiating a plurality of spots with a laser.

The driving method of the laser treatment device 100 disclosed in the present specification may include: measuring the first skin information of the first spot after laser treatment starts at S7100; irradiating the first spot with a laser at S7200; measuring the second skin information of the first spot at S7300; controlling at least one of the temperature and amount of the refrigerant based on at least one of the first skin information and the second skin information at S7400; and spraying a refrigerant according to the laser irradiation on the second spot and the controlled temperature or amount of the refrigerant at S7500.

According to the embodiment, in the measuring of the first skin information of the first spot at S7100, skin information of the skin surface of the first spot to receive a treatment by a laser or an area adjacent to the skin surface may be detected by the sensing unit 1300. The first spot may be a spot different from the second spot to be described later. However, the first spot and the second spot may preferably be tissues in a living body that perform the same or similar function in adjacent areas.

The first skin information may be detected when or before a laser output to 'the first spot' starts.

Additionally, the first skin information may be the skin temperature of the skin surface of 'the first spot' or an area adjacent to the skin surface. However, the first skin information is not limited thereto and may include a patient's a skin type, a treatment area, and a position of a target.

In the irradiation of the first spot with a laser at S7200, the laser module 1100 may output a laser to the first spot to receive a treatment. Preferably, the irradiation of the first spot with the laser may be intended to obtain skin information for suitably controlling the temperature and/or amount of a refrigerant to be sprayed when irradiating the second spot with a laser. In other words, skin information at the starting time and stopping time of the laser emission section of 'the first spot' may be obtained and may be intended to control the temperature and/or amount of a refrigerant, based on the skin information, such that the skin surface temperature does not reach the skin damage temperature during the laser treatment of the second spot which is a spot different from the first spot.

According to the embodiment, in the measuring of the second skin information of the first spot at S7300, the second skin information may be detected by the sensing unit 1300 in the same skin surface area as the skin surface area in which the first skin information is measured. That is, the second skin information may be measured in the first spot.

The second skin information may be detected when or after a laser output to 'the first spot' stops.

Additionally, the second skin information may be 'the skin surface temperature' of the skin surface of 'the first spot' or an area adjacent to the skin surface. However, the second skin information is not limited to the skin surface temperature and may include a laser type (laser wavelength and output) and a laser emission time, etc. in the laser emission section.

In the controlling of at least one of the temperature and amount of a refrigerant based on at least one of the first skin information and the second skin information at S7400, at least one of the temperature and amount of a refrigerant to be sprayed during the irradiation of the second spot with a laser may be controlled based on at least one of the first skin information and the second skin information detected from the first spot. In this case, when the second spot is irradiated with a laser by controlling at least one of the temperature and amount of the refrigerant to be sprayed during the laser irradiation on the second spot, the skin surface temperature of the second spot may be controlled not to reach the skin damage temperature. Through this, it is possible to minimize the possibility of skin damage of the second spot.

In the spraying of a refrigerant according to the laser irradiation on the second spot and the controlled temperature or amount of the refrigerant at S6500, a refrigerant may be sprayed on the second spot according to the controlled temperature and/or amount of the refrigerant based on at least one of the first skin information and the second skin information detected from the first spot. In this case, the refrigerant sprayed on the second spot may be sprayed before the second spot is irradiated with a laser. Alternatively, while the second spot is irradiated with a laser, a refrigerant may be sprayed on the second spot. Alternatively, after the second spot is irradiated with a laser, a refrigerant may be sprayed on the second spot.

The above-described embodiment may be applied when the treatment environments, treatment types, or treatment methods of the first spot and second spot are the same or similar.

However, even when the treatment environments, treatment types, or treatment methods of the first spot and second spot are different, at least one of the temperature and amount of the refrigerant to be sprayed on the second spot may be controlled based on at least one of the first skin information and the second skin information of the first spot in additional consideration of difference between the treatment environments, treatment types, or treatment methods of the first spot and second spot.

For example, although not shown in FIG. 15, when performing the laser treatment of the second shot after the laser treatment of the first shot, the third skin information of the second spot may be measured by the sensing unit 1300.

The third skin information may be skin information of the second spot at least when or before the laser output of the second shot starts. Additionally, the third skin information may be 'a skin temperature' of the skin surface of a target to receive a treatment by a laser of the second shot or an area adjacent to the skin surface. For example, the third skin information may be a skin surface temperature before thermal energy is applied to a skin surface corresponding to the second spot by outputting the laser of the second shot. However, the third skin information is not limited to the skin surface temperature and may also include a patient's a skin type, a treatment area, and the position and/or depth of a target, etc. For example, when treatment for hair removal is performed, information on the characteristics (e.g., moisture and sensitivity, etc.) of the skin on which hair is located and skin information on the position or depth of a target may be measured and used as a basis for controlling the characteristics of a refrigerant during the laser irradiation of the second shot.

In an embodiment, the control module 1400 may control at least one of the temperature and amount of a refrigerant to be sprayed during the laser treatment of the second shot based on at least one among the first skin information and second skin information related to the first shot and the third skin information related to the second shot obtained through the sensing unit 1300.

For example, the control module 1400 may control the temperature or amount of a refrigerant to be sprayed during the laser treatment of the second shot based on difference between the first skin information related to the first shot and the third skin information related to the second shot. For example, the control module 1400 may control the temperature of a refrigerant to be sprayed on the second spot to be relatively high when a skin temperature included the first skin information is higher than a skin temperature included in the third skin information than when the skin temperature included in the first skin information is lower than the skin temperature included in the third skin information. Alternatively, the control module 1400 may control the amount of a refrigerant to be sprayed on the second spot to be relatively small when the skin temperature included in the first skin information is higher than the skin temperature included in the third skin information than when the skin temperature included in the first skin information is lower than the skin temperature included in the third skin information.

For example, the control module 1400 may control the temperature or amount of a refrigerant to be sprayed during the laser treatment of the second shot based on 'difference' between the second skin information related to the first shot and the third skin information related to the second shot. For example, the control module 1400 may control the temperature of a refrigerant to be sprayed on the second spot to be relatively high in a case in which the difference between the skin temperature included in the second skin information and the skin temperature included in the third skin information is second difference larger than first difference than a case in which difference between a skin temperature included in the second skin information and a skin temperature included in the third skin information is the first difference. Alternatively, the control module 1400 may control the amount of a refrigerant to be sprayed on the second spot to be relatively small in a case in which difference between the skin temperature included in the second skin information and the skin temperature included in the third skin information is the second difference larger than the first difference than a case in which difference between the skin temperature included in the second skin information and the skin temperature included in the third skin information is the first difference.

Referring to FIGS. 10 to 12, as a method of outputting a plurality of laser shots to a spot, the laser treatment device 100 disclosed in the present specification may be operated. Additionally, referring to FIGS. 13 to 15, as a method of outputting a laser shot to each of a plurality of spots, the laser treatment device 100 disclosed in the present specification may be operated. However, this is not restrictive, and any principle and advantages of a method of outputting a plurality of laser shots to one spot and any principle and advantages of a method of outputting a laser shot to each of a plurality of spots may be combined with each other.

For example, when treatment is performed by irradiating the first spot with a first shot, the temperature and/or amount of a refrigerant to be sprayed during the treatment of the second shot on the first spot may be controlled based on at least one of the first skin information and the second skin information for the first shot. In addition, the temperature and/or amount of a refrigerant to be sprayed during laser treatment on the second spot may be controlled based on at least one of the first skin information and the second skin information for the first shot.

That is, the method of outputting a plurality of laser shots to one spot and the method of outputting a laser shot to each of a plurality of spots may be combined with each other.

Hereinafter, the method of emitting a laser during cooling by using the laser treatment device 100 having a cooling system according to the embodiment of the present specification will be described with reference to FIG. 16.

Figure 16:
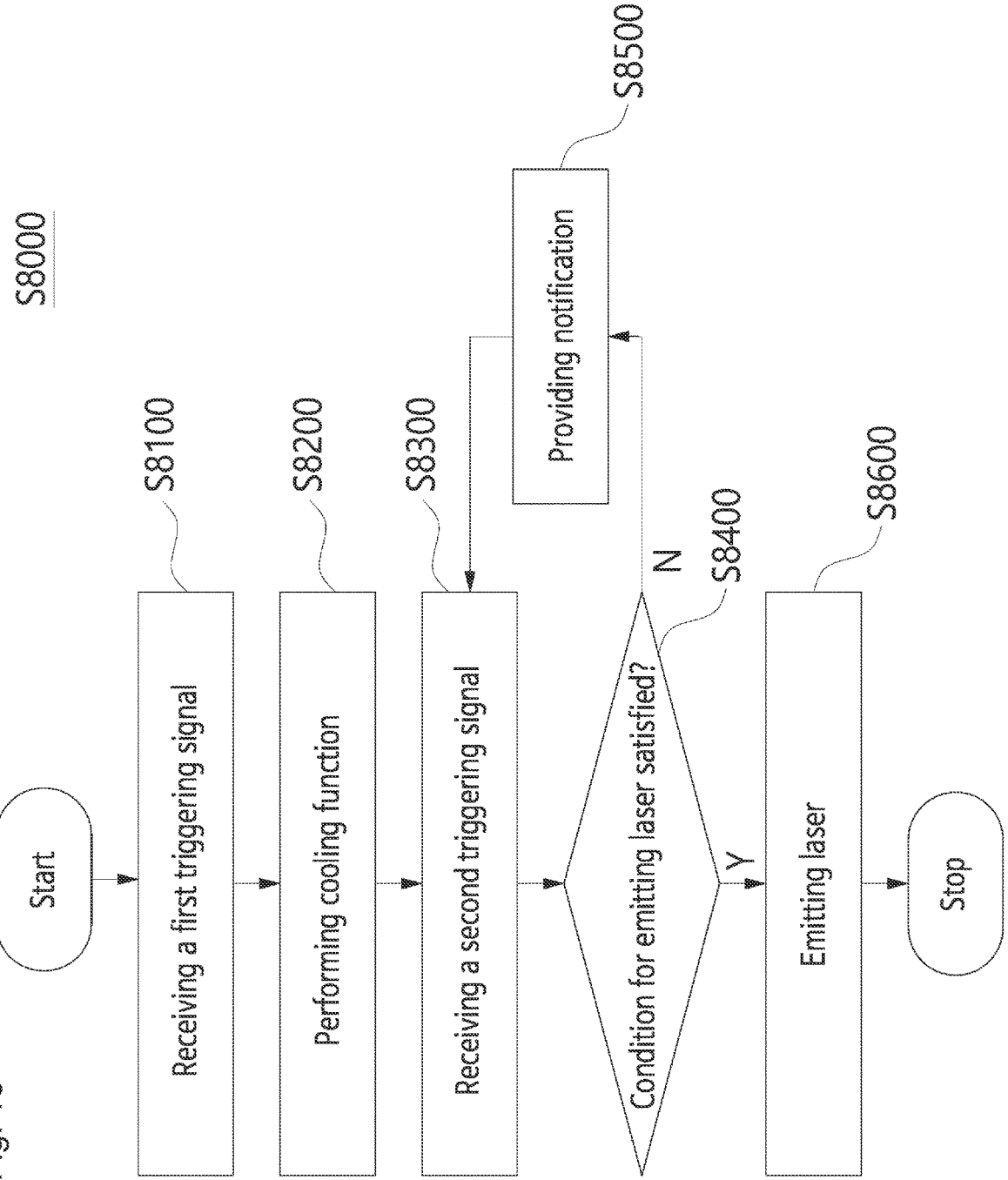
FIG. 16 is a flowchart illustrating the method of emitting a laser during cooling according to the embodiment of the present disclosure.

FIG. 16 is a flowchart illustrating the method S8000 of emitting a laser during cooling according to the embodiment of the present disclosure.

Referring to FIG. 16, in laser treatment, the method S8000 of emitting a laser during cooling on the skin surface may include: receiving a first triggering signal at S8100; performing a cooling function at S8200; receiving a second triggering signal at S8300; determining whether a laser emission condition is satisfied at S8400; providing a notification at S8500; and emitting a laser at S8600.

Hereinafter, each step will be described in more detail.

The laser treatment device 100 may receive the first triggering signal from a user at S8100. Here, the first triggering signal may include a triggering signal for commanding the start of the laser treatment and/or a triggering signal for commanding cooling before the laser treatment. In this case, the laser treatment device 100 may include a first triggering button (or a first trigger) for receiving the first triggering signal.

When receiving the first triggering signal, the laser treatment device 100 may operate the cooling module such that a skin surface is cooled at S8200. For example, the cooling module continuously may measure a skin surface temperature and may cool a skin surface by periodically or continuously spraying a refrigerant on the skin surface such that the skin surface temperature is a predetermined first set temperature Ts1. For another example, the cooling module may cool the skin surface such that the skin surface temperature is within a preset temperature range relative to the predetermined first set temperature Ts1. For still another example, the cooling module may cool the skin surface such that the skin surface temperature is changed over time in different set temperature ranges. In this case, the laser treatment device 100 may use skin temperature information obtained from the sensing unit when operating the cooling module.

The laser treatment device 100 may receive the second triggering signal from a user at S8300. The second triggering signal may include a signal for commanding a laser irradiation on the skin surface. In this case, the laser treatment device 10 may include a second triggering button (or a second trigger) for receiving the second triggering signal. Meanwhile, the receiving S8300 of the second triggering signal may be omitted or may be performed after the determining S8400 of whether the laser emission condition is satisfied, which will be described later. Through the receiving of the second triggering signal at S8300, a user may emit a laser on the skin surface at a desired time.

When receiving the first triggering signal or the second triggering signal, the laser treatment device 100 may determine whether the laser emission condition is satisfied at S8400. Here, the laser emission condition may include at least one of a condition under which a skin surface temperature is included in a set temperature range, a condition under which the skin surface temperature is maintained in the set temperature range for a predetermined period of time, and a condition under which a predetermined period of time elapses after a refrigerant begins to be sprayed on a skin surface. Of course, the data on the skin surface temperature described in the present specification may be used to determine whether the above-described conditions are satisfied.

When the laser emission condition is not satisfied, the laser treatment device 100 may provide a notification at S8500 and may perform the cooling function the skin surface at S8200. For example, the laser treatment device 100 may include the notification module and may provide a notification notifying that the laser emission condition is not satisfied to a user through the notification module. The notification may be performed in various ways, such as visual, audible, and tactile notifications. Meanwhile, even when the laser emission condition is satisfied, the laser treatment device 100 may provide to a user a notification notifying that the laser emission condition is satisfied.

When the laser emission condition is satisfied, the laser treatment device 100 may emit a laser on the skin surface at S8600. For example, the laser treatment device 100 may operate the laser module within a predetermined period of time from time at which the laser emission condition is satisfied and may emit a laser on the skin surface. Meanwhile, when the laser emission condition is satisfied, the laser treatment device 100 may provide a notification to a user and may emit a laser on the skin surface when receiving the second triggering signal from the user.

When cooling on the skin surface is performed, the method of emitting a laser at S8000 may omit at least one of the above-described steps. For example, the determining of whether the laser emission condition is satisfied at S8400 and the providing of a notification at S8500 may be omitted. Specifically, the laser treatment device 100 may emit a laser when receiving the second triggering signal while cooling the skin surface. Alternatively, the laser treatment device 100 may cool the skin surface when receiving the first triggering signal and may emit a laser when a predetermined period of time elapses or the skin surface satisfies a specific temperature condition.

Furthermore, although not shown in FIG. 16, as described in other parts of the present specification, even while the skin surface is irradiated with a laser, the skin surface may be cooled, and even after the laser irradiation, the skin surface may be cooled. For example, the laser treatment device 100 may control a sprayed refrigerant such that the skin surface temperature is the second set temperature Ts2 while the skin is irradiated with a laser, and may control a sprayed refrigerant such that the skin surface temperature is the third set temperature after the laser irradiation. For another example, the laser treatment device 100 may stop spraying a refrigerant when laser irradiation starts. For still another example, the laser treatment device 100 may stop spraying a refrigerant when laser irradiation starts, and may restart the spraying of a refrigerant when the laser irradiation stops and may control a refrigerant such that the skin surface temperature is the same as the first set temperature Ts1 or is another third set temperature.

As described above, when a predetermined condition is satisfied while a skin surface is cooled continuously or periodically, the skin surface is irradiated with a laser, and thus laser treatment which is safer and reduces pain due to the laser irradiation can be performed.

Meanwhile, in order to further improve the effect of the method S8000 of emitting a laser during cooling, a plurality of cooling modules may be used. For example, the laser treatment device 100 may include a main cooling module which continuously sprays a refrigerant in a spraying section and an auxiliary cooling module which sprays a refrigerant in a preset section set based on the laser emission time. Here, after the auxiliary cooling module is operated to spray a refrigerant on a skin surface, the laser module is operated to emit a laser.

Here, each of the main cooling module and the auxiliary cooling module may be understood to be similar to the cooling module described in the present specification, and may be configured to have some components common therewith. In addition, the main cooling module and the auxiliary cooling module may control a refrigerant sprayed on a skin surface by using different set temperatures.

In addition, here, the main cooling module and the auxiliary cooling module may operate based on the triggering signal described above. For example, the laser treatment device 100 may operate the main cooling module when receiving the first triggering signal and may operate the auxiliary cooling module when receiving the second triggering signal.

Accordingly, the laser treatment device 100 may include the main cooling module which continuously performs cooling in the spraying section and the auxiliary cooling module which temporarily performs cooling in the spraying section, and thus the laser treatment device 100 may continuously emit a laser while moving above the skin, so the skin surface can be cooled more quickly.

Hereinafter, the method of preventing the formation of an interfering substance 20 which interferes with a laser irradiation on the skin will be described with reference to FIGS. 17 to 22.

As described above, in laser treatment, cooling is performed before laser irradiation on the skin, and thus the interfering substance 20 (or a blocking substance and a reflective substance) which interferes with the laser irradiation or blocks at least a portion of the laser may occur. For example, as a skin surface temperature is decreased by cooling, frost is generated on a skin surface and scatters or reflects a laser with which the skin surface is irradiated and thus may block at least a portion of the laser. For another example, as the temperature of a refrigerant sprayed on the skin surface decreases, at least a portion of the refrigerant is frozen in the laser emission path and thus may scatter or reflect an emitted laser. Accordingly, to prevent the formation of this interfering substance 20 or to remove a generated interfering substance 20, it is necessary to promote more effective laser treatment by controlling the skin surface or the temperature of a refrigerant.

Figure 17:
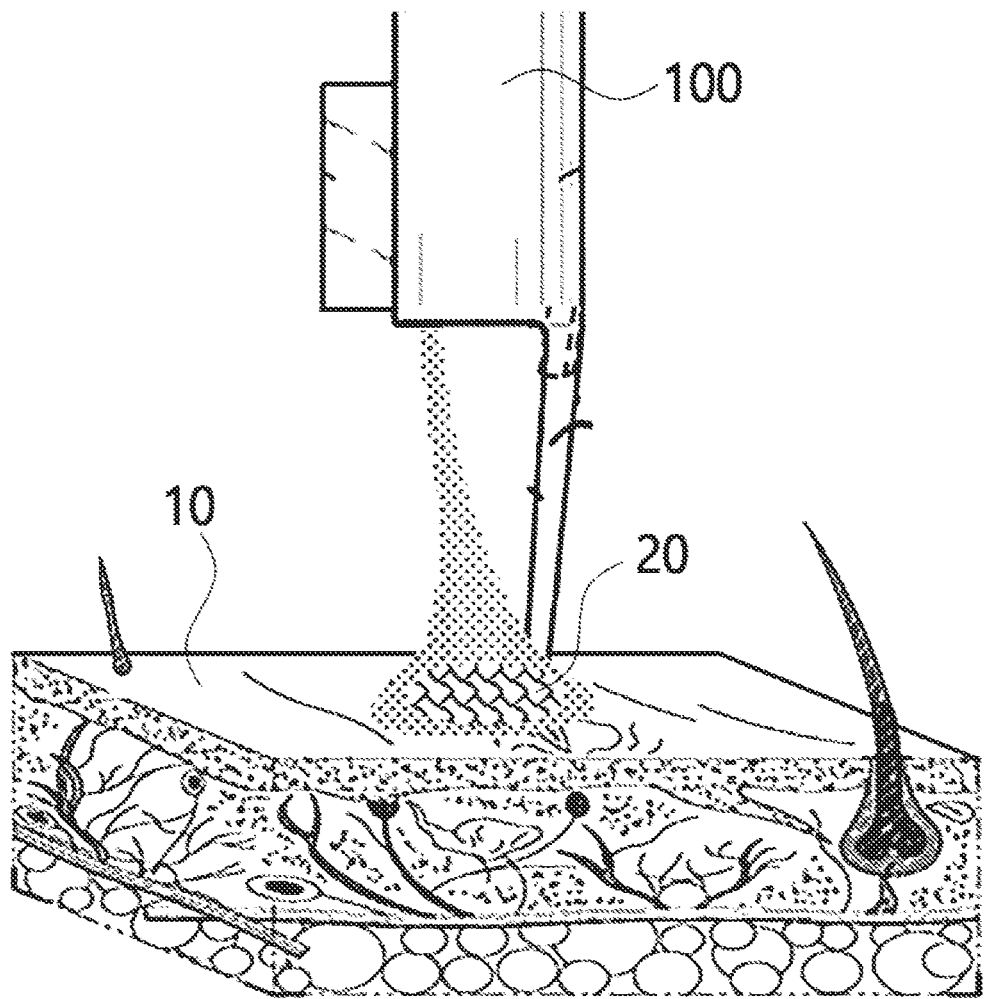
FIG. 17 is a view illustrating a state in which an interfering substance is formed on the surface of the skin when the skin is cooled according to the embodiment of the present specification.

FIG. 17 is a view illustrating a state in which the interfering substance 20 is generated on a skin surface when the skin is cooled according to the embodiment of the present specification.

Figure 18:
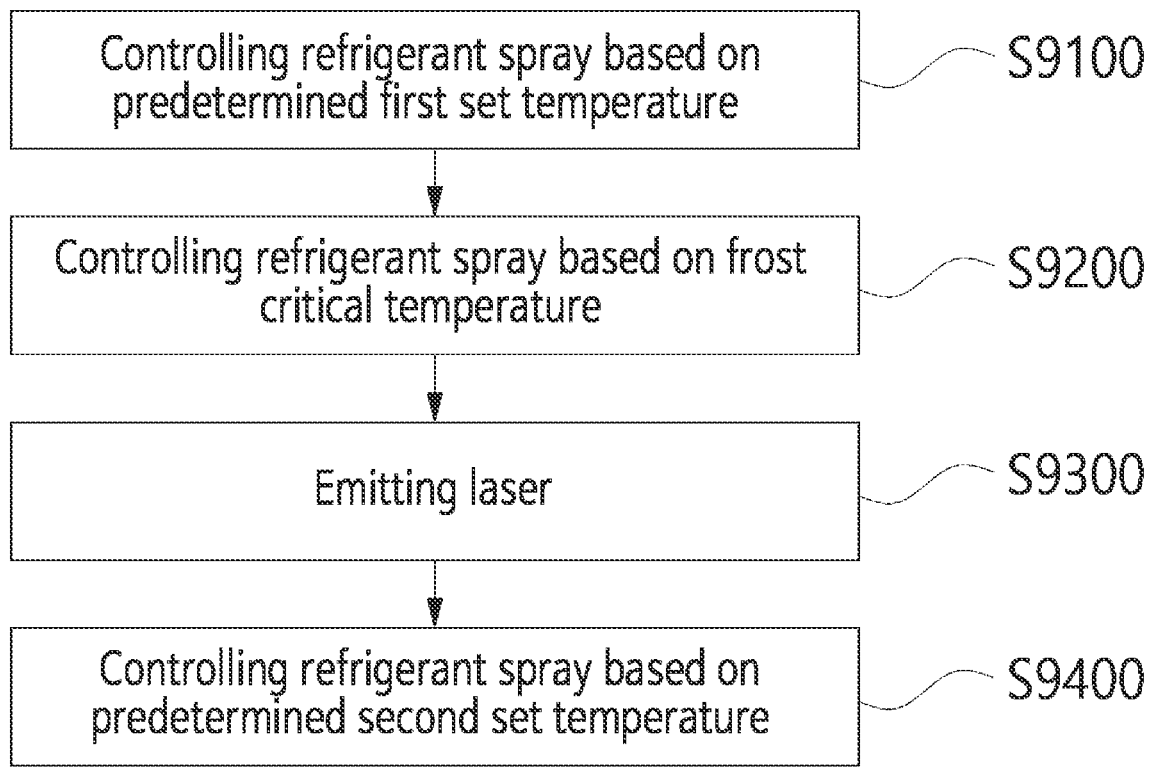
FIG. 18 is a view illustrating a method of preventing the formation of an interfering substance during the cooling according to the embodiment of the present specification.

FIG. 18 is a view illustrating the method of preventing the formation of the interfering substance 20 when cooling is performed according to the embodiment of the present specification.

Figure 19:
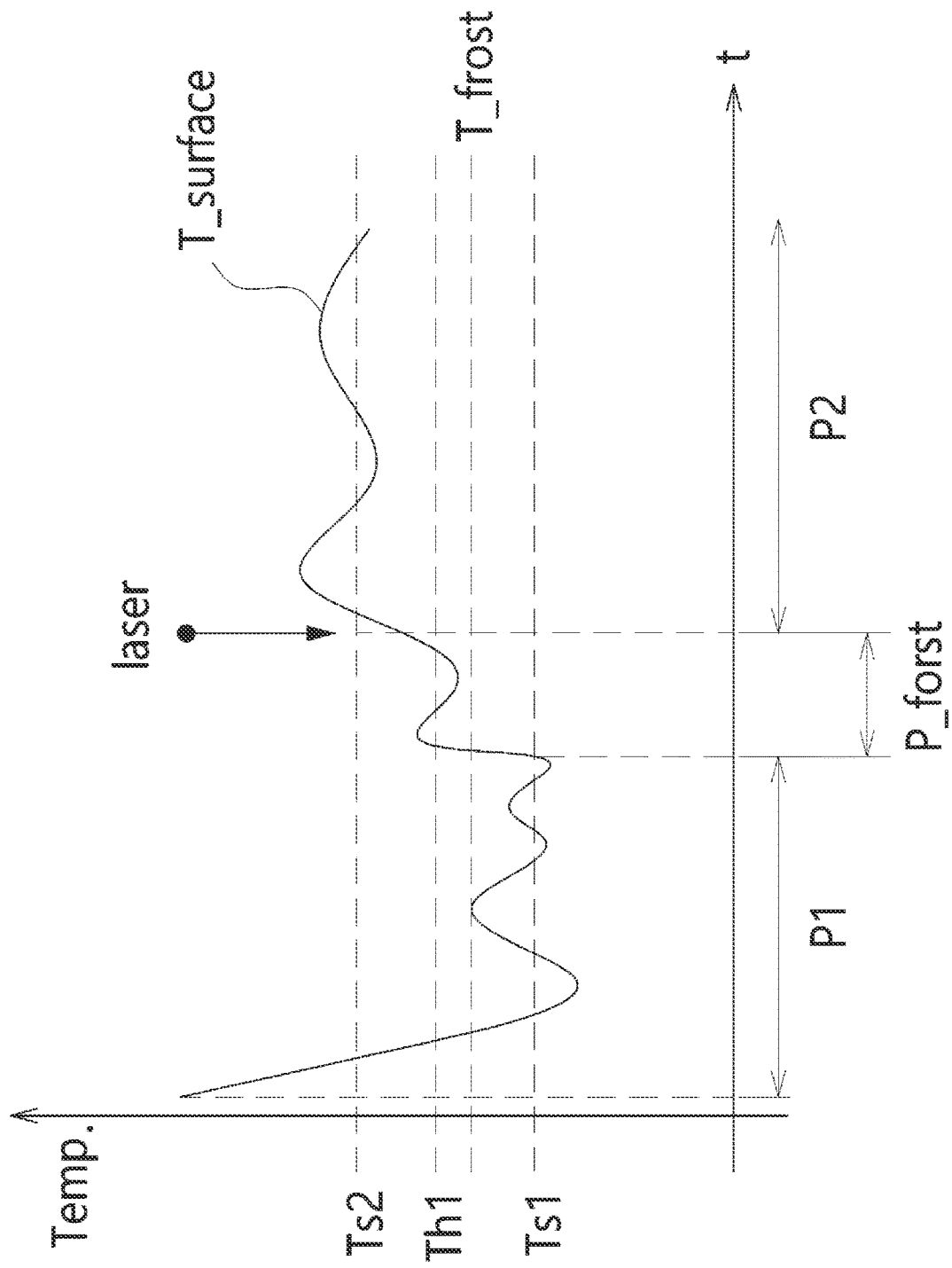
FIG. 19 is a view illustrating a method of performing the cooling of the skin surface in a spraying section including a frost prevention section according to the embodiment of the present specification.

FIG. 19 is a view illustrating a method of performing the cooling of the skin surface in a spraying section including a frost prevention section P frost according to the embodiment of the present specification.

Referring to FIG. 17, the interfering substance 20 may be formed on the skin surface. For example, moisture in the air or moisture or gaseous substances contained in the skin may condense as the skin is cooled, and accordingly, the interfering substance 20 may be formed. For another example, when a refrigerant sprayed for cooling a skin surface is condensed, the interfering substance 20 may be formed on the skin surface. This interfering substance 20 obstructs a user's view, or reflects or scatters a laser with which the skin 10 is irradiated in the laser treatment of the skin 10, and as a result, the effect of the laser treatment may decrease. Hereinafter, for convenience of explanation, a case in which the interfering substance 20 is frost is mainly described, but the technical idea of the present specification is not limited thereto, and any substance which is formed on the skin surface by cooling and interferes with a user's view and scatters or reflects a laser may be similarly applied.

Referring to FIG. 18, the method S9000 of preventing the formation of frost may include: controlling the spraying of a refrigerant based on a first set temperature at S9100; controlling the spraying of a refrigerant based on a frost critical temperature at S9200; emitting a laser at S9300; and controlling the spraying of a refrigerant based on a second set temperature at S9400.

Hereinafter, each step will be described in detail.

The laser treatment device 100 may control the spraying of a refrigerant based on the first set temperature at S9100. For example, the laser treatment device 100 may decrease a skin surface temperature by spraying a refrigerant in the pre-cooling section P1 before irradiating a target on which laser treatment is intended to be performed with a laser. Here, a temperature preset in the laser treatment device 100 for performing cooling may include the first set temperature Ts1 described in other parts of the present specification. In this case, the predetermined first set temperature Ts1 may be lower than or the same as the frost critical temperature Th1 to be described later.

The laser treatment device 100 may control the spraying of a refrigerant based on the frost critical temperature at S9200). For example, the laser treatment device 100 may control the spraying of a refrigerant based on the frost critical temperature Th1 before irradiating a target or a skin surface with a laser. Here, as described later, the frost critical temperature Th1 may mean a temperature at which frost is not formed. Accordingly, it is possible to prevent the formation of frost before a target or a skin surface is irradiated with a laser.

The laser treatment device 100 may emit a laser on a target or a skin surface at S9300. For example, the laser treatment device 100 may cool a skin surface by controlling a refrigerant based on the frost critical temperature Th1 and then may emit a laser to the skin surface. For another example, the laser treatment device 100 may emit a laser on a target or a skin surface by receiving a user's input. Here, the laser treatment device 100 may determine whether frost is formed on the skin surface before outputting the laser. Specifically, the laser treatment device 100 may determine whether frost is formed by measuring a skin surface temperature.

Alternatively, the laser treatment device 100 may determine that frost is not formed when a period of time, for which a refrigerant is controlled based on the frost critical temperature Th1, is a predetermined period of time or more. Alternatively, the laser treatment device 100 may determine whether frost is formed by receiving a user's input. The determining of whether frost is formed is not necessarily performed.

The laser treatment device 100 may control the spraying of a refrigerant based on the second set temperature Ts2 at S9400. For example, the laser treatment device 100 may decrease a skin surface temperature increased by a laser by spraying a refrigerant thereto in the inter-cooling section P2 in which a target or a skin surface is irradiated with the laser. Here, a temperature set in the laser treatment device 100 for performing cooling may include the second set temperature Ts2 described in other parts of the present specification. In this case, the second set temperature Ts2 may be higher than or the same as the frost critical temperature Th1.

Meanwhile, the controlling of the spraying of a refrigerant based on the second set temperature Ts2 at S9400 may be omitted. For example, the laser treatment device 100 may prohibit the spraying of a refrigerant in the inter-cooling section P2. For another example, the laser treatment device 100 may prohibit the spraying of a refrigerant in the inter-cooling section P2 and may spray a refrigerant on the skin after laser irradiation stops.

Although not shown, the laser treatment device 100 may control the spraying of a refrigerant even in the post-cooling section P3 after the laser irradiation. For example, the laser treatment device 100 may perform cooling a target or a skin surface based on the third set temperature Ts3 after laser irradiation on the target or skin surface and may remove a portion of heat remaining on the target or skin surface according to the laser irradiation. Here, the third set temperature Ts3 set in the post-cooling section P3 may be set regardless of the frost critical temperature Th1. Alternatively, the third set temperature Ts3 may be set lower than the second set temperature Ts2 and higher than the frost critical temperature Th1 or may be set lower than the frost critical temperature Th1.

Referring to FIG. 19, to prevent the formation of frost or to remove frost before laser irradiation, the laser treatment device 100 may perform cooling a skin surface to the frost critical temperature Th1 and accordingly, skin surface temperature may be controlled.

For example, the laser treatment device 100 may perform cooling based on the frost critical temperature Th1 in a frost prevention section P frost before the laser irradiation.

Here, the frost prevention section P frost is disposed between the pre-cooling section P1 and the inter-cooling section P2 or may be included in the pre-cooling section P1 by being disposed before the inter-cooling section P2. Alternatively, the frost prevention section P frost may include at least a portion of the pre-cooling section P1 and at least a portion of the inter-cooling section P2.

Additionally, here, the frost prevention section P frost may be preset short enough to increase cooling efficiency or preset long enough to increase frost prevention efficiency. For example, the length of the frost prevention section P frost length may be selected in the range of 0 to 10 seconds. Alternatively, the length of the frost prevention section P frost may be preset within 0 to 20% of the pre-cooling section P1. Meanwhile, the length of the frost prevention section P frost may be set in consideration of the temperature or amount of a sprayed refrigerant. Additionally, here, the frost critical temperature Th1 may include a temperature at which the interfering substance 20 such as frost or ice is not formed. For example, the frost critical temperature Th1 may be set as a frost formation temperature T frost or more at which frost is formed. Specifically, the frost critical temperature Th1 can be set above 0° C. For another example, the frost critical temperature Th1 may be set in consideration of the skin 10 or humidity around the skin. Specifically, the frost critical temperature Th1 may be set higher when humidity around the skin is relatively high than when humidity around the skin is relatively low. Meanwhile, the frost critical temperature Th1 may be set higher than the first set temperature Ts1, which is based on cooling at the starting time of the cooling on a skin surface.

Figure 20:
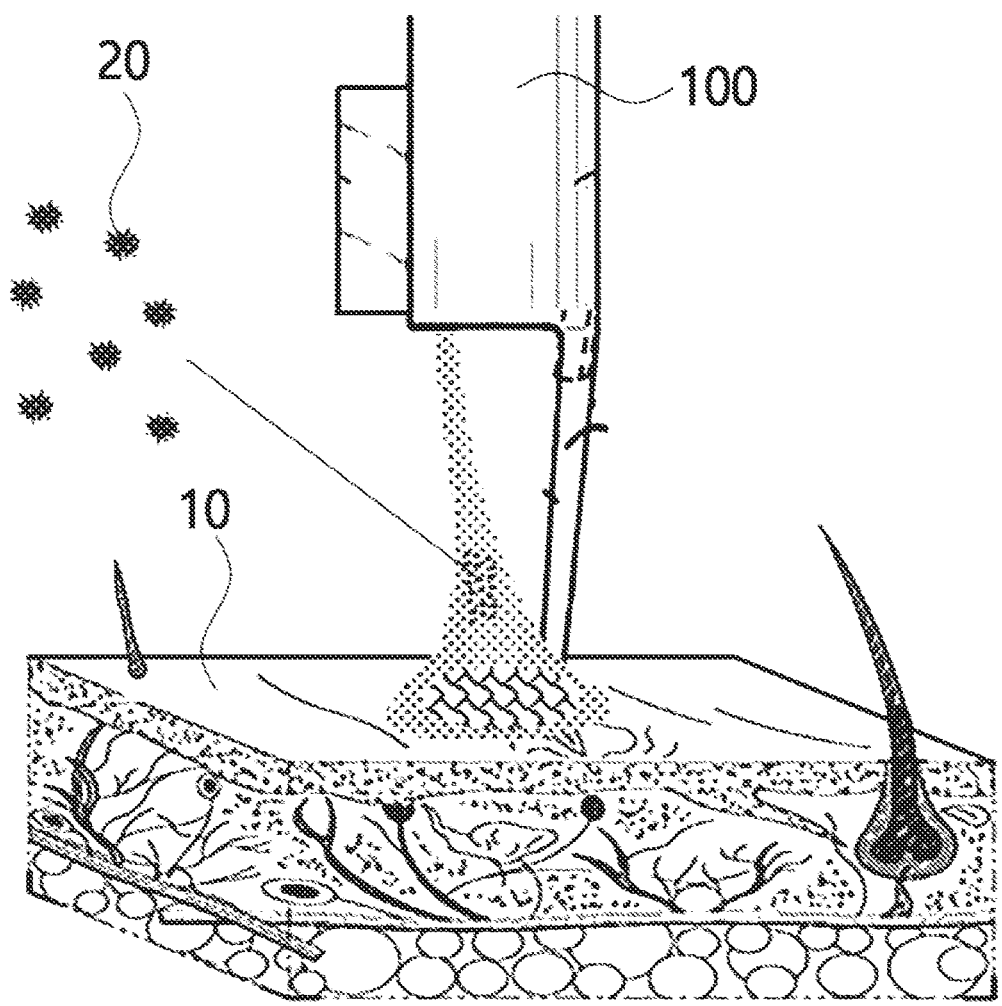
FIG. 20 is a view illustrating a state in which interfering substances are formed in the path of a laser with which the skin is irradiated on according to the embodiment of the present specification.

FIG. 20 is a view illustrating a state in which the interfering substance 20 is generated in the path of a laser with which the skin 10 is irradiated according to the embodiment of the present specification.

FIG. 21 is a view illustrating a method of preventing the formation of interfering substance 20 in the path of a laser during cooling according to the embodiment of the present specification.

Figure 22:
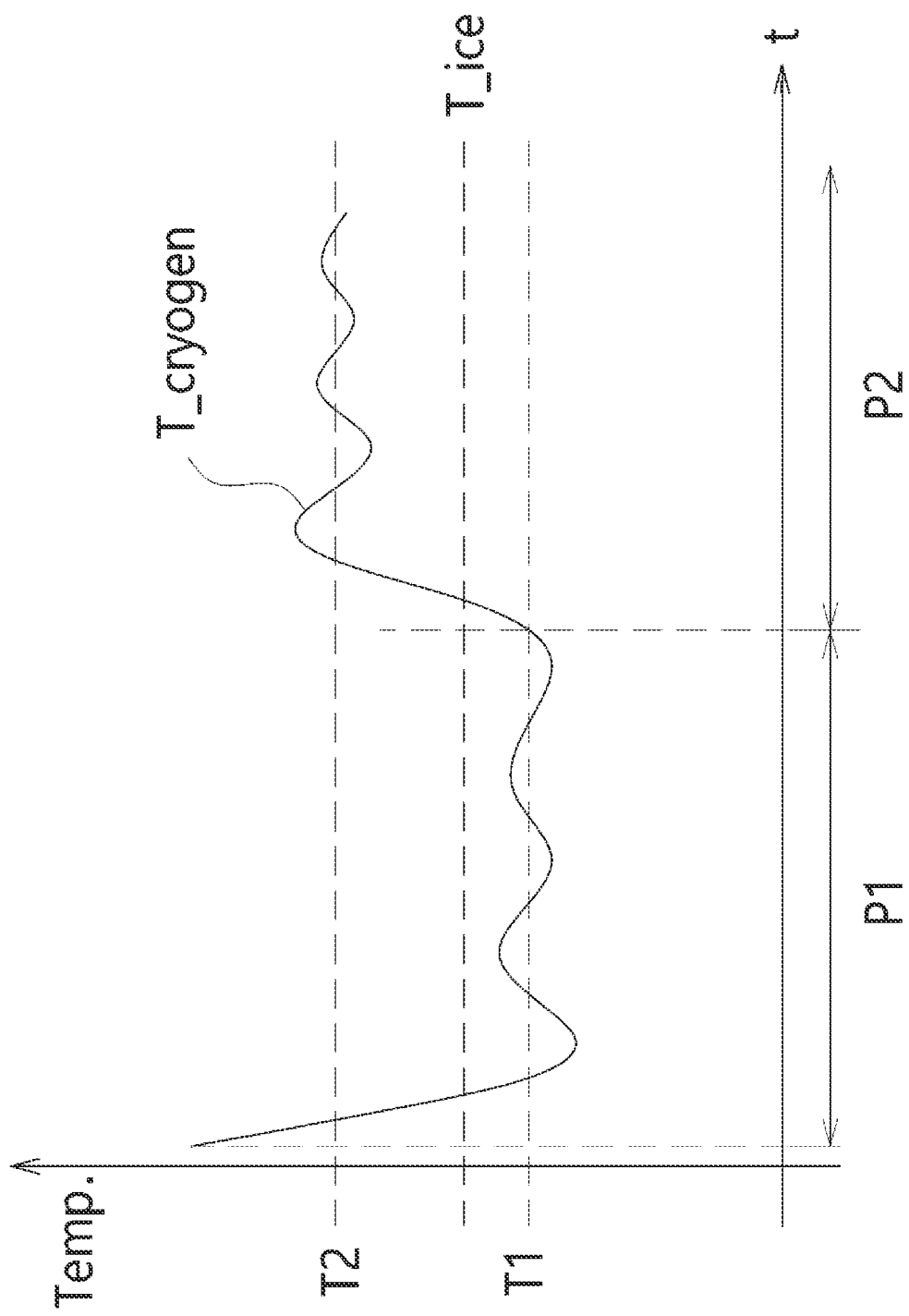
FIG. 22 is a view illustrating a method of controlling the temperature of a refrigerant for preventing the formation of interfering substances according to the embodiment of the present specification.

FIG. 22 is a view illustrating a method of controlling the temperature of a refrigerant for preventing the formation of an interfering substance 20 according to the embodiment of the present specification.

Referring to FIG. 20, the interfering substance 20 may be formed in the path of a laser with which the skin 10 is irradiated. For example, the interfering substance 20 may be formed in the spraying path of a refrigerant, and the interfering substance 20 may be formed in a part in which the spraying path of a refrigerant overlaps the laser emission path. Here, the interfering substance 20 may be formed when the temperature of a refrigerant decrease to a specific temperature or less, or pressure of a refrigerant increases. Specifically, the interfering substance 20 may be formed when at least a portion of a gas or liquid refrigerant changes to a solid state due to adiabatic expansion while the gas or liquid refrigerant is sprayed on the skin 10.

Accordingly, the interfering substance 20 formed in the laser emission path may scatter or reflect at least a portion of a laser and thus sufficient thermal energy may not be applied to a target area, and accordingly, the efficiency of the laser treatment may decrease.

Hereinafter, for convenience of explanation, a case in which the interfering substance 20 formed in the laser emission path is dry ice is mainly described, but the technical idea of the present specification is not limited thereto, and any substance that is formed in the laser emission path by cooling and scatters or reflects a laser may be similarly applied.

Referring to FIG. 21, the method S10000 of preventing the formation of dry ice may include: setting a first temperature T1 and a second temperature T2 based on a dry ice formation temperature T_ice at S10100; controlling a refrigerant temperature based on the first temperature T1 at S10200; emitting a laser S10300; and controlling the refrigerant temperature based on the second temperature T2 at S10400.

Here, the refrigerant temperature may mean a temperature of a refrigerant before the refrigerant is sprayed from the laser treatment device or a temperature of a refrigerant sprayed from the laser treatment device 100. In addition, the refrigerant temperature may be measured by the sensing unit included in the laser treatment device or may be measured by a separate sensing unit.

Hereinafter, each step will be described in detail.

The laser treatment device 100 may preset the first temperature T1 and the second temperature T2 based on the dry ice formation temperature at S10100. For example, the control module of the laser treatment device 100 may set the first temperature T1 and the second temperature T2 as a temperature at which the refrigerant temperature is controlled during the cooling of a skin surface. For another example, the first temperature T1 and the second temperature T2 as refrigerant temperature information used to perform the cooling are stored in the memory of the laser treatment device 100, and the control module may control the refrigerant temperature during the cooling by using the first temperature T1 and second temperature T2. For another example, the first temperature T1 and the second temperature T2 may be set based on a user's input. Here, the first temperature T1 and the second temperature T2 may be set based on the dry ice formation temperature to be described later. Specifically, the first temperature T1 may be set lower than the dry ice formation temperature and the second temperature T2 may be set higher than the dry ice formation temperature. This step may be performed or omitted before or during the cooling of the skin surface is performed.

The laser treatment device 100 may control the refrigerant temperature based on the first temperature T1 at S10200. For example, the laser treatment device 100 may supply thermal energy to a refrigerant based on the first temperature T1 before laser irradiation. Specifically, the laser treatment device 100 may measure the refrigerant temperature during cooling, and may control at least one of the flow rate control unit and the refrigerant condition control unit such that the refrigerant temperature is controlled close to the first temperature T1. For another example, the laser treatment device 100 may cool a skin surface by using the predetermined first set temperature preset in consideration of the first temperature T1.

The laser treatment device 100 may emit a laser on a target or a skin surface at S10300. For example, the laser treatment device 100 may spray a refrigerant, which is controlled based on the first temperature T1, on the skin surface so as to cool the skin surface and may emit a laser on the skin surface when a predetermined time elapses. For another example, the laser treatment device 100 may emit laser on a target or a skin surface by receiving a user's input. For another example, the laser treatment device 100 may emit a laser when the skin surface temperature or the refrigerant temperature is a set temperature or higher. Here, the laser treatment device 100 may determine whether dry ice is formed in the laser emission path before outputting the laser. Specifically, the laser treatment device 100 may determine whether dry ice is formed by measuring the temperature of a refrigerant. Alternatively, the laser treatment device 100 may determine whether dry ice is formed by receiving a user's input. The determining of whether dry ice is formed is not necessarily performed.

The laser treatment device 100 may control the refrigerant temperature based on the second temperature T2 at S10400). For example, when irradiating the skin with a laser, the laser treatment device 100 may cool a skin surface by spraying a refrigerant whose temperature is controlled on the skin surface based on the second temperature T2. For another example, while irradiating the skin with a laser, the laser treatment device 100 may cool a skin surface to the second set temperature Ts2 corresponding to the second temperature T2.

Although not shown, the laser treatment device 100 may control a refrigerant temperature even in the post-cooling section P3 after the laser irradiation. For example, the laser treatment device 100 may control a refrigerant based on a third temperature T3 after irradiating a target or skin with a laser, or may perform cooling based on the third set temperature Ts3 corresponding to the third temperature T3 and may remove at least a portion of heat remaining on the skin surface or target according to the laser irradiation. Here, the third temperature T3 set in the post-cooling section P3 may be preset regardless of the dry ice formation temperature. Alternatively, the third temperature T3 may be set lower than the second temperature T2 and higher than the dry ice formation temperature, or may be set lower than the dry ice formation temperature.

Referring to FIG. 22, the temperature of a refrigerant may be controlled to different temperatures in the pre-cooling section P1 and the inter-cooling section P2, and accordingly, the refrigerant temperature can be controlled.

The temperature of a refrigerant in the pre-cooling section P1 may be controlled to the first temperature T1. For example, the laser treatment device may sense the temperature of a refrigerant in the pre-cooling section P1 and may control the refrigerant condition control unit or the flow rate control unit such that the temperature of the refrigerant is within a range preset from the first temperature T1.

The temperature of a refrigerant in the inter-cooling section P2 may be controlled to the second temperature T2. For example, the laser treatment device may sense the temperature of a refrigerant in the inter-cooling section P2 and may control the refrigerant condition control unit or the flow rate control unit such that the temperature of the refrigerant is within a range preset from the second temperature T2.

The first temperature T1 and the second temperature T2 may be set relative to the dry ice formation temperature T_ice. For example, the first temperature T1 may be lower than the dry ice formation temperature. For another example, the second temperature T2 may be higher than the dry ice formation temperature.

The dry ice formation temperature may mean a temperature at which at least a portion of a refrigerant or a sprayed refrigerant forms dry ice. The dry ice formation temperature may be set in consideration of pressure of a refrigerant before the spraying of the refrigerant and pressure (e.g., atmospheric pressure) of the refrigerant after the spraying of the refrigerant. Specifically, the dry ice formation temperature may be set based on a degree to which the temperature of a refrigerant changes through adiabatic expansion when the refrigerant is sprayed. For example, the dry ice formation temperature may be set to −20° C. to 10° C.

Meanwhile, the dry ice formation temperature may be set based on the phase ratio of a sprayed refrigerant. For example, when a refrigerant is sprayed, the refrigerant may include a first part which has a gaseous state, and a second part which includes at least one of a liquid droplet and a solid particle, and according to the temperature of a refrigerant, a ratio of the first part to the second part may be determined. Specifically, a sprayed refrigerant may include the first part which has at least a gaseous state, and the second part which includes dry ice, and according to the temperature of a refrigerant, the ratio of dry ice in a sprayed refrigerant may be determined. For another example, a sprayed refrigerant may have the ratios of solid, liquid, and gaseous states into which the refrigerant changes according to a temperature thereof. In this case, the dry ice formation temperature may be a temperature at which the dry ice ratio of a sprayed refrigerant or liquid and solid state ratios thereof are a preset value or less. Alternatively, the dry ice formation temperature may be a temperature at which the ratio of the gaseous state of a sprayed refrigerant is a preset value or more. For example, the dry ice formation temperature may be preset such that the ratio of dry ice in a sprayed refrigerant is 10% or less. For another example, the dry ice formation temperature may include a temperature at which the ratio of the gaseous state of a sprayed refrigerant is 90% or more.

In the above, it has been mainly described that the temperature of a refrigerant is sensed and is controlled to be included in a specific temperature range, but the technical idea of the present specification is not limited thereto, and an interfering substance 20 may not be formed in the laser emission path by controlling the first and second set temperatures Ts1 and Ts2. For example, the laser treatment device may cool a skin surface based on the first set temperature Ts1 and the second set temperature Ts2 corresponding to the first temperature T1 and the second temperature T2, respectively, described above. For still another example, the laser treatment device may cool a skin surface to the first set temperature Ts1 lower than the dry ice formation temperature in the pre-cooling section P1, and may cool a skin surface to the second set temperature Ts2 higher than the dry ice formation temperature T_ice in the inter-cooling section P2.

Additionally, in the above, it has been mainly described that the interfering substance 20 is formed in the laser emission path according to the phase change of at least a portion of a refrigerant, but the technical idea of the present specification is not limited thereto, an interfering substance 20 formed from a refrigerant may be formed on the skin surface.

Meanwhile, the method S9000 of preventing the formation of frost and the method S10000 of preventing the formation of dry ice, which are described above, may be performed doubly. For example, while cooling is performed to prevent the formation of frost on the skin surface, a refrigerant temperature may be controlled to prevent the formation of dry ice in the laser emission path. Specifically, the laser treatment device 100 may cool a skin surface based on the first set temperature Ts1 and the second set temperature Ts2 preset in consideration of the frost critical temperature Th1 and the dry ice formation temperature in the pre-cooling section P1 and the inter-cooling section P2. Alternatively, the laser treatment device 100 may cool a skin surface based on the first set temperature Ts1 set in consideration of the frost critical temperature Th1 and the first temperature T1 in the pre-cooling section P1 and may cool the skin surface based on the second set temperature Ts2 set in consideration of the frost critical temperature Th1 and the second temperature T2 in the inter-cooling section P2.

When performing a treatment or treatment for a vascular lesion (a blood vessel lesion) by using a laser, a blood vessel is a target tissue of laser treatment and a medium which absorbs laser light. In other words, a target whose vascular lesion receives a treatment is a blood vessel. Accordingly, when performing a treatment for the vascular lesion by using a laser, it is required to prevent a blood vessel, which is a treatment target, from shrinking and being invisible. In addition, when the blood vessel is shrunk, it may be difficult for a practitioner to find a treatment target, and accordingly, the effect of treatment and/or treatment may be decreased, and a portion other than the blood vessel which is a treatment target may be irradiated with a laser, so side effects may occur. Accordingly, when performing treatment or treatment of a vascular lesion (a blood vessel lesion) by using a laser, it is necessary to prevent constriction of the blood vessel.

Additionally, in the case of a laser treatment and/or a laser treatment, thermal energy is accumulated in the skin by a high-power laser, so the possibility of skin damage exists. Accordingly, 'before' laser irradiation, the pre-cooling that lowers the temperature of the skin including a skin surface as much as possible may be performed. However, when performing the pre-cooling for a treatment and/or treatment of the vascular lesion, a skin temperature is decreased to a skin temperature at which the blood vessel is constricted, and due to the constriction of the blood vessel, side effects may occur as described above. Accordingly, the laser treatment device 100 which can perform a precise and accurate control such that a skin temperature can be controlled to at temperature at which the blood vessel does not constrict even if the pre-cooling is performed on the vascular lesion, and the treatment method of the laser treatment device are required.

Generally, when a temperature of the skin is in the range of about 2° C. to 18° C., the blood vessel may constrict. In addition, when the temperature of the skin is about 2° C. or less, the flow amount of blood is increased to prevent tissue damage, and the blood vessel may be relaxed. In addition, when the temperature of the skin is about 18° C. or higher, the blood vessel may be relaxed.

According to the driving method of the laser treatment device 100 disclosed in the present specification, by controlling a temperature of the skin to a temperature (e.g., the temperature of 18° C. or higher or 2° C. or less) at which the blood vessel does not constrict, the blood vessel may not constrict, and skin damage due to temperature rise of the skin during laser irradiation may be prevented.

Hereinafter, the laser treatment device 100 having a cooling system disclosed in the present specification and a vascular lesion treatment will be described. Any suitable principle and advantages of the components of the laser treatment device 100 described in relation to FIGS. 1 to 4 and any suitable principle and advantages of the driving method of the laser treatment device 100 according to the embodiments may be inferred and applied. Accordingly, hereinafter, in the treatment and/or treatment of the vascular lesion, the characteristics of the components of the laser treatment device 100 or the characteristics of the treatment method of a vascular lesion will be mainly described.

The laser treatment device 100 having a cooling system disclosed in the present specification may include: the laser module 1100 which outputs a laser on a patient's skin; the sensing unit 1300 which measures the temperature of the skin before, during, or after the skin is heated by the laser; the spraying unit 1230 which sprays a refrigerant on the skin; the refrigerant condition control unit 1220 which controls thermal energy applied to the refrigerant by using the thermoelectric element; and the control module 1400.

According to the laser treatment device 100 having a cooling system disclosed in the present specification, the laser treatment device 100 may be used to perform the treatment or treatment of a vascular lesion.

The laser module 1100 may generate and emit a laser having a wavelength of the wavelength band absorbed by the blood vessel which is a treatment target. For example, the blood vessel has high absorption for light having a wavelength in the range of 500 nm to 600 nm and in the range of 700 nm to 1200 nm. Additionally, oxyhemoglobin which moves in the blood vessel may have high absorption for light having a wavelength within the range of 350 nm to 500 nm. Accordingly, the laser module 1100 may emit a laser light having the above-described wavelength band. In addition, the laser light emitted by the laser module 1100 may be selected in consideration of a wavelength that can penetrate to a specific depth in consideration of not only absorption degree for a wavelength but also the position of the blood vessel (e.g., depth in the skin).

The sensing unit 1300 may measure the temperature of 'skin' including the skin surface. The sensing unit 1300 may preferably measure a skin surface temperature. The sensing unit 1300 measures the skin surface temperature and transmits the skin surface temperature to the control module 1400, and thus the control module 1400 may measure and provide information indicating whether the blood vessel is constricted or relaxed. The sensing unit 1300 may preferably be configured as a temperature sensing unit. However, the skin surface temperature is only an example, and the sensing unit 1300 may be configured to measure various types of information indicating that the blood vessel is constricted. For example, the various types of information may mean various types of information by which whether the blood vessel is constricted or relaxed can be determined, such as the flow amount of blood according to the constriction and relaxation of the blood vessel, a blood oxygen level, and blood pressure, etc.

The refrigerant condition control unit 1220 may control the temperature and/or amount of a refrigerant such that the skin surface temperature is controlled to a temperature corresponding to a temperature condition in which the blood vessel does not constrict.

Specifically, the refrigerant condition control unit 1220 may control the temperature of a refrigerant by applying thermal energy to the refrigerant moving in a flow path in the refrigerant condition control unit 1220. In this case, the refrigerant condition control unit 1220 may control the temperature of a refrigerant to be sprayed by controlling thermal energy applied to the refrigerant such that the skin surface temperature is controlled to a temperature corresponding to the temperature condition in which the blood vessel does not constrict, for example, the temperature of about 18° C. or higher or about 2° C. or lower.

Additionally, the refrigerant condition control unit 1220 may control the amount of a refrigerant by controlling thermal energy applied to a refrigerant moving in a flow path in the refrigerant condition control unit 1220. In this case, the refrigerant condition control unit 1220 may control the amount of a refrigerant such that cooling energy corresponding to the temperature condition in which the blood vessel does not constrict is applied to the skin surface. The refrigerant condition control unit 1220 may be preferably configured as a thermoelectric element such as a Peltier element.

The spraying unit 1230 may perform the spraying of a refrigerant. In this case, a refrigerant may be sprayed on the skin surface by the spraying unit 1230 according to a temperature and/or amount controlled by the refrigerant condition control unit 1220 described above such that the skin surface temperature is controlled to a temperature corresponding to the temperature condition in which the blood vessel does not constrict. The spraying unit 1230 may be preferably configured as the nozzle.

The control module 1400 may control a refrigerant to be sprayed through the spraying unit 1230 in the spraying section which includes the inter-cooling section P2 corresponding to a section in which a laser is output, the pre-cooling section P1 before the inter-cooling section P2, and the post-cooling section P3 after the inter-cooling.

Additionally, to cool the skin to a desired temperature, the control module 1400 may be configured to control the temperature of a refrigerant to be sprayed through the refrigerant condition control unit 1220 based on a skin temperature. In this case, the desired temperature may be any suitable temperature corresponding to the temperature condition in which the blood vessel does not constrict. The desired temperature, which is a skin surface temperature, may preferably be any suitable temperature of the temperatures of 2° C. or less or 18° C. or more. A skin temperature corresponding to the temperature condition in which the blood vessel does not constrict may preferably be preset as a temperature within the temperature range of 18° C. or more to 40° C. or less. Alternatively, a skin temperature corresponding to the temperature condition in which the blood vessel does not constrict may preferably be preset as a temperature within the temperature range of −10° C. or more to 2° C. or less.

In order to cool the skin to a desired temperature, the control module 1400 may be configured to control the amount of a refrigerant to be sprayed based on a skin temperature through the refrigerant condition control unit 1220 and/or the flow rate control unit 1210 to be described later.

Additionally, the control module 1400 may control the desired temperature to a set temperature or more (e.g., the temperature of 18° C. or more) at which the blood vessel under the skin constricts in the pre-cooling section P1.

Additionally, the control module 1400 may control the desired temperature to a set temperature or less (e.g., the temperature of 2° C. or more) at which the blood vessel under the skin constricts in the pre-cooling section P1.

Additionally, in the pre-cooling section P1, the control module 1400 may control the desired temperature to a skin temperature corresponding to the temperature of the blood vessel at which the blood vessel under the skin does not constrict, and may control the desired temperature to a skin temperature corresponding to the temperature of the blood vessel at which the blood vessel constricts in at least a portion of the post-cooling section P3. For example, in order to prevent a laser treatment from being interrupted due to the invisibleness of the absorption medium of a laser caused by the constriction of the blood vessel in the pre-cooling section P1, the desired temperature may be controlled to a skin temperature corresponding to the temperature of the blood vessel at which the blood vessel does not constrict. On the other hand, the post-cooling section P3 is a section after the stopping time of laser emission, and the blood vessel may be constricted in at least a portion of the post-cooling section P3. Accordingly, in at least a portion of the post-cooling section P3, the control module 1400 may control the desired temperature to a skin temperature corresponding to the temperature of the blood vessel at which the blood vessel constricts.

Additionally, the laser treatment device 100 having a cooling system disclosed in the present specification may include the flow rate control unit 1210. The flow rate control unit 1210 may preferably be configured as the valve.

The flow rate control unit 1210 may control the amount and/or flow of a refrigerant. Specifically, the flow rate control unit 1210 may control the amount of a refrigerant such that cooling energy corresponding to the temperature condition in which the blood vessel does not constrict is applied to a skin surface. By controlling the opening period of time and opening cycle of the flow rate control unit 1210, the amount and/or flow of a refrigerant may be controlled, and through this, the amount of cooling energy applied to the skin surface may be controlled, and accordingly, a skin surface temperature may be controlled to a temperature corresponding to the temperature condition in which the blood vessel does not constrict.

By controlling the spray amount of a refrigerant to be sprayed through the flow rate control unit 1210, the control module 1400 may control the desired temperature to a skin temperature corresponding to the temperature of the blood vessel at which the blood vessel under the skin does not constrict in the pre-cooling section P1. On the other hand by controlling the spray amount of a refrigerant to be sprayed through the flow rate control unit 1210, the control module 1400 may control the desired temperature to a skin temperature corresponding to the temperature of the blood vessel at which the blood vessel constricts in at least a portion of the post-cooling section P3.

The control module 1400 may receive and store the measured temperature (e.g., the skin surface temperature, the temperature of the refrigerant) from the sensing unit 1300, and the sensing unit 1300 may determine whether the measured temperature corresponds to a temperature correspond to the blood vessel relaxation temperature.

When the sensing unit 1300 determines that the measured temperature does not correspond to the blood vessel relaxation temperature, the control module 1400 may control the temperature and/or amount of a refrigerant by controlling the operation of the refrigerant condition control unit 1220 and/or the flow rate control unit 1210.

Specifically, when the sensing unit 1300 determines that the measured temperature does not correspond to the blood vessel relaxation temperature, the control module 1400 controls the amount of a current applied to the refrigerant condition control unit 1220 and/or whether to turn on/off power of the refrigerant condition control unit 1220 such that the temperature of a refrigerant can be controlled. Alternatively, when the sensing unit 1300 determines that the measured temperature does not correspond to the blood vessel relaxation temperature, the control module 1400 controls the amount of a current applied to the refrigerant condition control unit 1220 and/or whether to turn on/off the power of the refrigerant condition control unit 1220 such that the amount of a refrigerant can be controlled.

For example, when the sensing unit 1300 determines that the measured temperature does not correspond to the blood vessel relaxation temperature, the refrigerant condition control unit 1220 may apply different thermal energy to a refrigerant in each of the pre-cooling section P1 and the post-cooling section P3.

For example, when the sensing unit 1300 determines that the measured temperature does not correspond to the blood vessel relaxation temperature, the opening/closing cycle or the period of opening/closing time of the flow rate control unit 1210 in the pre-cooling section P1 may be controlled to be different from the opening/closing cycle or the period of opening/closing time in the post-cooling section P3.

On the other hand, when the sensing unit 1300 determines that the measured temperature corresponds to the blood vessel relaxation temperature, the control module 1400 may transmit the starting signal of laser emission to the laser module 1100. The laser module 1100 may be configured to output a laser by receiving the starting signal of the laser emission. However, this is not restrictive, and the sensing unit 1300 may display a notification that the measured temperature corresponds to a temperature corresponding to the blood vessel relaxation temperature on a separate display of the laser treatment device 100, and a user may directly perform a laser emission input.

Additionally, when a laser output starts, a laser emission signal is transmitted to the control module 1400, and the control module 1400 receives the laser emission signal and may transmit a refrigerant spray signal to the cooling module 1200, particularly, the spraying unit 1230 so as to spray a refrigerant by including at least a portion of the laser emission section. The cooling module 1200, particularly, the spraying unit 1230 may receive the refrigerant spray signal and may spray a refrigerant by including at least a portion of the laser emission section.

Additionally, when a laser output starts, the laser emission signal is transmitted to the control module 1400, and the control module 1400 may receive the laser emission signal and may control the amount of a current applied to the refrigerant condition control unit 1220 and/or whether to turn on/off the power of the refrigerant condition control unit 1220 so as to control the temperature and/or amount of a sprayed refrigerant in at least a portion of the laser emission section. Alternatively, when a laser output starts, the laser emission signal is transmitted to the control module 1400, and the control module 1400 may receive the laser emission signal and may control the period of opening/closing time and opening/closing cycle of the flow rate control unit 1210 so as to control the amount of a sprayed refrigerant in at least a portion of the laser emission section.

Hereinafter, the method of the treatment and/or treatment of a vascular lesion by the laser treatment device 100 disclosed in the present specification will be described in detail with reference to FIGS. 23 and 24.

Figure 23:
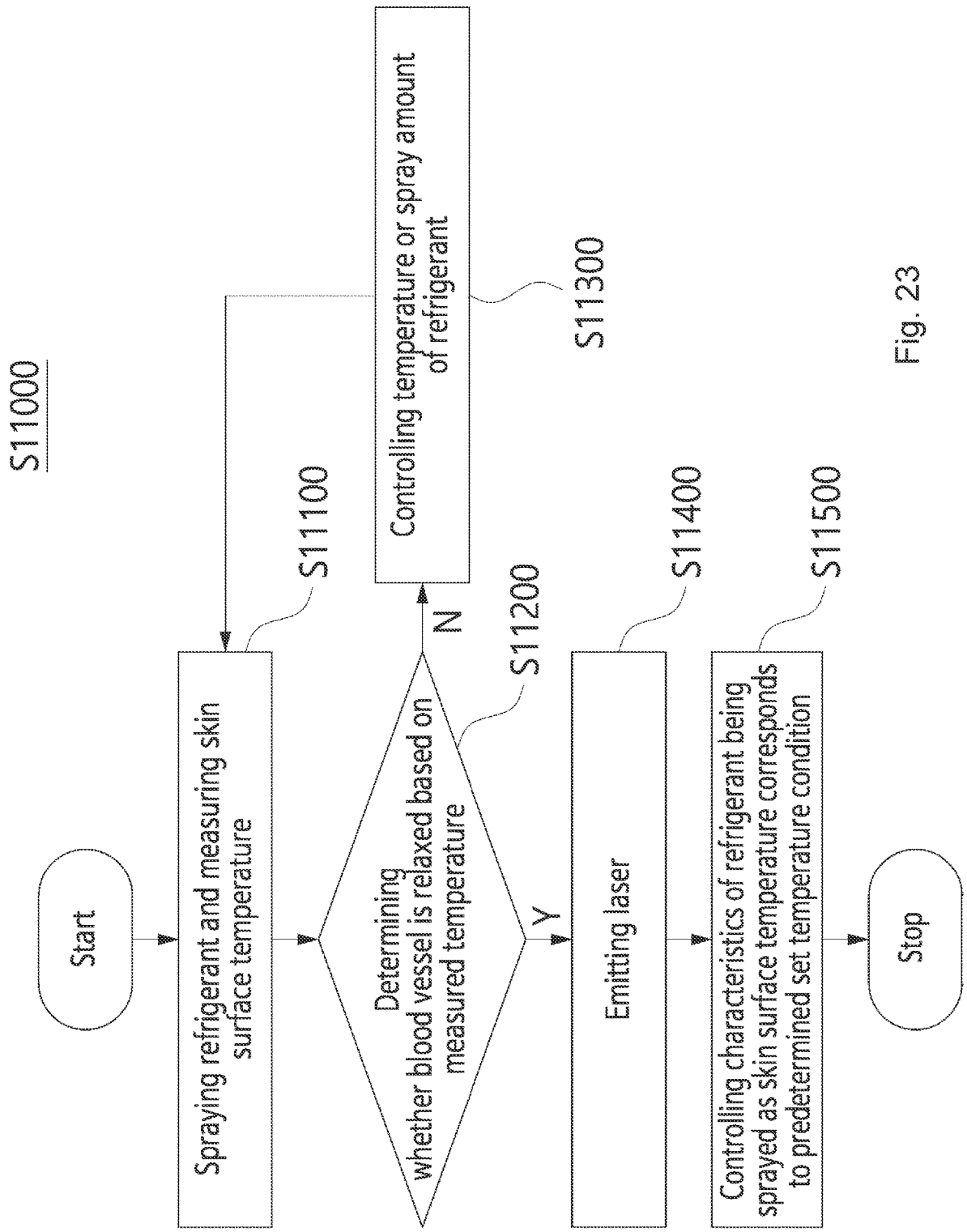
FIG. 23 is a flowchart of the method of performing the treatment and/or treatment of a vascular lesion by the laser treatment device disclosed in the present specification.

FIG. 23 is a flowchart of the method S11000 of the treatment and/or treatment of a vascular lesion by the laser treatment device 100 disclosed in the present specification.

Figure 24:
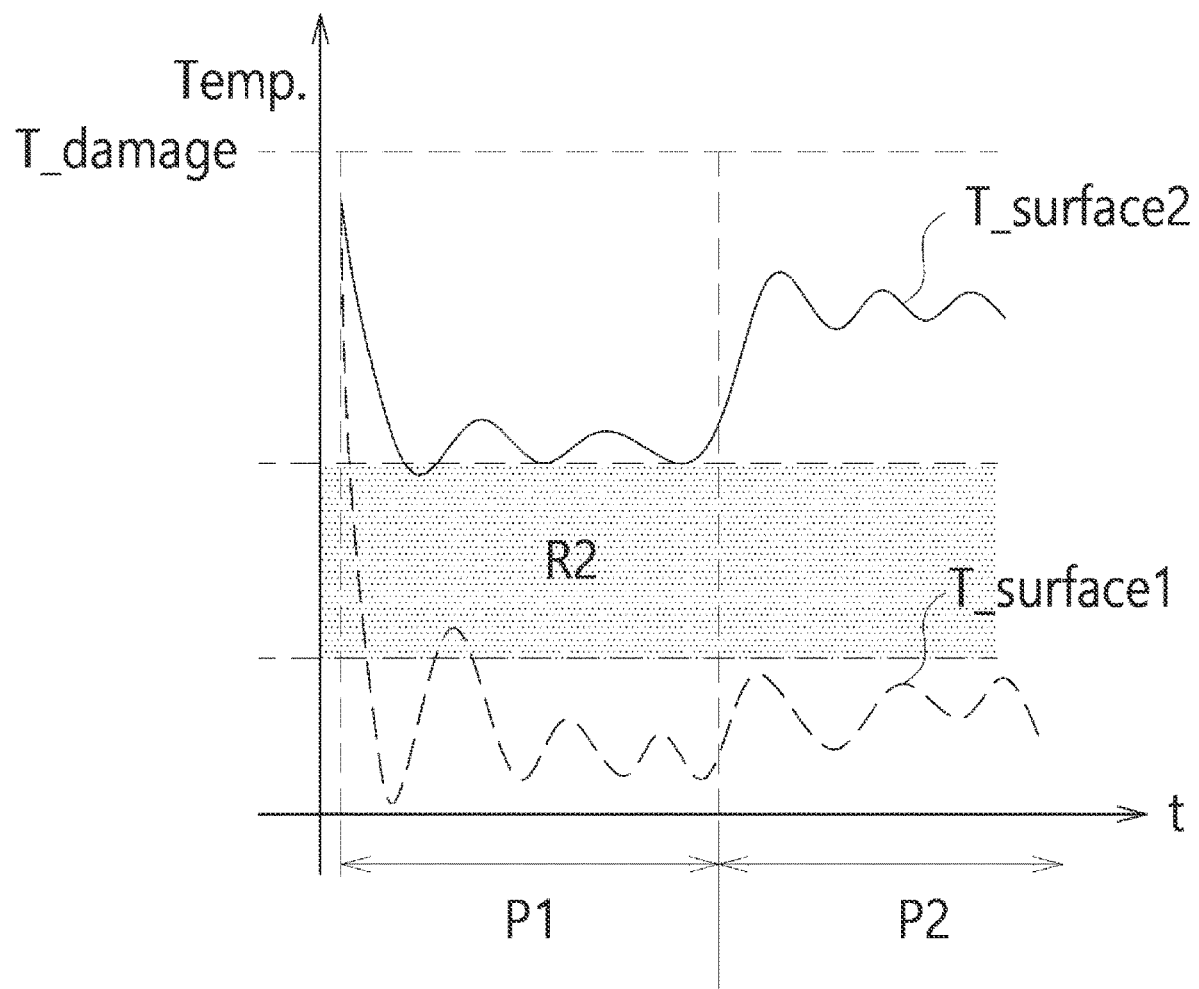
FIG. 24 is a graph illustrating the change of the skin surface temperature controlled according to the exemplary embodiment of the method of performing the treatment and/or therapy of a vascular lesion by the laser treatment device disclosed in the present specification.

FIG. 24 is a graph illustrating the change of skin surface temperatures controlled according to the exemplary embodiment of the treatment/therapeutic method of a vascular lesion by the laser treatment device disclosed in the present specification 100. Here, 'T_surface1' of FIG. 24 may refer to a skin surface temperature according to the embodiment of the present specification. In addition, 'T_surface2' of FIG. 24 may refer to a skin surface temperature according to the embodiment of the present specification. In addition, 'T_damage' of FIG. 24 may refer to a skin damage temperature of the present specification. In addition, 'R2' of FIG. 24 may refer to a skin surface temperature range in which the blood vessel constricts in the present specification.

Referring to FIG. 23, the surgical treatment/therapeutic method of a vascular lesion by the laser treatment device disclosed in the present specification 100 may include: a spraying a refrigerant and measuring a skin surface temperature at S11100; determining whether a blood vessel is relaxed based on a measured skin surface temperature at S11200; controlling the temperature and/or spray amount of a refrigerant at S11300; emitting a laser at S11400; and controlling the characteristics of a sprayed refrigerant such that the skin surface temperature is close to a set temperature at S11500.

The spraying of a refrigerant at S11100 may mean the pre-cooling. That is, the spraying of a refrigerant may mean spraying a refrigerant before the laser emission starts. Accordingly, the description in relation to the pre-cooling in FIGS. 4 to 6 may be inferred and applied.

At S11100, a refrigerant may be sprayed by having the temperature of the refrigerant corresponding to a temperature at which the blood vessel does not constrict. Additionally, a refrigerant may be sprayed in the amount of the refrigerant for applying cooling energy such that the skin surface temperature is a temperature at which the blood vessel does not constrict.

Additionally, the measuring of the skin surface temperature at S11100 may be performed by the sensing unit 1300. The sensing unit 1300 may measure the skin surface temperature and may transmit data on temperature information related thereto to the control module 1400. The data related to the skin surface temperature information may be used as a basis for determining whether the blood vessel is relaxed at S11200 to be described later.

In the block diagram of S11100 of FIG. 23, the skin surface temperature is illustrated to be only measured, but this is only an example, and the temperature of 'a refrigerant' may be measured and data on the temperature of the refrigerant may be transmitted to the control module 1400, and based on the information on the temperature of the refrigerant, the temperature of 'a refrigerant' corresponding to a temperature at which the blood vessel does not constrict may be estimated and may be used as a basis for determining whether the blood vessel is relaxed at S11200 to be described later. In addition, the information on the temperature of 'a refrigerant' may be used for determining the temperature of a refrigerant to be controlled at S11300 to be described later or in the same vascular lesion treatment.

Additionally, the amount of a refrigerant may be measured in various ways by the sensing unit 1300, and information related to the amount of a refrigerant may be transmitted to the control module 1400, and based on the amount of a refrigerant, the amount of a refrigerant corresponding to a temperature at which the blood vessel does not constrict may be estimated and may be used as a basis for determining whether the blood vessel is relaxed at S11200 to be described later. In addition, the information related to the amount of a refrigerant may be used for determining the temperature of a refrigerant to be controlled at S11300 to be described later or in the same vascular lesion treatment.

At S11200, whether the blood vessel is relaxed may be determined by the control module 1400 based on temperature information related to the skin surface temperature measured at S11100. Specifically, whether the blood vessel is relaxed may be determined based on whether the measured skin surface temperature corresponds to the blood vessel relaxation temperature (e.g., the temperature of 2° C. or less or 18° C. or more). In other words, based on whether the skin surface temperature is measured as the skin surface temperature corresponding to a temperature range in which the blood vessel constricts (e.g., a temperature other than 2° C. to 18° C.), whether the blood vessel is constricted or relaxed may be determined. In addition, the control module 1400 may store information on the skin surface temperature measured at S11100 and the result of the determining of whether the blood vessel is relaxed according to the associated temperature information at S11200. Here, the information on the determining result of whether the blood vessel is relaxed may be used as a basis for controlling the temperature or spray amount of a refrigerant at S11300.

As described above, it has been described that whether the blood vessel is relaxed is determined based on 'the skin surface temperature', but this is only an example, and the skin surface temperature may be used to measure blood pressure, the flow amount of blood, and a blood oxygen level.

At S11200, when the measured skin surface temperature does not correspond to a temperature corresponding to the blood vessel relaxation temperature, that is, when the measured skin surface temperature corresponds to a temperature corresponding to a blood vessel constriction temperature, the step of S11300 may proceed.

As described above, S11200 shows whether the blood vessel is relaxed is 'determined' based on the skin surface temperature measured at S11100, but this is only an example, and the 'determining' of whether the blood vessel is relaxed based on the skin surface temperature may be omitted. For example, before the laser treatment starts, a skin temperature may be set as a specific temperature which does not correspond to the temperature range of the skin (e.g., R2 of FIG. 24) in which the blood vessel constricts. In this case, even if whether the blood vessel is relaxed is not 'determined', the control module 1400 may be configured to control the temperature or spray amount of a refrigerant in consideration of the skin surface temperature measured at S11100 and the set skin temperature. Specifically, even if whether the blood vessel is relaxed is not determined, the control module 1400 may control the temperature or spray amount of a refrigerant in consideration of difference between the skin surface temperature measured at S11100 and the preset skin temperature. In this case, the laser emission at S11400 may be performed by a user's the laser emission input. Alternatively, a laser may be emitted after a predetermined period of time elapses from time at which a refrigerant starts to be sprayed at S11100.

At S11300, the control module 1400 may control the temperature and/or spray amount of a refrigerant based on information on the temperature of a refrigerant measured at S11100, information on the amount of a refrigerant, information on the skin surface temperature, and information on the determining of whether the blood vessel is relaxed at S11200.

Specifically, at S11300, the control module 1400 may control the temperature of a refrigerant through the refrigerant condition control unit 1220 such that the skin surface temperature is a skin surface temperature corresponding to a temperature at which the blood vessel does not constrict. In this case, the temperature of the refrigerant may be a temperature of a refrigerant corresponding to 2° C. or less or 18° C. or more which is a skin surface temperature at which the blood vessel does not constrict. Alternatively, the control module 1400 may control the amount of a refrigerant through the refrigerant condition control unit 1220 such that the skin surface temperature is controlled to a temperature corresponding to a temperature at which the blood vessel does not constrict. Cooling energy applied to the skin surface may be controlled by controlling the amount of a refrigerant, and thus the skin surface temperature may be controlled to a temperature corresponding to a temperature condition in which the blood vessel is relaxed.

Additionally, at S11300, the amount of a refrigerant may be controlled through the flow rate control unit 1210 such that cooling energy corresponding to the skin surface temperature at which the blood vessel does not constrict is applied to the skin surface.

For example, the control module 1400 may control the temperature and/or spray amount of a refrigerant based on information on whether the blood vessel is relaxed determined at S11200 according to 'the skin surface temperature' measured at S11100.

For example, when the measured skin surface temperature is a temperature (e.g., the skin surface temperature of 2° C. or more to 18° C. or less) corresponding to the blood vessel constriction temperature condition, the control module 1400 may increase the temperature of the refrigerant to a temperature corresponding to the blood vessel relaxation temperature condition through 'the refrigerant condition control unit' 1220 and may control the skin surface temperature to a temperature (e.g., controlling the skin surface temperature to a temperature of 18° C. or more) corresponding to the blood vessel relaxation temperature condition. Alternatively, the control module 1400 may decrease the temperature of a refrigerant to a temperature corresponding to the blood vessel relaxation temperature condition through 'the refrigerant condition control unit' 1220 and may control the skin surface temperature to a temperature corresponding to the blood vessel relaxation temperature condition (e.g., controlling the skin surface temperature to a temperature of 2° C. or less).

For another example, when the measured skin surface temperature is a temperature corresponding to the blood vessel constriction temperature condition (e.g., the skin surface temperature of 2° C. or more and 18° C. or less), the control module 1400 may increase the amount of a refrigerant through 'the flow rate control unit' 1210 such that the skin surface temperature is 'a skin surface temperature' (e.g., the skin surface temperature of 2° C. or less) corresponding to the blood vessel relaxation temperature condition and may increase cooling energy applied to the skin surface. Alternatively, the control module 1400 may decrease the amount of a refrigerant through 'the flow rate control unit' 1210, such that the skin surface temperature is a skin surface temperature corresponding to the blood vessel relaxation temperature condition (e.g., the skin surface temperature of 18° C. or more) and may decrease cooling energy applied to the skin surface.

In an embodiment, the control module 1400 may control the temperature and/or spray amount of a refrigerant based on information on whether the blood vessel is relaxed determined at S11200 according to 'the temperature of a refrigerant' measured at S11100. Since the temperature of a refrigerant is the direct variable of the skin surface temperature, the control module 1400 may control the temperature and/or spray amount of a refrigerant through the temperature of a refrigerant as well as the skin surface temperature. For example, when the temperature of a refrigerant is a temperature corresponding to the blood vessel constriction temperature condition, the control module 1400 may increase the temperature of the refrigerant to a temperature corresponding to the blood vessel relaxation temperature condition or may decrease the temperature of the refrigerant to a temperature corresponding to the blood vessel relaxation temperature condition.

For example, when 'the temperature of a refrigerant' measured at S11000 is a temperature corresponding to the blood vessel constriction temperature condition, the control module 1400 may control 'the temperature of a refrigerant' through 'the refrigerant condition control unit' 1220 such that the skin surface temperature is a skin surface temperature corresponding to the blood vessel relaxation temperature condition (e.g., the skin surface temperature of 2° C. or less or 18° C. or more). Alternatively, the control module 1400 may control the amount of a refrigerant through 'the refrigerant condition control unit' 1220 such that the skin surface temperature is a skin surface temperature corresponding to the blood vessel relaxation temperature condition (e.g., the skin surface temperature of 2° C. or less or 18° C. or more) and may control cooling energy applied to the skin surface.

For example, when 'the temperature of a refrigerant' measured at S11000 is a temperature corresponding to the blood vessel constriction temperature condition, the control module 1400 may increase 'the amount of a refrigerant' through 'the flow rate control unit' 1210 such that the skin surface temperature is a skin surface temperature corresponding to the blood vessel relaxation temperature condition (e.g., the skin surface temperature of 2° C. or less) and may increase cooling energy applied to the skin surface. Alternatively, the control module 1400 may decrease the amount of a refrigerant through the flow rate control unit 1210, such that the skin surface temperature is a skin surface temperature corresponding to the blood vessel relaxation temperature condition (e.g., the skin surface temperature of 18° C. or more) and may decrease cooling energy applied to the skin surface.

For example, the control module 1400 may control 'the temperature of a refrigerant' through 'the refrigerant condition control unit' 1220 such that the skin surface temperature is a skin surface temperature corresponding to the blood vessel relaxation temperature condition (e.g., the skin surface temperature of 2° C. or less or 18° C. or more) based on information on whether the blood vessel is relaxed determined at S11200 according to 'the amount of a refrigerant' measured at S11100. Alternatively, the control module 1400 may control the amount of a refrigerant through 'the refrigerant condition control unit' 1220 such that the skin surface temperature is a skin surface temperature corresponding to the blood vessel relaxation temperature condition (e.g., the skin surface temperature of 2° C. or less or 18° C. or more) and may control cooling energy applied to the skin surface.

For example, the control module 1400 may increase 'the amount of a refrigerant' through 'the flow rate control unit' 1210 such that the skin surface temperature is a skin surface temperature corresponding to the blood vessel relaxation temperature condition (e.g., the skin surface temperature of 2° C. or less) based on information on whether the blood vessel is relaxed determined at S11200 according to 'the amount of a refrigerant' measured at S11100 and may increase cooling energy applied to the skin surface. Alternatively, the control module 1400 may decrease 'the amount of a refrigerant' through 'the flow rate control unit' 1210 such that the skin surface temperature is a skin surface temperature corresponding to the blood vessel relaxation temperature condition (e.g., the skin surface temperature of 18° C. or more) based on information on whether the blood vessel is relaxed determined at S11200 according to the amount of a refrigerant measured at S11100 and may decrease cooling energy applied to the skin surface.

After S11300, a refrigerant may be sprayed according to the temperature and/or amount of a refrigerant controlled by the control module 1400 through the refrigerant condition control unit 1220 and/or the flow rate control unit 1210, and accordingly, the measuring S11100 of the skin surface temperature and a series of steps may proceed. Additionally, information on the change of the skin surface temperature, the temperature of a refrigerant, and the amount of a refrigerant at S11000 according to the change of the temperature and/or amount of a refrigerant at S11300 may be transmitted to and stored in the control module 1400 and may be used as information for determining whether the blood vessel is relaxed at S11200. In addition, information on the change of the skin surface temperature, the temperature of a refrigerant, and the amount of a refrigerant at S11000 according to the change of the temperature and/or amount of a refrigerant at S11300 may be transmitted to and stored in the control module 1400 and may be used as a basis for controlling the temperature or spray amount of a refrigerant at S11300 to be performed later.

At S11200, when the measured skin surface temperature corresponds to a temperature corresponding to the blood vessel relaxation temperature, that is, when the measured skin surface temperature does not correspond to a temperature corresponding to the blood vessel constriction temperature, the emitting of a laser at S11400 may be performed. The laser at S11400 may be a laser with the degree of high absorption in the blood vessel, and may be selected as any suitable laser having a wavelength band capable of reaching the depth at which the blood vessel is located. Description about any suitable principles and advantages in FIGS. 1, 2, 3, 4, 5, and 7 may be inferred and applied for laser emission.

At S11500, the control module 1400 may control the characteristics of a refrigerant, such as the temperature and amount of a sprayed refrigerant, such that the skin surface temperature is close to a set temperature.

At S11500, the skin may be damaged by the increase of the skin surface temperature due to laser irradiation. Accordingly, at S11500, the inter-cooling may be performed. At S11500, when the inter-cooling is performed, description about the set temperature and set temperature condition of the inter-cooling explained in relation to FIGS. 1, 2, 3, 4, 5, and 7 and any suitable principle and advantages of the inter-cooling may be inferred and applied. In other words, in order to prevent a skin temperature from reaching the skin damage temperature due to laser irradiation during the inter-cooling, the operation and driving method of the control module 1400, the cooling module 1200, and the laser module 1100 described above may be suitably applied.

For example, referring to FIGS. 23 and 24, in a case in which a measured skin temperature corresponds to the blood vessel relaxation temperature (e.g., 2° C. or less) at S11200, as the skin surface temperature rises according to laser irradiation, the skin surface temperature corresponds to a vasoconstriction range (e.g., the case of the skin surface temperature (T_surface1) of a dotted line of FIG. 24), and accordingly, during the laser irradiation, a blood vessel constricts, which may lead to side effects and inefficiency of laser treatment. Accordingly, when the measured skin temperature corresponds to the blood vessel relaxation temperature (e.g., 2° C. or less) at S11200, a preset skin surface temperature may be preset as the temperature of 2° C. or less at S11500.

For example, in the case in which the measured skin temperature corresponds to the blood vessel relaxation temperature (e.g., 2° C. or less) at S11200, the set temperature may be set in consideration of a laser interfering substance such as frost of the skin surface. Specifically, during laser emission, when the laser interfering substance such as frost is present on the skin surface, the frost may scatter a laser, which may cause inefficient laser treatment, and accordingly, the set temperature of the skin surface may be set as the temperature of 0° C. or more at which the laser interfering substance such as frost is not present on the skin surface.

For another example, in the case in which the measured skin temperature corresponds to the blood vessel relaxation temperature (e.g., 2° C. or less) at S11200, the set temperature may be set in consideration of a laser interfering substance such as ice in the laser emission path. Specifically, during the laser emission, when multiple laser interfering substances, such as ice are present in the laser emission path, the substances may scatter laser which may cause inefficient laser treatment, and accordingly, the set temperature of the skin surface may be set as a temperature at which the laser interfering substance such as ice in the laser emission path is minimized during the laser emission.

For another example, in the case in which the measured skin temperature corresponds to the blood vessel relaxation temperature (e.g., 2° C. or less) at S11200, after the skin surface temperature is controlled to 18° C. or more by additionally controlling the temperature and/or amount of a refrigerant just before the starting of the laser emission, a laser may be emitted. Specifically, FIG. 23 illustrates that when the measured skin temperature corresponds to the blood vessel relaxation temperature (e.g., 2° C. or less) at S11200, the laser emission is performed at S11400, but as the laser emission progresses, heat is accumulated on the skin surface, and the skin surface temperature may fall within a vasoconstriction temperature range (2° C. or more to 18° C. or less). Accordingly, to minimize this possibility, before the starting of the laser emission at S11400, the control module 1400 may be configured to emit laser after the skin surface temperature is controlled to 18° C. or more, which is one temperature condition corresponding to the blood vessel relaxation temperature, by the refrigerant condition control unit 1220 and/or the flow rate control unit 1210.

For example, referring to FIGS. 23 and 24, in a case in which the measured skin temperature corresponds to the blood vessel relaxation temperature (e.g., 18° C. or more) at S11200, the skin surface temperature may be relatively less likely to correspond to the vasoconstriction range (e.g., the case of the skin surface temperature (T_surface2) of the solid line of FIG. 24) as the skin surface temperature increases according to the laser emission. However, as the skin surface temperature rises according to the laser emission, the skin surface temperature may reach the skin damage temperature. Accordingly, in this case, at S11500, the set temperature of the skin surface may be set in consideration of the skin damage temperature, and the control module 1400 may control the temperature and/or amount of a refrigerant sprayed such that the skin surface temperature is close to the set temperature in consideration of the skin damage temperature. Through this, the set temperature may be set such that the skin surface temperature does not reach the skin damage temperature so as to minimize the possibility of skin damage. Description of the predetermined second set temperature Ts2 described in relation to FIG. 7 may be inferred and applied to this.

For example, at S11500, the set temperature may be preset by considering a temperature at which the temperature of a blood vessel which is a target can apply heat damage to the blood vessel, and the desired temperature of a target described with reference to FIG. 7 may be inferred and be applied thereto.

At S11500, by considering any suitable set temperature selected in consideration of various factors mentioned above, the control module 1400 can be configured such that a refrigerant is sprayed by controlling the characteristics of the refrigerant.

Additionally, although not shown in FIGS. 23 and 24, S11500 may be related to post-cooling after the laser emission is completed. In this case, description such as the set temperature and set temperature condition of post-cooling described in relation to FIGS. 1, 2, 3, 4, 5, and 8 and a suitable principle and advantages for the post-cooling may be inferred and applied. In other words, in order to restore a skin temperature increased by laser emission to a normal skin temperature or to minimize pain during the post-cooling, the operations and riving methods of the control module 1400 and the cooling module 1200 described above may be appropriately applied.

Features, structures, effects, etc. described in the above embodiments are included in at least one embodiment of the present disclosure, and are not necessarily limited to only one embodiment. Furthermore, features, structures, and effects, etc. illustrated in each embodiment may be combined or modified for other embodiments by those skilled in the art to which the embodiments belong. Accordingly, contents related to the combination and modification should be interpreted as being included in the scope of the present disclosure.

Additionally, in the above, the embodiments have been mainly described but are only examples and do not limit the present disclosure, and those skilled in the art to which the present disclosure pertains will be able to see that various modifications and applications not exemplified above are possible without departing from the essential characteristics of the present embodiments. That is, each component specifically shown in the embodiments may be modified. And differences related to these modifications and applications should be construed as being included in the scope of the present disclosure stipulated in the appended claims.

The invention claimed is:

1. A laser device having a cooling system, the device comprising:
   a laser module configured to irradiate a laser to a target including a blood vessel;
   a sensor configured to detect a temperature of a surface corresponding to the target;
   a cooling module comprising:
      an inlet configured to receive a refrigerant;
      a nozzle configured to spray the refrigerant;
      a conduit configured to provide at least part of a flow path from the inlet to the nozzle for the refrigerant;
      a valve configured to control a flow of the refrigerant in the flow path;
      a refrigerant condition controller arranged between the inlet and the nozzle and configured to provide a heat to the refrigerant before the refrigerant is sprayed by the nozzle; and
   a controller configured to:
      control the valve of the cooling module to spray a refrigerant to the surface,
      control the refrigerant condition controller to provide a heat to the refrigerant before being sprayed based on a desired temperature and the detected temperature by the sensor, and
      control the laser module to irradiate the laser while the cooling module is controlled to spray the refrigerant,
   wherein the laser module is controlled to irradiate the laser from a first time point to a second time point, and
   wherein, before the first time point, the desired temperature is set to be out of a critical temperature range that corresponds to a temperature range causing vasoconstriction.

2. The laser device of claim 1, wherein the critical temperature range is lower than or equal to 18° C.

3. The laser device of claim 1, wherein the critical temperature range is between 2° C. and 18° C.

4. The laser device of claim 1, wherein the desired temperature is set higher than 18° C.

5. The laser device of claim 1, wherein the desired temperature is set between 18° C. and 40° C.

6. The laser device of claim 1, wherein the desired temperature is set lower than 2° C. or higher than 18° C.

7. The laser device of claim 1, wherein, between the first time point and the second time point, the desired temperature is set in the critical temperature range.

8. The laser device of claim 1, wherein, between the first time point and the second time point, the desired temperature is set higher than a frost critical temperature that corresponds to a temperature causing frost on the surface.

9. The laser device of claim 8, wherein, between the first time point and the second time point, the desired temperature is set higher than or equal to 0° C.

10. The laser device of claim 8, wherein the frost critical temperature is higher than or equal to 0° C.

11. The laser device of claim 1, wherein, after the second time point, the desired temperature is set less than or equal to 10° C.

12. The laser device of claim 1, wherein the controller is further configured to control the laser module to irradiate the laser when the detected temperature of the surface meets a predetermined condition.

13. The laser device of claim 12, wherein the predetermined condition is a temperature range causing vasorelaxation.

14. The laser device of claim 12, wherein the predetermined condition is a temperature range of higher than or equal to 18° C.

15. The laser device of claim 12, wherein the controller is further configured to determine whether the detected temperature of the surface meets the predetermined condition before the first time point.

* * * * *